(12) United States Patent
Oldham et al.

(10) Patent No.: US 12,091,712 B2
(45) Date of Patent: Sep. 17, 2024

(54) SYSTEMS AND METHODS FOR MEASUREMENT AND SEQUENCING OF BIO-MOLECULES

(71) Applicant: Illumina Cambridge, Ltd., Cambridge (GB)

(72) Inventors: Mark F. Oldham, Emerald Hills, CA (US); Eric S. Nordman, Palo Alto, CA (US); Timothy M. Woudenberg, San Francisco, CA (US); Gaurav Goyal, Menlo Park, CA (US); Masoud Vakili, Los Altos, CA (US); Toshihiko Honkura, Tokyo (JP); Sam Woo, Redwood City, CA (US); Hisao Kawasaki, Kanagawa (JP); Kazusuke Mihara, Kyoto (JP)

(73) Assignee: Illumina Cambridge, Ltd., Cambridge (GB)

(*) Notice: Subject to any disclaimer, the term of this patent is extended or adjusted under 35 U.S.C. 154(b) by 807 days.

(21) Appl. No.: 16/169,756

(22) Filed: Oct. 24, 2018

(65) Prior Publication Data

US 2019/0169684 A1   Jun. 6, 2019

Related U.S. Application Data

(63) Continuation of application No. PCT/US2017/029978, filed on Apr. 27, 2017.
(Continued)

(51) Int. Cl.
*C12Q 1/6869* (2018.01)
*C12Q 1/68* (2018.01)
(Continued)

(52) U.S. Cl.
CPC ............ *C12Q 1/6869* (2013.01); *C12Q 1/68* (2013.01); *G01N 27/3275* (2013.01);
(Continued)

(58) Field of Classification Search
CPC .......... C12Q 1/68–6841; C12Q 1/6869–6874; C12Q 2565/631; G01N 27/3276;
(Continued)

(56) References Cited

U.S. PATENT DOCUMENTS 5,092,972 A   3/1992   Ghowsi
5,122,248 A   6/1992   Karger et al.
(Continued)

FOREIGN PATENT DOCUMENTS

CN   1828849 A      9/2006
CN   101046458 A   10/2007
(Continued)

OTHER PUBLICATIONS

Chen et al., Hybridization sensing by electrical enhancement with nanoparticles in nanogap, Journal of Vacuum Science & Technology B: Microelectronics and Nanometer Structures Processing, Measurement, and Phenomena, vol. 26, pp. 2572-2577 (2008) (Year: 2008).*

(Continued)

*Primary Examiner* — James Lin
*Assistant Examiner* — Vivian A Tran
(74) *Attorney, Agent, or Firm* — Dierker & Kavanaugh, P.C.

(57) ABSTRACT

The present disclosure provides systems and methods for sequencing nucleic acid molecules using tunneling labels. A sequence of a nucleic acid molecule may be identified with high accuracy using a chip comprising sensors, wherein each individual sensor may comprise at least two electrodes separated by a gap. The electrodes may be configured to
(Continued)

generate at least one electrical signal upon binding of a tunneling label associated with a nucleotide. Epigenetic information can also be determined at the same time as a nucleic acid sequence.

20 Claims, 32 Drawing Sheets

Related U.S. Application Data

(60) Provisional application No. 62/385,782, filed on Sep. 9, 2016, provisional application No. 62/359,648, filed on Jul. 7, 2016, provisional application No. 62/328,527, filed on Apr. 27, 2016.

(51) Int. Cl.
  G01N 27/327    (2006.01)
  G01N 33/00     (2006.01)
  G01N 33/487    (2006.01)

(52) U.S. Cl.
  CPC ..... *G01N 27/3276* (2013.01); *G01N 27/3278* (2013.01); *G01N 33/00* (2013.01); *G01N 33/48721* (2013.01); *C12Q 2565/631* (2013.01)

(58) Field of Classification Search
  CPC .............. G01N 27/3275; G01N 33/00; G01N 33/48721; G01N 27/3278
  See application file for complete search history.

(56) References Cited

U.S. PATENT DOCUMENTS

| | | |
|---|---|---|
| 5,151,164 A | 9/1992 | Blanchard et al. |
| 5,262,031 A | 11/1993 | Lux et al. |
| 5,329,236 A | 7/1994 | Gemma et al. |
| 5,593,838 A | 1/1997 | Zanzucchi et al. |
| 5,906,723 A | 5/1999 | Mathies et al. |
| 5,929,208 A | 7/1999 | Heller et al. |
| 6,159,353 A | 12/2000 | West et al. |
| 6,447,663 B1 | 9/2002 | Lee et al. |
| 6,491,805 B1 | 12/2002 | Gordon et al. |
| 6,613,513 B1 | 9/2003 | Parce et al. |
| 6,905,586 B2 | 6/2005 | Lee et al. |
| 7,033,476 B2 | 4/2006 | Lee et al. |
| 7,468,271 B2 | 12/2008 | Golovchenko et al. |
| 7,892,414 B1 | 2/2011 | Sumner |
| 7,918,979 B2 | 4/2011 | Han et al. |
| 8,105,471 B1 | 1/2012 | Han et al. |
| 8,236,595 B2 | 8/2012 | Agarwal et al. |
| 8,333,934 B2 | 12/2012 | Cao et al. |
| 8,652,779 B2 | 2/2014 | Turner et al. |
| 9,194,838 B2 | 11/2015 | Taniguchi et al. |
| 9,506,894 B2 | 11/2016 | Kawai et al. |
| 9,535,033 B2 | 1/2017 | Kawai et al. |
| 9,644,236 B2 | 5/2017 | Kawai et al. |
| 10,202,644 B2 | 2/2019 | Taniguchi et al. |
| 10,261,066 B2 | 4/2019 | Ikeda et al. |
| 10,413,903 B2 | 9/2019 | Taniguchi |
| 10,438,811 B1 | 10/2019 | Ikeda |
| 10,466,228 B2 | 11/2019 | Ikeda et al. |
| 10,557,167 B2 | 2/2020 | Kawai et al. |
| 2001/0046681 A1 | 11/2001 | Senapathy |
| 2002/0046953 A1 | 4/2002 | Lee et al. |
| 2002/0081744 A1 | 6/2002 | Chan et al. |
| 2002/0168671 A1 | 11/2002 | Burns et al. |
| 2002/0168810 A1 | 11/2002 | Jackson |
| 2003/0052006 A1 | 3/2003 | Noca et al. |
| 2003/0075445 A1 | 4/2003 | Woudenberg et al. |
| 2003/0085719 A1 | 5/2003 | Yoon et al. |
| 2003/0089606 A1 | 5/2003 | Parce et al. |
| 2003/0104428 A1 | 6/2003 | Branton et al. |
| 2003/0141189 A1 | 7/2003 | Lee et al. |
| 2003/0207326 A1 | 11/2003 | Su et al. |
| 2004/0124084 A1 | 7/2004 | Lee et al. |
| 2004/0144658 A1 | 7/2004 | Flory |
| 2004/0161708 A1 | 8/2004 | Nagase et al. |
| 2005/0048513 A1 | 3/2005 | Harwit et al. |
| 2005/0051768 A1 | 3/2005 | Kim et al. |
| 2005/0061669 A1 | 3/2005 | Woudenberg et al. |
| 2005/0074774 A1* | 4/2005 | Woudenberg ........ C12Q 1/6858 506/4 |
| 2005/0084865 A1 | 4/2005 | Yu et al. |
| 2005/0112860 A1 | 5/2005 | Park et al. |
| 2005/0127035 A1 | 6/2005 | Ling et al. |
| 2005/0136419 A1 | 6/2005 | Lee |
| 2005/0202444 A1 | 9/2005 | Zhu |
| 2005/0202446 A1 | 9/2005 | Yang et al. |
| 2005/0227239 A1 | 10/2005 | Joyce |
| 2006/0011480 A1 | 1/2006 | Sano et al. |
| 2006/0057585 A1 | 3/2006 | McAllister |
| 2006/0071209 A1 | 4/2006 | Flory et al. |
| 2006/0154399 A1 | 7/2006 | Sauer et al. |
| 2006/0154400 A1 | 7/2006 | Choi et al. |
| 2006/0210995 A1 | 9/2006 | Joyce |
| 2006/0275911 A1 | 12/2006 | Wang et al. |
| 2007/0029911 A1 | 2/2007 | Hudspeth et al. |
| 2007/0042366 A1 | 2/2007 | Ling |
| 2007/0048745 A1 | 3/2007 | Joyce et al. |
| 2007/0099211 A1* | 5/2007 | Aivazachvili ........ C12Q 1/6825 435/5 |
| 2007/0171714 A1 | 7/2007 | Wu et al. |
| 2007/0183198 A1 | 8/2007 | Otsuka et al. |
| 2008/0077607 A1 | 3/2008 | Gatawood et al. |
| 2008/0119366 A1 | 5/2008 | Sauer et al. |
| 2008/0171316 A1 | 7/2008 | Golovchenko et al. |
| 2008/0202931 A1 | 8/2008 | Petsev et al. |
| 2008/0215252 A1 | 9/2008 | Kawai et al. |
| 2008/0248561 A1 | 10/2008 | Golovchenko et al. |
| 2009/0023146 A1 | 1/2009 | Harnack et al. |
| 2009/0155917 A1 | 6/2009 | Umezawa et al. |
| 2009/0215156 A1 | 8/2009 | Chung et al. |
| 2009/0229854 A1 | 9/2009 | Fredenberg et al. |
| 2009/0242429 A1 | 10/2009 | Sitdikov et al. |
| 2009/0283412 A1 | 11/2009 | Sansinena et al. |
| 2009/0286936 A1 | 11/2009 | Ogata et al. |
| 2009/0305273 A1 | 12/2009 | Cao et al. |
| 2010/0025249 A1 | 2/2010 | Polonsky et al. |
| 2010/0066348 A1 | 3/2010 | Merz et al. |
| 2010/0084276 A1 | 4/2010 | Lindsay et al. |
| 2010/0184062 A1 | 7/2010 | Steinmuller-Nethl et al. |
| 2010/0188109 A1 | 7/2010 | Edel et al. |
| 2010/0243449 A1 | 9/2010 | Oliver |
| 2010/0267158 A1 | 10/2010 | Chou et al. |
| 2010/0292101 A1 | 11/2010 | So |
| 2010/0331194 A1* | 12/2010 | Turner ................. G01N 27/447 506/2 |
| 2011/0056845 A1 | 3/2011 | Stellacci et al. |
| 2011/0171634 A1 | 7/2011 | Xiao et al. |
| 2011/0179852 A1 | 7/2011 | Polonsky et al. |
| 2011/0181150 A1 | 7/2011 | Mahameed et al. |
| 2011/0193183 A1 | 8/2011 | Agarwal et al. |
| 2011/0236984 A1 | 9/2011 | Sun et al. |
| 2011/0250464 A1 | 10/2011 | Wilson et al. |
| 2011/0287956 A1 | 11/2011 | Iqbal et al. |
| 2011/0312529 A1* | 12/2011 | He ...................... C12Q 1/6874 506/9 |
| 2012/0041727 A1 | 2/2012 | Mishra et al. |
| 2012/0097539 A1 | 4/2012 | Qian et al. |
| 2012/0132886 A1 | 5/2012 | Peng et al. |
| 2012/0184047 A1 | 7/2012 | Jonsson et al. |
| 2012/0193237 A1 | 8/2012 | Afzali-Ardakani et al. |
| 2012/0199485 A1 | 8/2012 | Sauer et al. |
| 2012/0254715 A1 | 10/2012 | Schwartz et al. |
| 2012/0258445 A1* | 10/2012 | Kim .................... H01L 29/0673 435/5 |
| 2012/0298511 A1 | 11/2012 | Yamamoto |
| 2012/0322055 A1 | 12/2012 | Royyuru |
| 2013/0001082 A1 | 1/2013 | Afzali-Ardakani et al. |
| 2013/0092547 A1 | 4/2013 | Li et al. |

(56) References Cited

U.S. PATENT DOCUMENTS

| | | | |
|---|---|---|---|
| 2013/0109577 A1* | 5/2013 | Korlach | B82Y 15/00 |
| | | | 506/13 |
| 2013/0157271 A1 | 6/2013 | Coursey et al. | |
| 2013/0186758 A1 | 7/2013 | Saha et al. | |
| 2013/0240359 A1* | 9/2013 | Turner | G01N 27/44791 |
| | | | 204/601 |
| 2013/0264207 A1 | 10/2013 | Ju et al. | |
| 2013/0334047 A1 | 12/2013 | Jeong et al. | |
| 2014/0000105 A1 | 1/2014 | Bielick et al. | |
| 2014/0008225 A1 | 1/2014 | Jeon et al. | |
| 2014/0031995 A1 | 1/2014 | Kawai et al. | |
| 2014/0055150 A1 | 2/2014 | Kawai et al. | |
| 2014/0103945 A1 | 4/2014 | Eid et al. | |
| 2014/0183040 A1 | 7/2014 | Kawai et al. | |
| 2014/0202857 A1 | 7/2014 | Valbusa et al. | |
| 2014/0273186 A1 | 9/2014 | Oxenrider | |
| 2014/0300339 A1 | 10/2014 | Taniguchi et al. | |
| 2014/0302675 A1 | 10/2014 | Astier et al. | |
| 2014/0364324 A1 | 12/2014 | Turner et al. | |
| 2014/0374695 A1 | 12/2014 | Astier et al. | |
| 2015/0107996 A1 | 4/2015 | Chen | |
| 2015/0111759 A1 | 4/2015 | Ju et al. | |
| 2015/0132756 A1 | 5/2015 | Peter et al. | |
| 2015/0219593 A1 | 8/2015 | Kawai et al. | |
| 2015/0310228 A1 | 10/2015 | Benz et al. | |
| 2015/0323490 A1 | 11/2015 | Luan et al. | |
| 2015/0354001 A1* | 12/2015 | Porath | G01N 33/48721 |
| | | | 204/627 |
| 2016/0048690 A1 | 2/2016 | Tanishima et al. | |
| 2016/0049327 A1 | 2/2016 | Singh et al. | |
| 2016/0138101 A1 | 5/2016 | Taniguchi et al. | |
| 2016/0245789 A1 | 8/2016 | Ikeda et al. | |
| 2016/0245790 A1 | 8/2016 | Kawai et al. | |
| 2016/0320364 A1 | 11/2016 | Ikeda et al. | |
| 2016/0377591 A1 | 12/2016 | Kawai et al. | |
| 2017/0131237 A1 | 5/2017 | Ikeda | |
| 2017/0144158 A1 | 5/2017 | Taniguchi | |
| 2017/0146510 A1 | 5/2017 | Ikeda et al. | |
| 2017/0146511 A1 | 5/2017 | Taniguchi et al. | |
| 2017/0306396 A1 | 10/2017 | Kawai et al. | |
| 2018/0023132 A1 | 1/2018 | Kawai et al. | |
| 2018/0180567 A1* | 6/2018 | Li | B81B 7/02 |

FOREIGN PATENT DOCUMENTS

| | | |
|---|---|---|
| CN | 101920932 A | 12/2010 |
| CN | 102180440 A | 9/2011 |
| CN | 102687027 A | 9/2012 |
| CN | 102753708 A | 10/2012 |
| CN | 102914395 A | 2/2013 |
| CN | 103203256 A | 7/2013 |
| CN | 103502795 A | 1/2014 |
| CN | 104583767 A | 4/2015 |
| CN | 107683337 A | 2/2018 |
| EP | 1419112 A1 | 5/2004 |
| EP | 2573554 A1 | 3/2013 |
| EP | 3315461 A1 | 5/2018 |
| JP | 62-194673 A | 8/1987 |
| JP | S6437640 A | 2/1989 |
| JP | 04-302151 A | 10/1992 |
| JP | H04302151 A | 10/1992 |
| JP | H0774337 A | 3/1995 |
| JP | H10283230 A | 10/1998 |
| JP | 2003507026 A | 2/2003 |
| JP | 2003090815 A | 3/2003 |
| JP | 2003332555 A | 11/2003 |
| JP | 2003533676 A | 11/2003 |
| JP | 2004233356 A | 8/2004 |
| JP | 2004247203 A | 9/2004 |
| JP | 2004303162 A | 10/2004 |
| JP | 2005501234 A | 1/2005 |
| JP | 2005257687 A | 9/2005 |
| JP | 2006078491 A | 3/2006 |
| JP | 2006526777 A | 11/2006 |
| JP | 2007272212 A | 10/2007 |
| JP | 2008032529 A | 2/2008 |
| JP | 2008146538 A | 6/2008 |
| JP | 4128573 B2 | 7/2008 |
| JP | 2008186975 A | 8/2008 |
| JP | 2008536124 A | 9/2008 |
| JP | 4289938 B2 | 7/2009 |
| JP | 2009527817 A | 7/2009 |
| JP | 2009210272 A | 9/2009 |
| JP | 2009272432 A | 11/2009 |
| JP | 2010264207 A | 4/2010 |
| JP | 2010513853 A | 4/2010 |
| JP | 2010227735 A | 10/2010 |
| JP | 2011500025 A | 1/2011 |
| JP | 2011054631 A | 3/2011 |
| JP | 2011516050 A | 5/2011 |
| JP | 4719906 B2 | 7/2011 |
| JP | 2011163934 A | 8/2011 |
| JP | 2011211905 A | 10/2011 |
| JP | 2012110258 A | 6/2012 |
| JP | 2012118709 A | 6/2012 |
| JP | 2013036865 A | 2/2013 |
| JP | 2013090576 A | 5/2013 |
| JP | 2013518283 A | 5/2013 |
| JP | 2013519074 A | 5/2013 |
| JP | 2013215725 A | 10/2013 |
| JP | 2014074599 A | 4/2014 |
| JP | 2014173936 A | 9/2014 |
| JP | 2015059824 A | 3/2015 |
| JP | 2015077652 A | 4/2015 |
| KR | 1020140031559 | 3/2014 |
| TW | 200619614 A | 6/2006 |
| TW | 200637916 A | 11/2006 |
| TW | 200907068 A | 2/2009 |
| TW | 201013179 A | 4/2010 |
| TW | 201100796 A | 1/2011 |
| WO | 0113088 A1 | 2/2001 |
| WO | 0181896 A1 | 11/2001 |
| WO | WO-0181908 A1 | 11/2001 |
| WO | WO-03018484 A1 | 3/2003 |
| WO | WO-03042396 A2 | 5/2003 |
| WO | WO-03106693 A2 | 12/2003 |
| WO | WO-2007013370 A1 | 2/2007 |
| WO | WO-2008035787 A1 | 3/2008 |
| WO | WO-2008071982 A2 | 6/2008 |
| WO | WO-2008071982 A3 | 7/2008 |
| WO | WO-2008079169 A2 | 7/2008 |
| WO | WO-2009045472 A1 | 4/2009 |
| WO | WO-2009093019 A2 | 7/2009 |
| WO | WO-2009120642 A1 | 10/2009 |
| WO | WO-2009149362 A2 | 12/2009 |
| WO | WO-2010111605 A2 | 9/2010 |
| WO | WO-2010116595 A1 | 10/2010 |
| WO | WO-2010111605 A3 | 11/2010 |
| WO | WO-2011082419 A2 | 7/2011 |
| WO | 2011093940 A1 | 8/2011 |
| WO | WO-2011097171 A1 | 8/2011 |
| WO | WO-2011108540 A1 | 9/2011 |
| WO | WO-2012009578 A2 | 1/2012 |
| WO | WO-2012009578 A3 | 4/2012 |
| WO | WO-2012164679 A1 | 12/2012 |
| WO | WO-2012170560 A2 | 12/2012 |
| WO | WO-2013016486 A1 | 1/2013 |
| WO | WO-2013066456 A2 | 5/2013 |
| WO | WO-2013074546 A1 | 5/2013 |
| WO | WO-2013076943 A1 | 5/2013 |
| WO | WO-2013066456 A3 | 7/2013 |
| WO | WO-2013100949 A1 | 7/2013 |
| WO | WO-2013115185 A1 | 8/2013 |
| WO | WO-2013116509 A1 | 8/2013 |
| WO | WO-2013147208 A1 | 10/2013 |
| WO | WO-2014027580 A1 | 2/2014 |
| WO | WO-2014084931 A1 | 6/2014 |
| WO | WO-2015028885 A2 | 3/2015 |
| WO | WO-2015028886 A2 | 3/2015 |
| WO | WO-2015042200 A1 | 3/2015 |
| WO | WO-2015028885 A3 | 4/2015 |
| WO | WO-2015057870 A1 | 4/2015 |
| WO | WO-2015028886 A3 | 5/2015 |

(56) References Cited

FOREIGN PATENT DOCUMENTS

| | | |
|---|---|---|
| WO | WO-2015111760 A1 | 7/2015 |
| WO | WO-2015125920 A1 | 8/2015 |
| WO | WO-2015167019 A1 | 11/2015 |
| WO | WO-2015170782 A1 | 11/2015 |
| WO | WO-2015170783 A1 | 11/2015 |
| WO | WO-2015170784 A1 | 11/2015 |
| WO | WO-2016010975 A2 | 1/2016 |
| WO | WO-2016206593 A1 | 12/2016 |
| WO | WO-2017061129 A1 | 4/2017 |
| WO | WO-2017179581 A1 | 10/2017 |
| WO | WO-2017189930 A1 | 11/2017 |
| WO | WO-2018025887 A1 | 2/2018 |
| WO | WO-2019065904 A1 | 4/2019 |

OTHER PUBLICATIONS

Co-pending U.S. Appl. No. 16/709,568, filed Dec. 10, 2019.
Co-pending U.S. Appl. No. 16/826,523, filed Mar. 23, 2020.
Si et al. Effect of nanopore size on poly(dT)30 translocation through silicon nitride membrane. Science China Technological Sciences, vol. 56, No. 10, pp. 2398-2402 (Oct. 2013). doi: 10.1007/s11431-013-5330-2. Published online Aug. 21, 2013.
EP17790485.1 Extended European Search Report dated Dec. 5, 2019.
Ohshiro et al. Tunnel-Current based Single-Molecule Identification of DNA/RNA oligmer by using Nano-MCBJ. 2012 12th IEEE International Conference on Nanotechnology (IEEE-NANO), Birmingham, United Kingdom, (Aug. 20-23, 2012). 2 pages.
Tang et al. Sub-10-nm nanogap fabrication by silicidation. 2013 13th IEEE International Conference on Nanotechnology (IEEE-NANO 2013). (Aug. 5-8, 2013). 4 pages. DOI: 10.1109/NANO.2013.6720811.
Anima et al. Fabrications of insulator-protected nanometer-sized electrode gaps. Journal of Applied Physics 115:114310 (2014). 6 pages. doi: 10.1063/1.4869135.
Armbrust et al. Clearing the clouds away from the true potential and obstacles posed by this computing capability. Communications of the ACM 53(4):50-58 (Apr. 2010).
Axopatch 2008 Patch Clamp: Theory and Operation, Axon Instruments, Inc., Mar. 1999.
Bagci, et al. Recognizing nucelotides by cross-tunneling currents for DNA sequencing. Physical Review E, vol. 84, Issue No. 1, Article No. 011917 (internal pp. 1-4) (2011).
Brown, et al. Nucleotide-Surface Interactions in DNA-Modified Au-Nanoparticle Conjugates: Sequence Effects on Reactivity and Hybridization. J. Phys. Chem. C, 2008, 112 (20), pp. 7517-7521.
Carter, et al. Voltammetric studies of the interaction of metal chelates with DNA. 2. Tris-chelated complexes of cobalt (III) and iron (II) with 1, 10-phenanthroline and 2, 2'-bipyridine. Journal of the American Chemical Society 111.24 (1989): 8901-8911.
Chang, et al. Tunnelling readout of hydrogen-bonding-based recognition. Nature Nantechnology, vol. 4, May 2009, pp. 297-301.
Chen, et al., A novel nanofabrication technique for the array of Nanogap electrodes, Japanese Journal of Applied Physics, Japan Society of Applied physics, JP, 2006, 45(6):5531-5534.
Chen, et al., Probing Single DNA Molecule Transport Using Fabricated Nanopores, Nano Letters, 2004, 4(11):2293-2298.
Cheng, et al. Development of an electrochemical membrane-based nanobiosensor for ultrasensitive detection of dengue virus. Anal Chim Acta. May 6, 2012;725:74-80. doi: 10.1016/j.aca.2012.03.017. Epub Mar. 17, 2012.
Clarke, et al. Continuous base identification for single-molecule nanopore DNA sequencing. Nat Nanotechnol. Apr. 2009;4(4):265-70. doi: 10.1038/nnano.2009.12. Epub Feb. 22, 2009.
Co-pending U.S. Appl. No. 14/687,856, filed Apr. 15, 2015.
Co-pending U.S. Appl. No. 15/937,327, filed Mar. 27, 2018.
Co-pending U.S. Appl. No. 16/156,755, filed Oct. 10, 2018.
Co-pending U.S. Appl. No. 16/178,924, filed Nov. 2, 2018.
Co-pending U.S. Appl. No. 16/234,908, filed Dec. 28, 2018.

Dekker, et al. Solid-state nanopores. Nature Nanotechnology, vol. 2, Apr. 2007, pp. 209-215.
Ei-Ali, et al., Simulation and experimental validation of a SU-8 based PCR themorcycler chp with integrated heaters and temperature sensor, Sensors and Actuators A, 110, 2004, pp. 3-10.
Feng et al. "Nanopore-based Fourth-generation DNA Sequencing Technology" Genomics, Proteomics & Bioinformatics. 2015; 13(1):4-16, pp. 5, co12, para 3.
Fischbein, et al. Sub-10 nm Device Fabrication in a Transmission Electron Microscope. American Chemical Society, Nano Letters, 2007, vol. 7, No. 5, pp. 1329-1337.
Fologea, et al. Detecting Single Stranded DNA with a Solid State Nanopore. American Chemical Society, Nano Letters, 2005, vol. 5, No. 10, pp. 1905-1909.
Fuller et al. "Real-time single-molecule electronic DNA sequencing by synthesis using polymer-tagged nucleotides on a nanopore array" PNAS, Mar. 18, 2016 (Mar. 18, 2016); 113(19):5233-5238 (doi: 10.1073/pnas.1601782113) p. 5234, col. 1, para 1-3; p. 5235, col. 1, para 1; p. 5236, col. 1, para 1; Fig. 2.
Furuhashi et al. Denaturation of DNAs in a nanofluidic channel by micro-heating method. The 74th Annual Meeting of the Japan Society of Applied Physics Lecture Papers p. 12-295 (Aug. 2013).
Furuhashi et al. Denature of double-stranded DNAs by a microheating method. Proceedings of the 60th Spring Science Lecture Meeting of the Japan Society of Applied Physics, p. 12-356, (Mar. 2013).
Furuhashi, et al. High speed DNA denaturation using microheating devices. Appl. Phys. Lett., Jul. 11, 2013, 103, pp. 023112.
Garcia-Lekue et al. Plane-wave-based electron tunneling through Au nanojunctions: Numerical calculations. Physical Review B 82:035410 (2010). 9 pages.
Gierhart, et al. Nanopore with transverse nanoelectrodes for electrical characterization and sequencing of DNA. Sens Actuators B Chem. Jun. 16, 2008;132(2):593-600.
Giese, et al. Direct observation of hole transfer through DNA by hopping between adenine bases and by tunnelling. Nature. Jul. 19, 2001;412(6844):318-20.
Gonzalez, et al. Mass transport effect of mesoscopic domains in the amperometric response of an electroactive species: Modeling for its applications in biomolecule detection. Sensors and Actuators B: Chemical 144.2 (2010): 349-353.
Grib, et al. Distance-dependent coherent charge transport in DNA: crossover from tunneling to free propagation. Journal of Biophysical Chemistry, 1, 77-85. Aug. 2010.
Hashioka, et al, Metal nanogap devices fabricated by conventional photolithography and their application to deoxyribose nucleic acid analysis, Journal of Vacuum Science & Technology B: microelectronics; Materials, Processing and Phenomena, 2003, 21(6):2937-40.
He, et al. Controlling DNA translocation through gate modulation of nanopore wall surface charges. ACS Nano. Jul. 26, 2011;5(7):5509-18. doi: 10.1021/nn201883b. Epub Jun. 17, 2011.
He, et al. Gate manipulation of DNA capture into nanopores. ACS Nano. Oct. 25, 2011;5(10):8391-7. doi: 10.1021/nn203186c. Epub Sep. 26, 2011.
He, et al. Identification of DNA Basepairing via Tunnel-Current Decay. American Chemical Society, Nano Letters, 2007, vol. 7, No. 12, pp. 3854-3858.
He, et al. Thermophoretic manipulation of DNA translocation through nanopores. ACS Nano. Jan. 22, 2013;7(1):538-46. doi: 10.1021/nn304914j. Epub Dec. 10, 2012.
Healy et al. Fabrication and characterization of nanopores with insulated transverse nanoelectrodes for DNA sensing in salt solution. Electrophoresis 33(23) (Dec. 2012). doi: 10.1002/elps.201200350. 15 pages.
International Search Report and Written Opinion dated Aug. 7, 2017 for International Application No. PCT/US2017/029978.
Ivanov, et al. DNA tunneling detector embedded in a nanopore. Nano Lett. Jan. 12, 2011;11(1):279-85. doi: 10.1021/nl103873a. Epub Dec. 6, 2010.
Jortner, et al. Charge transfer and transport in DNA. PNAS 1998 95 (22) 12759-12765; doi:10.1073/pnas.95.22.12759.

(56) References Cited

OTHER PUBLICATIONS

Keyser, et al. Direct force measurements on DNA in a solid-state nanopore. Nature Physics, vol. 2, Jul. 2006, pp. 473-477.
Korol, et al. Thermopower of molecular junctions: Tunneling to hopping crossover in DNA. J Chem Phys. Dec. 14, 2016;145(22):224702.
Lagerqvist, et al. "Fast DNA Sequencing via Transverse Electronic Transport", American Chemical Society, Nano Letters, 2006, vol. 6, No. 4, pp. 779-782.
Lagerqvist, et al. Influence of the Environment and Probes on Rapid DNA Sequencing via Transverse Electronic Transport. Biophysical Journel, vol. 93, Oct. 2007, pp. 2384-2390.
Lee, et al. Surface charge study on pollen with a simple microelectrophoresis instrumentation setup. Biomedical Engineering and Sciences (IECBES), 2010 IEEE EMBS Conference on. Kuala Lumpur, Malaysia, Nov. 30-Oct. 2, 2010, pp. 364-368.
Lesser-Rojas, et al. Tandem array of nanoelectronic readers embedded coplanar to a fluidic nanochannel for correlated single biopolymer analysis. Biomicrofluidics. Jan. 10, 2014;8(1):016501. doi: 10.1063/1.4861435. eCollection 2014. With Supplementary Materials.
Li, et al. Ion-beam sculpting at nanometer length scales. Nature, vol. 412, Jul. 2001, pp. 166-169.
Li, et al. Thermoelectric effect and its dependence on molecular length and sequence in single DNA molecules. Nature Communications 7, Article No. 11294 (2016).
Liang, et al. Nanogap Detector Inside nanofluidic Channel for Fast Real-Time Label-Free DNA Analysis. American Chemical Society, Nano Letters 2008, vol. 8, No. 5, pp. 1472-1476.
Liu, C. et al. Engineering nanometre-scale coherence in soft matter. Nature Chemistry 2016, 8, 941-945.
Maleki, et al. A nanofluidic channel with embedded transverse nanoelectrodes. Nanotechnology, 20, (2009) 105302, pp. 1-6.
Mastrangelo, et al. The potential and challenges of nanopore sequencing. Nature Biotechnology. 26 (2008): 1146-1153.
Nadasan, et al. Design and fabrication of the microchannels for microfluidics applications. U.P.B. Sci. Bull., Series C, 2009, 71(4): pp. 125-134.
Nam, et al. Ionic field effect transistors with sub-10 nm multiple nanopores. Nano Lett. May 2009;9(5):2044-8. doi: 10.1021/nl900309s.
Ohshiro, et al. Single-molecule electrical random resequencing of DNA and RNA. Scientific Reports 2, Article No. 501 (Jul. 10, 2012) doi:10.1038/srep00501.
Ohshiro et al. Supplementary Information for Single-Molecule Electrical Random Resequencing of DNA and RNA. Scientific Reports 2, Article No. 501 (Jul. 10, 2012). 23 pages. doi:10.1038/srep00501.
Oshiro, et al. Detection of post-translational modifications in single peptides using electron tunnelling currents. Nature Nanotechnology, vol. 9, pp. 835-840 (e-pub. Sep. 14, 2014).
Oshiro, et al. Single-molecule electrical random resequencing of DNA and RNA. Scientific Reports, vol. 2, Article No. 501 (internal pp. 1-7) (e-pub. Jul. 10, 2012) See abstract: p. 2; figures 1-4; and tables 1-3.
PCT/US2017/029978 International Preliminary Report on Patentability dated Oct. 30, 2018.
Pedone, et al. Data Analysis of Translocation Events in Nanopore Experiments. American Chemical Society, Anal. Chem. 2009, 81, p. 9689.
Peng, et al. Reverse DNA translocation through a solid-state nanopore by magnetic tweezers. Nanotechnology. May 6, 2009;20(18):185101. doi: 10.1088/0957-4484/20/18/185101. Epub Apr. 14, 2009.
Qi. Modeling Electrical Transport Through Nucleic Acids. Thesis (Ph.D.) University of Washington, 2015.
Qiu, et al. Detecting ssDNA at single-nucleotide resolution by sub-2-nanometer pore in monoatomic graphene: A molecular dynamics study. Applied Physics Letters 100.8 (2012): 083106. 4 pages.
Renaud, et al. Between superexchange and hopping: an intermediate charge-transfer mechanism in poly(A)-poly(T) DNA hairpins. J. Am. Chem. Soc. 135, 3953-3963 (2013).

Renaud, N., et al. Deep-hole transfer leads to ultrafast charge migration in DNA hairpins. Nature Chem. Nature Chemistry 8, 1015-1021 (2016).
Rothberg, et al. An integrated semiconductor device enabling non-optical genome sequencing. Nature. 475 (2011): 348-352.
Ruitenbeek, et al. Adjustable nanofabricated atomic size contacts. Rev. Sci. Instrum. 67, 108 (1996).
Schreiber et al. "Error rates for nanopore discrimination among cytosine, methylcytosine, and hydroxymethylcytosine along individual DNA strands" PNAS, 2013; 11 0(47): 18910-18915, p. 18910, col. 2, para 3.
Simmons, et al. Generalized Formula for the Electric tunnele Effect between Similar Electrodes Separated by a Thin Insulating Film. J. Appl. Phys. 34, 1793 (1963).
Smith, et al. Electrophoretic distributions of human peripheral blood mononuclear white cells from normal subjects and from patients with acute lymphocytic leukemia. Proc Natl Acad Sci U S A. Jul. 1976;73(7):2388-91.
Tsutsui et al. Electrical Detection of Single-Methylcytosines in a DNA Oligomer. J Am Chem Soc 133(23): 9124-9128 (May 11, 2011). DOI: 10.1021/ja203839e.
Stijin Van Dorp, et al. Origin of the electrophoretic force on DNA in solid-state nanopores. Nature Physics, vol. 5, May 2009, pp. 347-351.
Stoddart, et al. Single-nucleotide discrimination in immobilized DNA oligonucleotides with a biological nanopore. PNAS, May 12, 2009, vol. 106, No. 19, pp. 7702-7707.
Storm, et al. Fabrication of solid-state nanopores with single-nanometere precision. Nature Materials, vol. 2, Aug. 2003, pp. 537-540.
Suga et al. Influence of electrode size on resistance switching effect in nanogap junctions, Applied Physics Letter, 2010, 97(7):73118, 4 pages. Epub Aug. 20, 2010.
Taniguchi, et al. Denryu de Ichi Enki Bunshi o Shikibetsu suru. Chemistry, 2011, vol. 66, No. 8, pp. 42-46.
Taniguchi, M. Ichibunshi Kaiseki Gijutsu ni yoru Jijisedai DNA Sequencer no Kaihatsu. Dai 69 Kai Hyomen Kagaku Kenkyukai Yoshishu. Mar. 9, 2011, pp. 23-26.
Trepagnier, et al. Controlling DNA Capture and Progagation through Artificial Nanopores. American Chemical Society, Nano Letters, 2007, vol. 7, No. 9, pp. 2824-2830.
Troisi, et al. Molecular signatures in the transport properties of molecular wire junctions: what makes a junction "molecular"? Small. Feb. 2006;2(2):172-81.
Tsutsui, et al. Fabrication of 0.5 nm electrode gaps using self-breaking technique. Applied Physics Letters 93, 163115 (2008); DOI: 10.1063/1.3006063.
Tsutsui, et al. Formation and self-breaking mechanism of stable atom-sized junctions. Nano Lett. Jan. 2008;8(1):345-9. Epub Dec. 21, 2007.
Tsutsui, et al., Formation and self-breaking mechanism of stable atom-sized junctions, Nano Letters, 2008, 8(1):345-349.
Tsutsui, et al. Identifying single nucleotides by tunnelling current. Nature Nanotechnology, Letters, Published Online: Mar. 21, 2010; DOI: 10.1038/NNANO.2010.42, pp. 1-5.
Tsutsui et al. Supplementary Information for Identifying Single Nucleotides by Tunneling Current. Nature Nanotechnology 5:286-290 (Mar. 21, 2010). doi: 10.1038/NNANO.2010.42.
Tsutsui et al. Supporting Information for Electrical Detection of Single-Methylcytosines in a DNA Oligomer. J Am Chem Soc 133(23): 9124-9128 (May 11, 2011). DOI: 10.1021/ja203839e.
Tsutsui, et al. Transverse electric field dragging of DNA in a nanochannel. Sci Rep. 2012;2:394. doi: 10.1038/srep00394. Epub May 3, 2012. 7 pages.
Tsutsui, et al. Transverse Field Effects on DNA-Sized Particle Dynamics. American Chemical Society, Nano Letters, 2009, vol. 9, No. 4, pp. 1659-1662.
Venkatesan, et al. Nanopore sensors for nucleic acid analysis. Nat Nanotechnol. Sep. 18, 2011;6(10):615-24. doi: 10.1038/nnano.2011.129.
Wang, et al. Mechanism of electron conduction in self-assembled alkanethiol monolayer devices. Phys. Rev. B 68, 035416—Published Jul. 17, 2003.

(56) References Cited

OTHER PUBLICATIONS

Woolley, et al. Capillary electrophoresis chips with integrated electrochemical detection . . . Analytical Chemistry 70.4 (1998): 684-688.
Xiang, et al. Intermediate tunnelling-hopping regime in DNA charge transport. Nature Chemistry 7, 221-226 (2015).
Xu, et al. Direct Conductance Measurement of Single DNA Molecules in Aqueous Solution. Nano Letters, 2004, 4 (6), pp. 1105-1108.
Yen, et al. Gate effects on DNA translocation through silicon dioxide nanopore. Rev Sci Instrum. Mar. 2012;83(3):034301. doi: 10.1063/1.3692746.
Zhang, et al. A flickering resonance mechanism for biological charge transfer. Proc. Natl Acad. Sci. USA 111, 10049-10054 (2014).
Zhao, et al. Single-strand DNA molecule translocation through nanoelectrode gaps. Nanotechnology. Oct. 24, 2007;18(42):424018. doi: 10.1088/0957-4484/18/42/424018. Epub Sep. 19, 2007. 7 pages.
Zhou, et al. Microfabrication of a mechanically controllable break junction in silicon. Appl. Phys. Lett. 67, 1160 (1995).
Zwolak, et al. Colloquium: Physical approaches to DNA sequencing and detection. Reviews of Modern Physics, vol. 80, Jan.-Mar. 2008, pp. 141-165.
Zwolak, et al. Electronic Signature of DNA Nucleotides via Transverse Transport. American Chemical Society, Nano Letters, 2005, vol. 5, No. 3, pp. 421-424.
Co-pending U.S. Appl. No. 16/266,363, filed Feb. 4, 2019.
Kaji, et al., "Separation of long DNA molecules by quartz nanopillar chips under a direct current electric field",Anal. Chem., 76(1): pp. 15-22, Jan. 1, 2004.
Taniguchi, et al., "Fabrication of the gating nanopore device",Applied Physics Letters 95:123701 (2009). 4 pages. DOI: https://doi.org/10.1063/1.3236769, 2009.
Huang, et al., "Identifying single bases in a DNA oligiomer with electron tunnelling",Nat Nanotechnol. Dec. 2010; 5(12):868-73. doi:10.1038/nnano.2010.213. Epub, Nov. 14, 2010.
Taniguchi, et al., "Development of Single-Molecule Bio-Nanodevices for Medical Applications",The Imaging Society of Japan, vol. 52, No. 1, pp. 51-60, Feb. 10, 2013.

* cited by examiner

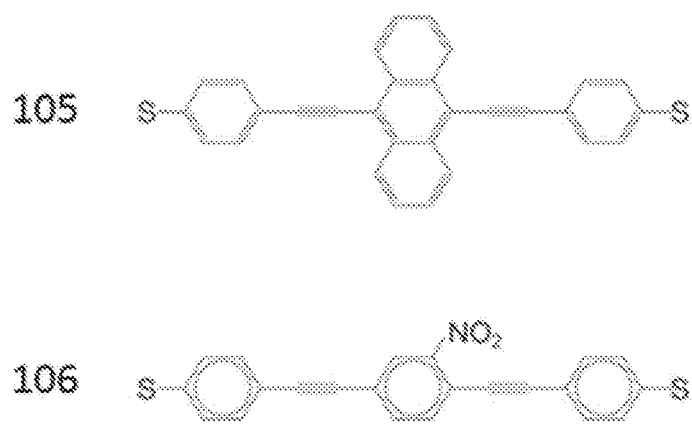
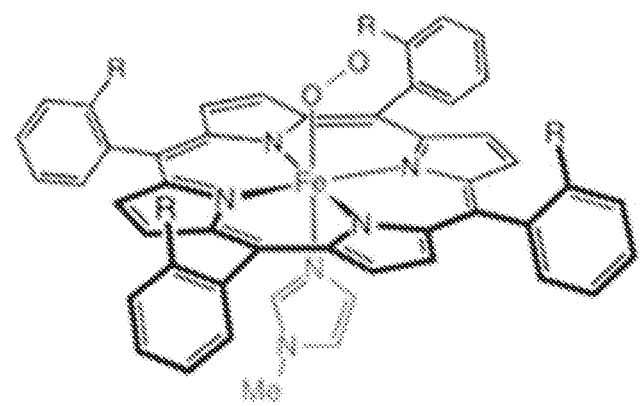
Fig. 1C
Fig. 1D

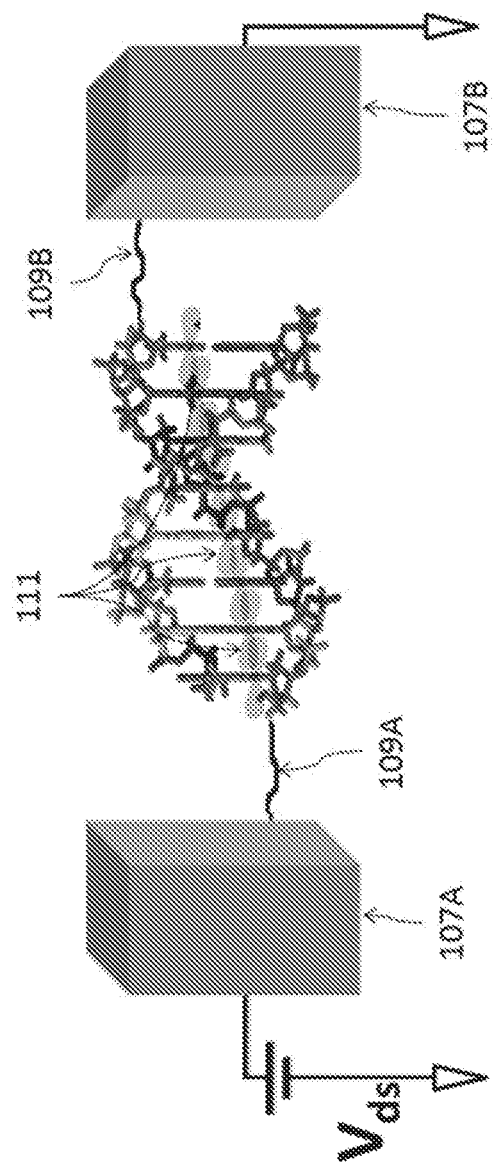

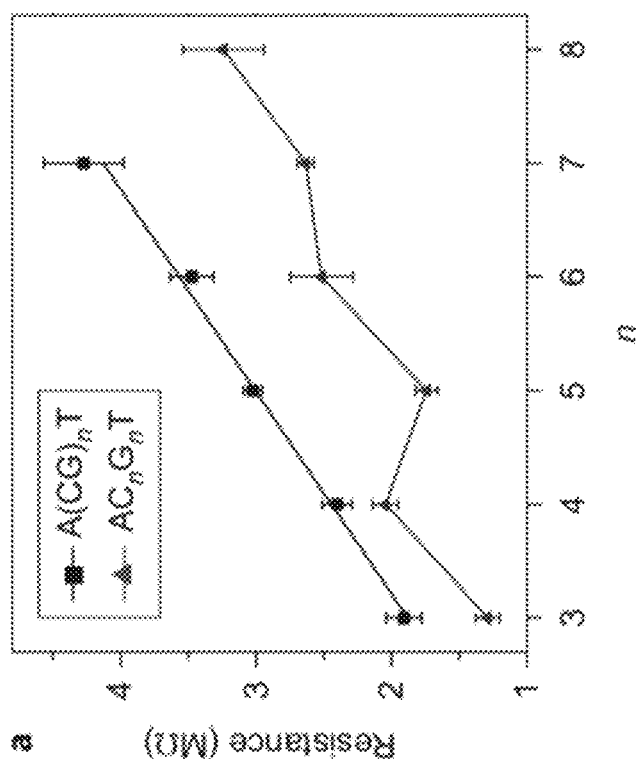
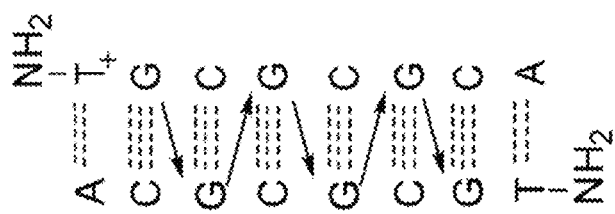
Fig. 1G
Fig. 1H

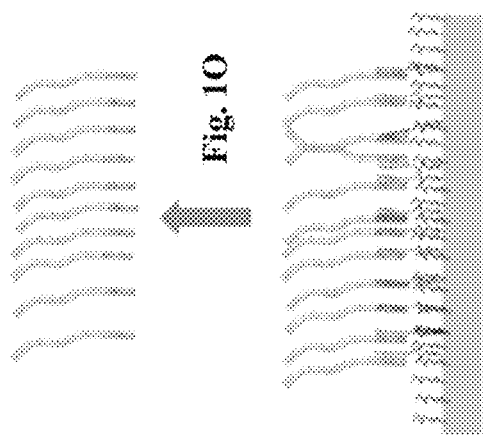
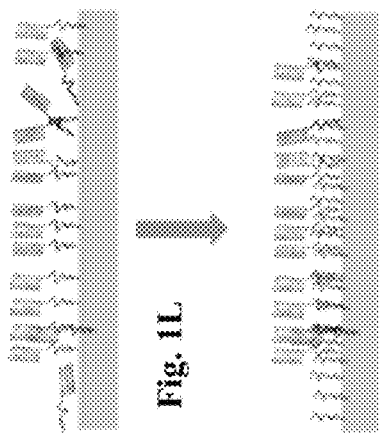

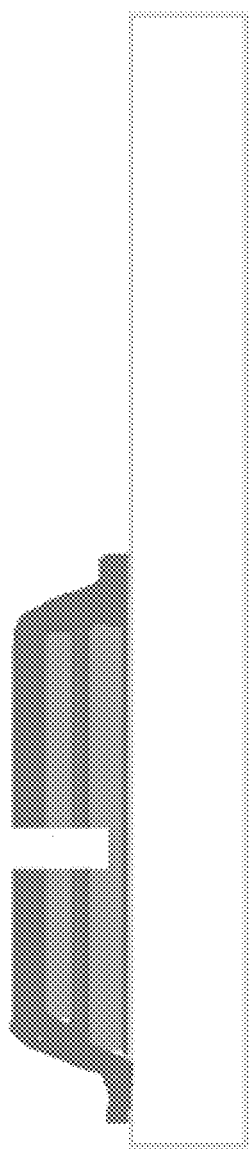

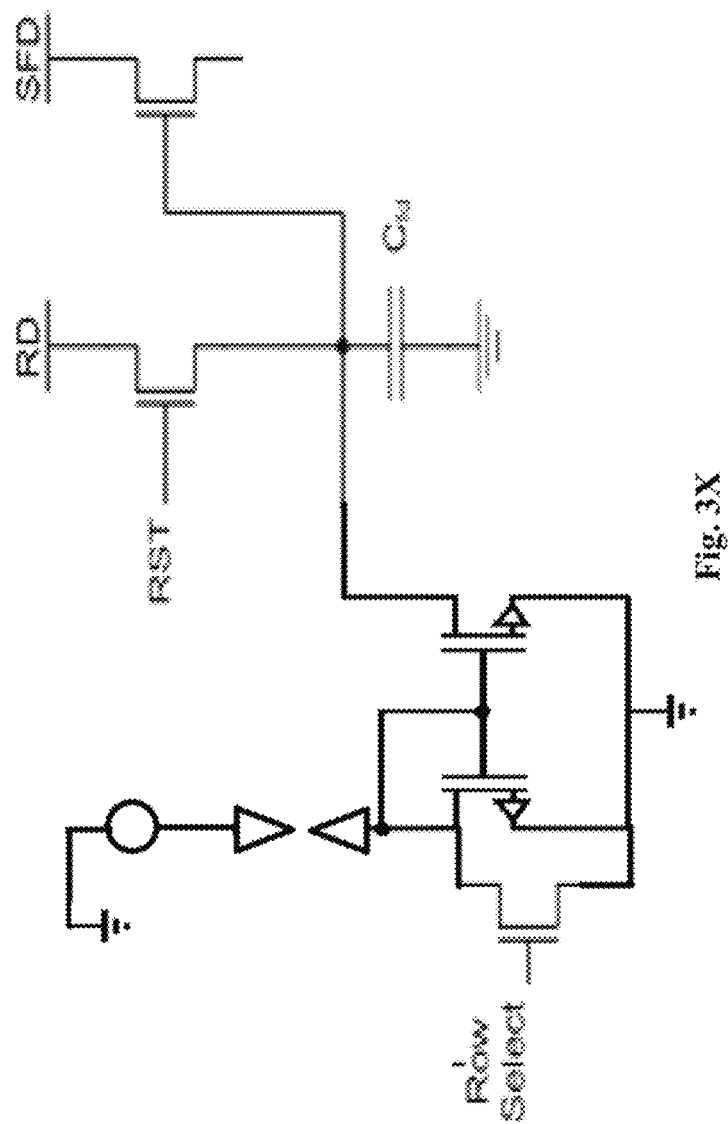

SYSTEMS AND METHODS FOR MEASUREMENT AND SEQUENCING OF BIO-MOLECULES

CROSS-REFERENCE

This application is a continuation of International Patent Application No. PCT/US2017/029978, filed Apr. 27, 2017, which claims the benefit of U.S. Provisional Patent Application No. 62/328,527, filed Apr. 27, 2016, U.S. Provisional Patent Application No. 62/385,782, filed Sep. 9, 2016, and U.S. Provisional Patent Application No. 62/359,648, filed Jul. 7, 2016, each of which is entirely incorporated herein by reference.

BACKGROUND

New research continues to increase our understanding of genetic information and raise challenges about how to detect nucleic acid sequence and epigenetics. There are challenges in terms of fast data measurement and extraction. Some methods rely on optical signal measurement through modified bases. Some methods rely on ion current measurement and certain modifications to the native bases. However, these methods may lack speed and throughput, and may have errors such as phase errors, phototoxicity, deletion and repeated base errors, and homopolymer count errors. In addition, many methods may require clonal or whole genome amplification, resulting in amplification bias. No system can concurrently directly determine DNA and RNA sequences and epigenetics.

SUMMARY

Recognized herein is a need for high-throughput and fast measurement of native DNA bases with high accuracy and low costs.

Some aspects of the present disclosure provide polynucleotide sequencing methods by measuring tunneling current from bases with tunneling labels with high throughput in a massively parallel system on a chip.

Some aspects of the present disclosure provide systems for sequencing polynucleotide molecules such DNA. The systems may comprise two electrodes disposed on a substrate separated by a non-conductive gap. The electrodes and the gap may be configured to accommodate a polymerase in the vicinity of the two electrodes. The electrodes and the gap may be further configured for detecting an electron or hole tunneling current when at least one nucleotide comprising a tunneling label is incorporated into or bound next to a single stranded portion of a polynucleotide in the presence of the polymerase.

Some aspects of the present disclosure provide an apparatus comprising at least two electrodes disposed on a substrate separated by a non-conductive gap. The electrodes and the gap may be configured to accommodate a polymerase in the vicinity of the two electrodes. The electrodes and the gap may be adapted for detecting an electron or hole tunneling current during incorporation and or binding of a nucleotide into a polynucleotide in the presence of the polymerase. The nucleotide may comprise a tunneling label. The nucleotide may be incorporated into or bound to a single stranded portion of the polynucleotide.

In some embodiments, kinetics of the binding and release of nucleotides may be monitored. The binding kinetics may be used to provide information about e.g., the epigenetic makeup of a target strand of nucleic acids.

Some aspects of the present disclosure provide a method for determining biological information in an oligo. The method may comprise placing the oligo between two electrodes on a substrate, applying a bias voltage between the two electrodes, measuring a current between the two electrodes, calculating the conductance or resistance of the oligo, and determining the biological information based on the conductance or resistance.

An aspect of the present disclosure provides a method comprising: (a) using a polymerase adjacent to two electrodes on a substrate to bind a nucleobase having a tunneling label attached thereto, said nucleobase complementary to an interrogated base of a sample nucleic acid; (b) measuring a current signal comprising a combination of at least one tunneling current and at least one hopping current between the two electrodes caused by localization of the tunneling label to the two electrodes; and (c) identifying a matching nucleobase on a single stranded portion of the sample nucleic acid based at least in part on the measured current signal.

An aspect of present disclosure provides a method for sequencing a nucleic acid molecule, comprising: (a) providing a substrate comprising at least two electrodes separated by a gap, wherein the substrate is solid; (b) directing to a gap a reaction mixture comprising one or more labeled nucleotide types, and reagents necessary for a nucleic acid amplification reaction; (c) subjecting at least a portion of a reaction mixture to a nucleic acid amplification reaction under conditions that are sufficient to yield an amplification product of a nucleic acid molecule, which amplification product may include at least one of one or more labeled nucleotide types; (d) using an at least two electrodes to detect an at least one electrical signal from an amplification product, which may be as a result of an amplification product being extended in a gap, or may be as an amplification product is directed through a gap, wherein an at least one electrical signal comprises tunneling current; and (e) identifying a nucleic acid sequence of a nucleic acid molecule or a portion thereof based on an electrical signal detected in (d).

In some embodiments, an at least one electrical signal is at least in part non-Faradaic current. In some embodiments, an at least one signal comprises a plurality of signals. In some embodiments, an at least one signal may comprise tunneling current, or tunneling current and hopping current. In some embodiments, one or more labeled nucleotide types may be labeled with one or more molecules and or other moieties that may facilitate a formation of a tunneling current and or a hopping current. In some embodiments, a one or more molecules and or other moieties may comprise a conductive portion. In some embodiments, a conductive portion permits an electrical current passing therethrough when a one or more molecules or other moieties is subjected to a potential. In some embodiments, an electrical current may be direct current (DC). In some embodiments, an electrical current may be alternating current (AC). In some embodiments, a molecule may comprise a tunneling label. In some embodiments, a tunneling label may be bound to a base portion of a given nucleotide of one or more labeled nucleotide types. In some embodiments, a tunneling label may be bound to a phosphate chain of a given nucleotide type of one or more labeled nucleotide types. In some embodiments, a tunneling label may be reversibly bound to a given nucleotide type of one or more labeled nucleotide types. In some embodiments, one or more labeled nucleotide types comprise at least two different types of nucleotide types or modifications thereof. In some embodiments, each type of an at least two types of nucleotides or modifications thereof may be labeled with a different tunneling label. In some embodiments, a tunneling label may comprise a zwitterionic compound. In some embodiments, a tunneling label may comprise a nucleic acid sequence. In some embodiments, a nucleic acid sequence may comprise greater than or equal to about 10 bases. In some embodiments, a nucleic acid sequence may comprise a double stranded portion and a single stranded portion. In some embodiments, at least one of the one or more labeled nucleotide types may comprise a terminator. In some embodiments, a method further comprises removing a terminator from a given labeled nucleotide incorporated into an amplification product after detection of an electrical signal. In some embodiments, a tunneling label may be bound to a terminator. In some embodiments, a tunneling label may be reversibly bound to a terminator. In some embodiments, an at least one electrical signal may be detected at a signal-to-noise ratio greater than or equal to about 100-to-1. In some embodiments, a signal-to-noise ratio may be greater than or equal to about 1000-to-1. In some embodiments, an at least one electrical signal may be detected in real-time. In some embodiments, reagents may comprise an enzyme. In some embodiments, an enzyme may have nucleic acid polymerase activity. In some embodiments, an enzyme may be a polymerase. In some embodiments, a polymerase may comprise a deoxyribonucleic acid (DNA) polymerase. In some embodiments, a polymerase may comprise a ribonucleic acid (RNA) polymerase. In some embodiments, a method may further comprise disposing a polymerase in fluidic environment of an at least two electrodes. In some embodiments, a method may further comprise disposing a polymerase on a dielectric between an at least two electrodes. In some embodiments, a method may further comprise disposing a polymerase on a surface of at least one of an at least two electrodes. In some embodiments, a method may further comprise disposing a polymerase on top of an at least two electrodes. In some embodiments, a polymerase may facilitate incorporation of an at least one of one or more labeled nucleotide types into an amplification product. In some embodiments, reagents may comprise ions. In some embodiments, ions may comprise cations. In some embodiments, cations may comprise $Ca^{2+}$, $Mg^{2+}$, $Mn^{2+}$, $Zn^{2+}$ or combinations thereof. In some embodiments, cations may comprise catalytic cations, non-catalytic cations, or combinations thereof. In some embodiments, a gap width or spacing may be greater than or equal to about 1 nanometer (nm). In some embodiments, a gap width or spacing may be less than or equal to about 20 nm. In some embodiments, a gap width or spacing may be greater than 20 nm. In some embodiments, a flow channel may have a depth greater than or equal to about 100 nm. In some embodiments, a sensor with at least two electrodes may have a first portion and a second portion adjoining and underneath a first portion. In some embodiments, a first portion may have a first width, and a second portion may have a second width smaller than a first width. In some embodiments, a sensor may have a cross sectional shape of an inverted cone. In some embodiments, a nucleic acid amplification reaction may comprise a polymerase chain reaction (PCR). In some embodiments, a nucleic acid amplification reaction may comprise a strand displacement amplification (SDA) reaction. In some embodiments, a nucleic acid amplification reaction may comprise a nucleic acid extension reaction. In some embodiments, a method may further comprise, repeating a set of steps which may include binding, detecting and incorporating of labeled nucleotides as described in steps (c)-(e) until identifying at least about 5 bases of a sample nucleic acid molecule or a portion thereof. In some embodiments, a substrate may comprise a plurality of electrode pairs, each pair configured to identify nucleic acid sequences of a different sample nucleic acid molecule or a portion thereof. In some embodiments, a nucleic acid sequence of a nucleic acid molecule or a portion thereof may be identified with an accuracy of at least about 90%. In some embodiments, an accuracy may be at least about 95%. In some embodiments, a nucleic acid sequence of a nucleic acid molecule or a portion thereof may be identified with an accuracy of at least about 90% over a span of at least about 100 contiguous nucleic acid bases of a nucleic acid molecule.

Another aspect of the present disclosure provides a system for sequencing a nucleic acid molecule comprising: a substrate comprising at least two electrodes separated by a gap as part of a flow channel, wherein a substrate may be solid; and a computer processor operatively coupled to a substrate and programmed to: (a) direct to a electrode pair sensors or a set of electrode pair sensors a reaction mixture comprising one or more labeled nucleotide types, and reagents necessary for a nucleic acid amplification reaction; (b) subject at least a portion of a reaction mixture to a nucleic acid amplification reaction under conditions that are sufficient to yield an amplification product of a nucleic acid molecule, which amplification product may include at least one of one or more labeled nucleotide types; (c) use an at least two electrodes to detect an at least one electrical signal from a bound labeled nucleotide or an amplification product as an amplification product may be generated and or directed through a gap, wherein an at least one electrical signal may comprise tunneling current; and (d) identify a nucleic acid sequence of a nucleic acid molecule or a portion thereof based on an electrical signal detected in (c).

In some embodiments, an at least one electrical signal may be at least partly a non-Faradaic current. In some embodiments, an at least one signal may comprises a plurality of signals. In some embodiments, an at least one electrical signal may comprise tunneling current. In some embodiments, one or more labeled nucleotide types may be labeled with a molecule that may facilitate a formation of a tunneling current and hopping current. In some embodiments, a label may comprise a conductive portion. In some embodiments, a conductive portion may permit an electrical current passing therethrough when a label may be subjected to a potential. In some embodiments, an electrical current may be direct current (DC). In some embodiments, an electrical current may be alternating current (AC).

In some embodiments, an electrical current may be a combination of direct current and alternating current. In some embodiments, a molecule may comprise a tunneling label. In some embodiments, a tunneling label may be bound to a base portion of a given nucleotide type of one or more labeled nucleotide types. In some embodiments, a tunneling label may be bound to a phosphate chain of a given nucleotide of one or more labeled nucleotide types. In some embodiments, a tunneling label may be bound to any position of a ribose or other backbone molecule of a given nucleotide of a set of one or more labeled nucleotides types. In some embodiments, a tunneling label may be reversibly bound to a given nucleotide of one or more labeled nucleotide types. In some embodiments, one or more labeled nucleotide types may comprise at least two different types of nucleotides or modifications thereof. In some embodiments, each type of an at least two types of nucleotides or modifications thereof may be labeled with a different tunneling label.

In some embodiments, a tunneling label may comprise a zwitterionic compound. In some embodiments, a tunneling label may comprise a nucleic acid sequence. In some embodiments, a nucleic acid sequence may comprise greater than or equal to about 10 bases. In some embodiments, a nucleic acid sequence may comprise a double stranded portion and a single stranded portion. In some embodiments, one or more labeled nucleotide types may comprise a terminator. In some embodiments, a tunneling label may be bound to a terminator.

In some embodiments, a tunneling label may be reversibly bound to a terminator. In some embodiments, an at least one electrical signal may be detected with a signal-to-noise ratio greater than or equal to about 100-to-1. In some embodiments, a signal-to-noise ratio may be greater than or equal to about 1000-to-1. In some embodiments, an at least one electrical signal may be detected in real-time. In some embodiments, a reagent may comprise an enzyme. In some embodiments, an enzyme may have nucleic acid polymerase activity. In some embodiments, an enzyme may be a polymerase. In some embodiments, a polymerase may comprise DNA polymerase. In some embodiments, a polymerase may comprise RNA polymerase. In some embodiments, a polymerase may be disposed in a fluidic environment of an at least two electrodes. In some embodiments, a polymerase may be disposed on a dielectric between an at least two electrodes. In some embodiments, a polymerase may be disposed on a surface of at least one of an at least two electrodes. In some embodiments, a polymerase may be disposed on top of an at least two electrodes.

In some embodiments, a polymerase may facilitate binding and or incorporation of an at least one of one or more labeled nucleotide types into an amplification product. In some embodiments, reagent may comprise ions. In some embodiments, ions may comprise cations. In some embodiments, cations may comprise $Ca^{2+}$, $Mg^2$, $Mn^{2+}$, $Zn^{2+}$ or combinations thereof. In some embodiments, cations may comprise catalytic cations, non-catalytic cations, or combinations thereof. In some embodiments, a gap may be greater than or equal to about 1 nanometer (nm). In some embodiments, a gap width or spacing may be less than or equal to about 20 nm. In some embodiments, a flow channel has a depth greater than or equal to about 100 nm.

In some embodiments, a sensor comprising an electrode pair may have a first portion and a second portion adjoining and underneath a first portion. In some embodiments, a first portion may have a first width, and a second portion may have a second width smaller than a first width. In some embodiments, a polymerase may have a size that is greater than the second width and smaller than the first width. In some embodiments, a sensor comprising an electrode pair may have a cross sectional shape of an inverted cone.

In some embodiments, a nucleic acid amplification reaction may comprise a polymerase chain reaction (PCR). In some embodiments, a nucleic acid amplification reaction may comprise a strand displacement amplification (SDA) reaction. In some embodiments, a nucleic acid amplification reaction may comprise a primer extension reaction.

In some embodiments, a nucleic acid sequence of a nucleic acid molecule or a portion thereof may be identified with an accuracy of at least about 90%. In some embodiments, an accuracy may be at least about 95%. In some embodiments, a nucleic acid sequence of a nucleic acid molecule or a portion thereof may be identified with an accuracy of at least about 90% over a span of at least about 100 contiguous nucleic acid bases of a nucleic acid molecule.

In some embodiments, a system may further comprise a chip comprising a sensor, a sensor having a substrate. In some embodiments, an at least two electrodes may be coupled to an electric circuit. In some embodiments, a sensor may coupled to an electric circuit that processes an at least one electric signal. In some embodiments, a chip may comprise a plurality of sensors, each comprising an individual pair of electrodes. In some embodiments, a chip may comprise at least about 10,000, 100,000, 1,000,000, 10,000,000, 100,000,000, 1,000,000,000, 10,000,000,000 or more than 10,000,000,000 sensors. In some embodiments, each of a plurality of sensors or plurality of sets of sensors may be independently addressable.

Another aspect of the present disclosure provides a non-transitory computer-readable medium comprising machine-executable code that, upon execution by one or more computer processors, implements a method for sequencing a nucleic acid molecule, the method comprising: (a) providing a substrate comprising at least two electrodes separated by a gap within a flow channel area, wherein a substrate may be solid; (b) directing to an at least two electrodes a reaction mixture comprising one or more labeled nucleotide types, and reagents necessary for a nucleic acid amplification reaction; (c) subjecting at least a portion of the reaction mixture to a nucleic acid amplification reaction under conditions that are sufficient to yield an amplification product of a nucleic acid molecule, which amplification product may include at least one of one or more labeled nucleotide types; (d) using an at least two electrodes to detect at least one electrical signal during a step of an amplification process wherein a labeled nucleotide may be bound or an amplification product may be bound in a gap or may be directed through a gap, wherein an at least one electrical signal may comprise a tunneling current; and (e) identifying a nucleic acid sequence of a nucleic acid molecule or a portion thereof based on an electrical signal detected in (d).

Another aspect of the present disclosure provides a method for sequencing a nucleic acid molecule, comprising: (a) providing a substrate comprising at least two electrodes separated by a gap with an area of a a flow channel, wherein a substrate may be solid; (b) directing through a gap between electrodes a nucleic acid molecule comprising one or more labeled nucleotide types; (c) using an at least two electrodes to detect at least one electrical signal from a nucleic acid molecule, including a one or more labeled nucleotide types, wherein an at least one electrical signal may comprise tunneling current; and (d) identifying a nucleic acid sequence of a nucleic acid molecule or a portion thereof based on an electrical signal detected in (c).

In some embodiments, an at least one electrical signal may be a non-Faradaic current. In some embodiments, an at least one signal may comprise a plurality of signals. In some embodiments, an at least one electrical signal may comprise a tunneling current. In some embodiments, one or more labeled nucleotide types may be labeled with a molecule and or other moiety that may facilitate a formation of a tunneling current or tunneling and hopping current. In some embodiments, a molecule and or other moiety may comprise a tunneling label. In some embodiments, a tunneling label may be bound to a base portion of a given nucleotide of one or more labeled nucleotide types. In some embodiments, a tunneling label may be bound to a phosphate chain of a given nucleotide type of one or more labeled nucleotide types. In some embodiments, a tunneling label may be reversibly bound to a given nucleotide type of one or more labeled nucleotide types. In some embodiments, one or more labeled nucleotide types may comprise at least two different types of nucleotides or modifications thereof. In some embodiments, each type of the at least two types of nucleotides or modifications thereof may be labeled with a different tunneling label. In some embodiments, one or more labeled nucleotide types may comprise a terminator. In some embodiments, a tunneling label may be bound to a terminator. In some embodiments, a tunneling label may be reversibly bound to a terminator.

Another aspect of the present disclosure provides a system for sequencing a nucleic acid molecule, comprising: a substrate comprising at least two electrodes separated by a gap within a flow channel area, wherein a substrate may be solid; and a computer processor operatively coupled to a substrate and programmed to: (a) direct through the flow channel to the at least two electrodes a nucleic acid molecule comprising one or more labeled nucleotide types; (b) use an at least two electrodes to detect an at least one electrical signal from a nucleic acid molecule, including one or more labeled nucleotide types, wherein an at least one electrical signal may comprise tunneling current; and (c) identify a nucleic acid sequence of a nucleic acid molecule or a portion thereof based on an electrical signal detected in (b).

In some embodiments, an at least one electrical signal may be at least partly non-Faradaic current. In some embodiments, an at least one signal may comprise a plurality of signals. In some embodiments, an at least one electrical signal may comprise tunneling current. In some embodiments, one or more labeled nucleotide types may be labeled with a molecule that facilitates a formation of a tunneling current or tunneling and hopping current. In some embodiments, a molecule may comprise a tunneling label. In some embodiments, a tunneling label may be bound to a base portion of a given nucleotide type of one or more labeled nucleotide types. In some embodiments, a tunneling label may be bound to a phosphate chain of a given nucleotide type of one or more labeled nucleotide types. In some embodiments, a tunneling label may be reversibly bound to a given nucleotide of one or more labeled nucleotide types. In some embodiments, one or more labeled nucleotide types may comprise at least two different types of nucleotide types or modifications thereof. In some embodiments, each type of the at least two types of nucleotides or modifications thereof may be labeled with a different tunneling label. In some embodiments, one or more labeled nucleotide types may comprise a terminator. In some embodiments, a tunneling label may be bound to a terminator. In some embodiments, a tunneling label may be reversibly bound to a terminator.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1B, 1C, and 1D show several different polymeric molecules with tunneling conductance;

FIG. 1E shows a DNA strand and a tunneling current therethrough;

FIG. 1G shows the conductance as a function of the length of different GC containing DNA sequences;

FIG. 1H shows a strand hopping tunneling conductance path;

FIG. 1I shows a method for synthesizing a label;

FIGS. 1L, 1M, 1O and 1N show a method for forming and measuring a density of a SAM formed on an electrode;

FIGS. 3L-3N show another method for forming a nanogap sensor;

FIG. 3X schematically depicts a simplified schematic for an integrating sensor cell circuit;

DETAILED DESCRIPTION

Figure 1A:
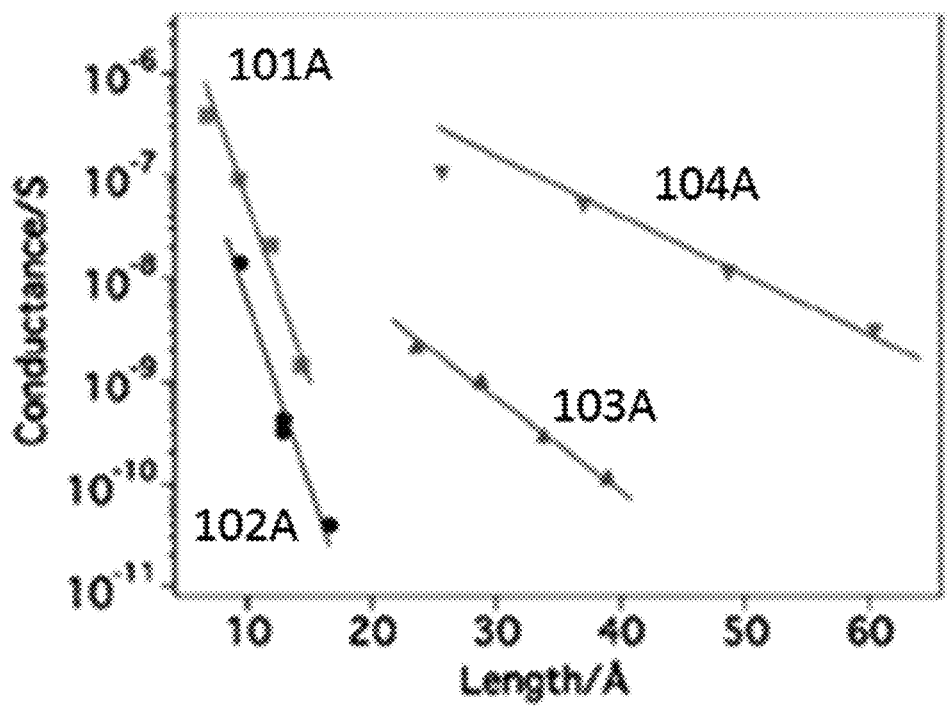
FIG. 1A shows a graph of polymer tunneling conductance.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides systems and methods relating to sequencing biomolecules, for example, polynucleotide sequencing, as well as the use of tunneling labels for other purposes, including detection and quantitation of biomolecules. Example systems and or methods may include tunneling current measurement from polynucleotide synthesis within a gap formed by a pair of electrodes and identifying tunneling signals associated with each base.

The term "gap," as used herein, generally refers to a volume, space, pore, channel or passage formed or otherwise provided in a material, or between electrodes. The material may be a solid state material, such as a substrate, or may be formed of different layers formed on a substrate. A gap may be disposed adjacent or in proximity to a sensing circuit or an electrode coupled to a sensing circuit. In some examples, a gap may have a characteristic width or diameter on the order of 0.1 nanometers (nm) to about 1,000 nm. A gap having a width on the order of nanometers may be referred to as a "nano-gap" (also "nano-gap" herein). In some situations, a nano-gap may have a width or spacing that may be from about 0.1 nanometers (nm) to about 50 nm, 0.5 nm to 30 nm, or 0.5 nm to 10 nm, 0.5 nm to 5 nm, or 0.5 nm to 2 nm, 5 to 30 nm, 10 nm to 20 nm, 5 nm to 20 nm, 15 nm to 25 nm, or no greater than about 2 nm, 1 nm, 0.9 nm, 0.8 nm, 0.7 nm, 0.6 nm, or 0.5 nm. In some cases, a nano-gap has a width that is at least about 0.5 nm, 0.6 nm, 0.7 nm, 0.8 nm, 0.9 nm, 1 nm, 2 nm, 3 nm, 4 nm, 5 nm, 7.5 nm, 10 nm, 15 nm, 20 nm, 30 nm or more than 30 nm. In some cases, a width or spacing of a nano-gap can be more than a diameter of a biomolecule used in a sequencing reaction, or may be less than the diameter of a sample biomolecule or a subunit (e.g., monomer) of a sample biomolecule.

The term "biomolecule" or "biopolymer," as used herein, generally refers to any biological material that can be interrogated as a function of electrical parameter(s) (e.g., electrical current, voltage, differential impedance, tunneling current, tunneling and or hopping current, resistance, capacitance, and or conductance) across a nano-gap electrode. A biomolecule may be a nucleic acid molecule, protein, or carbohydrate. A biomolecule may include one or more subunits, such as nucleotides or amino acids.

The term "nucleic acid," as used herein, generally refers to a molecule comprising one or more nucleic acid subunits. A nucleic acid may include one or more subunits selected from adenosine (A), cytosine (C), guanine (G), thymine (T) and uracil (U), abasic bases, or variants thereof, including, e.g., any naturally occurring or non-naturally occurring (e.g., modified or engineered), epigenetically modified bases, which may be coupled with deoxyriboses ribosese, PNAs (Protein Nucleic Acids), L-DNA, locked nucleic acids, or any other standard or nonstandard polymeric backbone. A nucleotide may include A, C, G, T or U, or variants thereof. A nucleotide may include any subunit that may be incorporated into a growing nucleic acid strand. A nucleotide may include any subunit which may bind to but not be incorporated into a growing nucleic acid strand. Such subunit may be an A, C, G, T, or U, or any other subunit that is specific to one or more complementary A, C, G, T or U, or complementary to a purine (i.e., A or G, or variant thereof) or a pyrimidine (i.e., C, T or U, or variant thereof). A subunit may enable individual nucleic acid bases or groups of bases (e.g., AA, TA, AT, GC, CG, CT, TC, GT, TG, AC, CA, or uracil-counterparts thereof) to be resolved. In some examples, a nucleic acid is deoxyribonucleic acid (DNA) or ribonucleic acid (RNA), or derivatives thereof. A nucleic acid may be single-stranded or double stranded, or partly single stranded and partly double stranded, and may have multiple single stranded portions, and may have multiple double stranded portions.

The term "protein," as used herein, generally refers to a biological molecule, or macromolecule, having one or more amino acid monomers, subunits or residues, or may refer to a complex of macromolecules wherein each may have one or more amino acid monomers, subunits or residues. A protein containing 50 or fewer amino acids, for example, may be referred to as a "peptide." Amino acid monomers may be selected from any naturally occurring and or synthesized amino acid monomer, such as, for example, 20, 21, or 22 naturally occurring amino acids. In some cases, 20 amino acids are encoded in the genetic code of a subject. Some proteins may include amino acids selected from about 500 naturally and non-naturally occurring amino acids. In some situations, a protein can include one or more amino acids selected from isoleucine, leucine, lysine, methionine, phenylalanine, threonine, tryptophan and valine, arginine, histidine, alanine, asparagine, aspartic acid, cysteine, glutamine, glutamic acid, glycine, proline, serine and tyrosine.

The term "adjacent" or "adjacent to" as used herein, includes 'next to', 'adjoining', 'in contact with', and 'in proximity to'. In some instances, adjacent to components are separated from one another by one or more intervening layers. For example, the one or more intervening layers can have a thickness less than about 10 micrometers ("microns"), 1 micron, 500 nanometers ("nm"), 100 nm, 50 nm, 10 nm, 1 nm, or less. In an example, a first layer is adjacent to a second layer when the first layer is in direct contact with the second layer. In another example, a first layer is adjacent to a second layer when the first layer is separated from the second layer by a third layer.

The term "tunneling," as used herein, generally refers to a movement of a particle, such as an electron, through a potential barrier which the particle does not have sufficient energy to overcome. This may be in contrast to standard conductance, wherein a particle may have sufficient energy to overcome any energy barriers.

a moiety (such as a The term "tunneling label," as used herein, generally refers to a moiety (such as a compound, a molecule, a particle, and combinations thereof) which may facilitate tunneling of electrons or holes within or through the moiety, or between one or more electrodes and the moiety. In some cases, tunneling may be measured as a tunneling and or hopping current.

The term "tunneling current," as used herein, generally refers to a current signal associated with tunneling of electrons or holes between two electrodes with a voltage (e.g., a bias voltage) applied thereto. The tunneling may be into, out of, through a tunneling label, or any combination thereof. In some cases, tunneling may be combined with portions of a conduction path wherein hopping may occur.

The term "synchronous chemistry method," as used herein, generally refers to a method wherein a cycle time is determinate. A synchronous chemistry method may need only a single measurement, as a time for an appropriate measurement may be known, and multiple measurements may not be needed to insure that an appropriate measurement is made.

The term "asynchronous chemistry method," as used herein, generally refers to a method wherein a cycle time is indeterminate, and may vary. An asynchronous chemistry method may particularly have need for multiple measurements, as it is not possible to determine when a measurement may need to be performed, so in order to insure that a desired measurement may be made, a number of measurements over a period of time may be necessary.

The term "stuck end," as used herein, may comprise a nucleic acid sequence, which may be a part of a SAM, and may be at least partly single stranded, such that it may bind or hybridize to a complementary or at least partly complementary nucleic acid, which may comprise a portion of a tunneling label, which may be at least partly single stranded in a region which may be complementary to a stuck end.

The term "sticky end," as used herein, generally refers to a nucleic acid sequence which may comprise a portion of a tunneling label, which may be at least partly single stranded in a region which may be complementary to a stuck end, and may thus bind or hybridize thereto.

The term "backfill," as used herein, generally refers to a part of a SAM which is nominally bioinert, and thus may not bind or interact with nucleic acids such as sample nucleic acids, nucleic acids which may comprise a portion of a label, nucleotides, proteins including enzymes, or other biomolecules, and may be bound as a part of a SAM to prevent interaction between biomolecules and a surface to which a SAM may be bound.

The term "skip read method," as used herein, generally refers to a sequencing method wherein a synchronous chemistry method may be utilized for a number of cycles and then suspended, an asynchronous chemistry method may thence be utilized for a period of time and then suspended, and then a synchronous chemistry method may be utilized for a number of cycles. The time during which the asynchronous chemistry method is utilized may be considered to be a "skip period". Measurements may not be made during a period of time utilizing an asynchronous chemistry.

The term "physical blocker," as used herein, generally refers to a first moiety bound to second moiety, wherein the first moiety is a moiety used as a part of a measurement process, and the second moiety is of a size such that first moieties may be separated apart from each other as a function of the size of a second moiety. A physical blocker may be used to allow individual localization of first moieties with respect to sensors, or may be used to space first moieties at a relatively regular spacing which may be larger than a spacing at which a first moiety might otherwise be spaced in the absence of second moieties. A second moiety may thus be considered to be a physical blocker.

The term "interrogated base," as used herein, generally refers to a base which may be a first base which does not have a complementary base incorporated as a part of an extended primer, and which would be complementary to a next base which would be incorporated by a polymerase or other enzyme. A base being incorporated may thus be one base in the 5' direction from a last base which has a complementary base which is a part of an extended primer, and which may further be bound at an active site of an enzyme such as a polymerase.

Quantum tunneling devices, when used for direct measurement of nucleotides for sequencing polynucleotides, can pose a few issues.

Another possible issue in single-molecule sequencing is device production, finding a way to manufacture a massively parallel sequencer with millions or more of devices on a chip. This may pose great technical and technological challenges for nano-devices. This however, may be necessary, for instance, for the purpose of whole genome single-molecule sequencing.

For example, a fluorescent molecule may create perhaps ~6000 photons, but only a small percentage (~10%) of the photons may be converted to electrons. In some cases, background induced noise means many fluorescent molecules need to be used to get adequate signal to noise ratio (S/N). Even with many fluorescent molecules the dye concentration may be low and a very high irradiance (photons/sec/unit area) may be required, often resulting in expensive laser illumination systems.

pH detection may also require a large number of molecules to generate a signal. Existing systems may need more than 100,000 molecules to get an adequate signal to noise ratio.

Tunneling Labels

As provided herein, a tunneling label may be a compound through which a tunneling current may provide a large number of electrons from a single polymer molecule with a low background level. For example, in 1 second, 1 nA of current may generate 6.2 M electrons. In the presence of a background of 5 pA, this may result in a shot noise limit S/N level of >1000:1.

In some cases, a tunneling label may provide a currents corresponding to conductances of less than 10-11, 10-11 to 10-10, 10-10 to 10-9, 10-9 to 10-8, or 10-8 to 10-7 or more Siemens. Thus with nominal bias potentials such as less than 10 mV, 10 mV to 100 mV, 100 mV to 250 mV, or greater than 250 mV, significant currents may be created such that shot noise, may be considered to be insignificant in many systems.

Figure 1B:
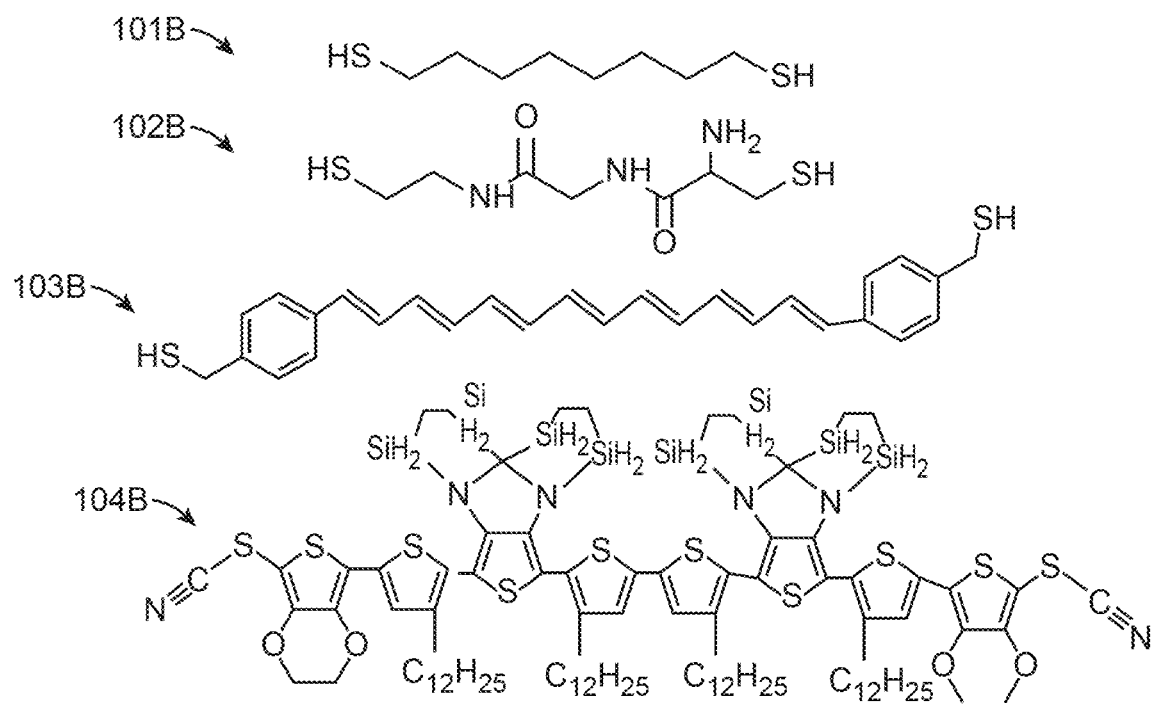

A tunneling label may conduct as a result from e.g., coherent or incoherent tunneling, incoherent thermally induced hopping, or combinations thereof. In contrast, a more standard conductive path does not involve the use of tunneling, whether coherent or incoherent. In some cases, a tunneling path may have a resistance of the formula $R=R0\, e^{(\beta L)}$, where L is the length of the tunneling path through which an electron, hole or current may pass and $\beta$ may be a constant dependent upon the molecule, and the conditions such as hydration of the molecule; examples of molecules with such tunneling paths are shown in FIGS. 1A and 1B. In some cases, a conductive path through a tunneling label may at least in part be from a hopping current. The portion of the path where hopping occurs may have a resistance of the formula $R=R0+\alpha L=R0+\alpha_\infty L e^{(Ea/kT)}$, where L is the length of the tunneling path through which an electron or current may pass, Ea is the activation energy, k is Boltzmann constant, and T is the temperature. Such currents may result from several relatively small movements through a tunneling label of an electron or hole, thereby forming a current through a longer portion of a tunneling label. The hopping current portions may or may not be thermally dependant. The tunneling current portions may or may not be temperature dependant. In some cases, both tunneling, which may be either coherent or incoherent, and hopping may occur through a single portion of a tunneling label.

In some cases, tunneling may occur as a result of $\pi$ electron orbitals or stacked $\pi$ electron orbitals. For example, tunneling may be aided as a result of the presence of overlapping $\pi$ electron orbitals, as occurs with double stranded DNA. Other locations wherein overlapping electron orbitals may occur in a manner useful for tunneling include benzene rings and other similar structures, for example where such structures may form sp2 hybridized orbitals, or pz orbitals.

As shown in FIG. 1E, a tunneling current may pass between two electrodes 107A and 107B, and may tunnel past or through linkers 109A and 109B, and may tunnel or hop through stacked $\pi$ electron orbitals of bases, resulting in current passage along the length of a nucleic acid polymer through $\pi$ orbitals 111. The sharing of electrons can influence the energy levels of electron orbitals, for example, highest energy occupied molecular orbital (HOMO) levels may be increased as a result of such sharing, which may allow better matching between the energy levels of the shared orbitals and the energy levels of electrodes, thus allowing higher conductance and current levels.

Figure 1F:
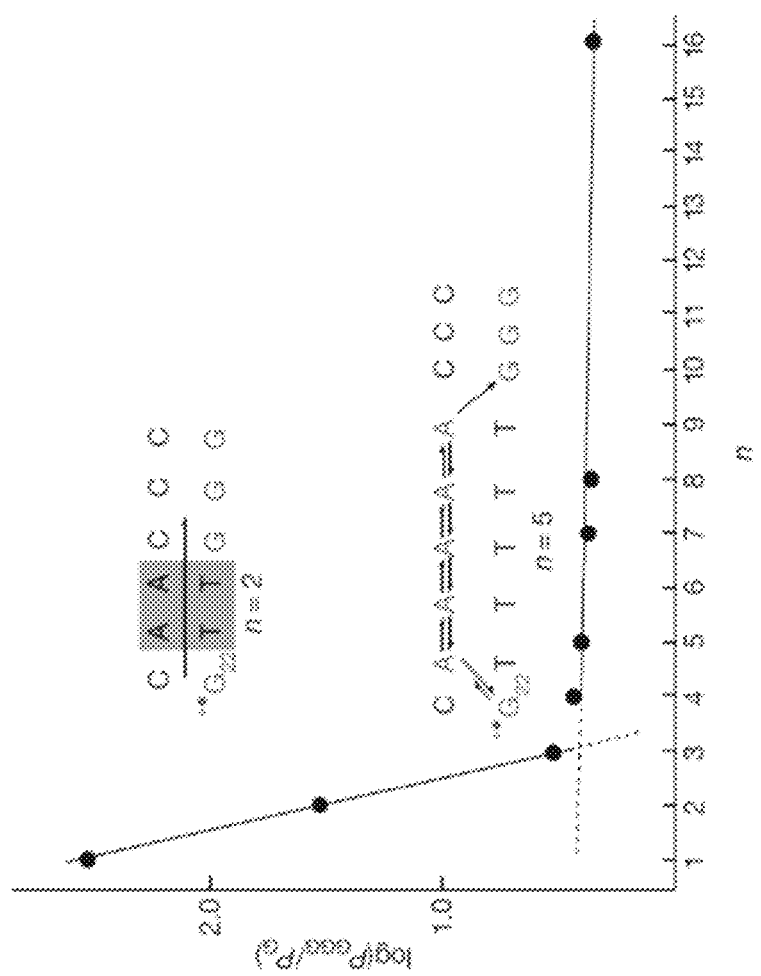
FIG. 1F shows the conductance as a function of the length of a homopolymer containing DNA sequence.
Figure 11:
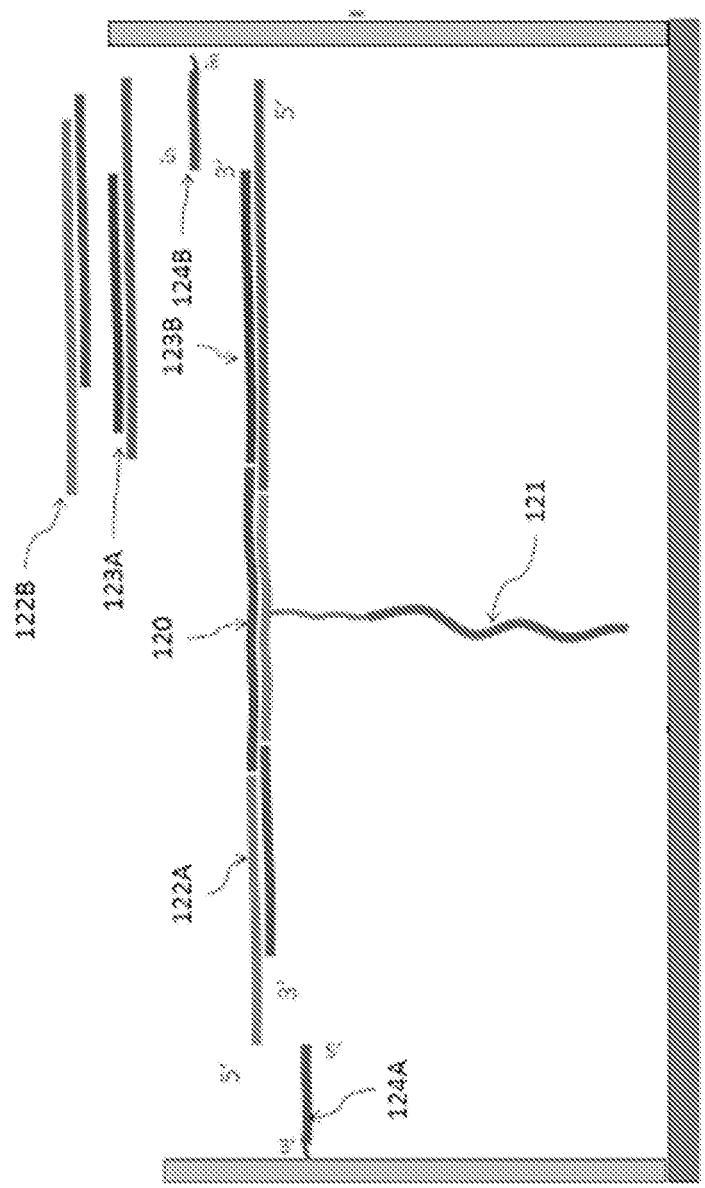

In some cases, a length of a tunneling label may be such that instead of primarily tunneling through a tunneling label, primarily hopping may occur through a tunneling label; some examples of this may be in homopolymer nucleic acids, particularly G and A bases which may have better π orbital overlap. Such a transition may result in a change in conductance from having primarily an inverse exponential function to having primarily an inverse linear function. Such a transition may occur in homopolymer A base pairs when a length of an A homopolymer sequence reaches about three base pairs as shown in FIG. 1F and as described by Griese et. al. in Nature 2001, 412 318, which is included by reference in its entirety. Similarly, a GC repeat sequence may have a primarily hopping conduction as a function of increased numbers of GC pairs of base pairs as shown in FIG. 1G and as described by Xiang et. al. in Nature Chemistry 2015 7 221 which is included by reference in its entirety, wherein the X axis is the number of GC base pairs, filled in squares are GC repeats, triangles are repeat homopolymers of Gs and Cs, and the Y axis is Mohms. FIG. 1H shows the path of conductance through a GC repeat sequence.

In some cases, a tunneling label may comprise polymers, such as oligomers. Non-limiting examples of the polymers may include oligothiophenes, oligophenyleneimines, combinations of electron donors and electron acceptors such as tetrathiafulvalene and pyromellitic diimide respectively, carbon nanoribbons, carotenoids, alkanes, tolanes, oligopeptides, oligoporphyrines, perylene tetracarboxylic diimides, fullerenes, carbon nanotubes, single walled nanotubes, graphene nanoribbons, different types of nucleic acids, duplex nucleic acids, triplex nucleic acids, or quadruplex nucleic acids, or combinations (e.g., a series combination, a parallel combination, or a series parallel combination thus forming a chimera) thereof.

In some embodiments, a tunneling label may have symmetrical or asymmetric conductance, depending upon e.g., orientation of at least a portion of the label. In some cases, the symmetries or asymmetries in conductance may be utilized to determine the orientation of a label.

The type or configuration of a tunneling label can significantly affect the conductance of the tunneling label. For example, as shown in FIG. 1A, the lengths (in Angstroms) of different types of polymers are depicted corresponding to the conductance (in Siemens) thereof and the structures of potential tunneling labels are shown in FIGS. 1B and 1C, wherein 101A shows various lengths and associated conductances of alkanes, and 101B shows the structure of alkane; 102A similarly shows various lengths and associated conductances of oligopeptides, and 102B shows the structure of an example oligopeptide; 103A similarly shows various lengths and associated conductances of carotenoid polymers, and 103B shows the structure of an example carotenoid polymers; 104A similarly shows various lengths and associated conductances of oligothiophenes, and 104B shows the structure of an example oligothiophene. Shown in FIG. 1C are example chemical structures of 9,10-di(2'-(para-acetylmercaptophenyl)ethinyl)-anthracene 105 which may have symmetric conductance, and 2,5-di(2'-(para-acetylmercaptophenyl)ethinyl)-4-nitro-acety-aniline 106 which may have asymmetric conductance. In some cases, any molecule used as a part of a single molecule or organic transistor may be suitable for use as at least a part of a tunneling label.

In some cases, a metal may be bound to a portion of a polymer, such as is the case for a porphyrin as shown in FIG. 1D, wherein the chemical structure for a tetraphenylporphorin is depicted. Other chelating molecules such as heme and ferrocene may be utilized to bind metal ions, such that one or more metal ions may comprise a portion of a tunneling label.

In some cases, a tunneling label may comprise a metal, such as a metal nanoparticle, nanobead, nanorod, or any other shape of a metal. In some cases, polymers such as nucleic acids may be bound to a nanobead, and the nucleic acid polymer may be at least partially complementary to a nucleic acid which may be bound to the electrodes of a sensor, such that the nucleic acids may hybridize, binding the nanobead to the electrodes of the sensor. In some cases, a metal nanoparticle may be bound using a sandwich assay, wherein a target nucleic acid may be at least partially complementary to corresponding nucleic acids bound to at least one electrode and to the metal nanoparticle, thus binding the metal nanoparticle and providing a tunneling and or hopping pathway between conductors with free electrons. In some cases, a nucleic acid strand may be metalized using a technique such as that described by Baigl et al. in WO2008/035787, which is hereby incorporated by reference in its entirety. In some cases, such a metalization treatment may be applied to a double stranded portion of a nucleic acid which may comprise a portion of a tunneling label, while single stranded portions, which may be at the ends of a nucleic acid, allowing binding via hybridization of a tunneling label. In some cases, only portions of a label may be metalized, using e.g., stoichiometric methods. In some cases, a label may comprise oligos and some of the oligos may be metalized. The remaining portions of the label may comprise oligos, or other conductive polymers or metal particles, and may be bound using ligation, click chemistry, or other covalent or noncovalent binding techniques.

In some cases, an oligo may comprise a portion of a label. An oligo may be formed using various oligonucleotide synthesis methods. In some examples, oligonucleotide synthesis may be difficult with long G homopolymers or oligos with high GC content. In such cases, an oligo may be formed using a combination of oligo synthesis and ligation method, allowing higher yields than might be possible when utilizing only oligonucleotide synthesis techniques.

A tunneling label may comprise polymers. The polymers may be bound to a metal particle comprised in the label using any appropriate binding mechanism, such as via thiol, disulfide, amine, diamine, or any other appropriate binding moiety. Polymers may be any type of polymer which may aid in providing a tunneling and or hopping conductance path. Polymers may comprise nucleic acid molecules (e.g. polymers). Nucleic acid molecules may be complementary and or partially complementary to one or more nucleic acid molecules (e.g., polymers) which may be associated with (e.g., bound to) electrodes. This may allow for higher tunneling currents than would occur without hybridization binding between the nucleic acid molecules.

In some cases, multiple binding moieties, and or moieties which do not bind may be bound to a metal such as a metal nanoparticle, nanobead, nanorod, or other shape of metal.

In some cases, labels associated with nucleobases may utilize different labels for different base types as a function of sequence and or length of a particular nucleic acid polymer tunneling label compound. A tunneling current associated with a particular tunneling label compound may decrease with increasing length and AT content in DNA. In some cases, a GC rich sequence may be utilized. A GC rich sequence may have a varied order of G and C bases, such that different orders of tunneling and or hopping may be utilized by electrons or holes which may pass through a tunneling label compound(s). In some cases, an AT rich sequence may be used. In other embodiments, a mixture of AT rich and GC rich sections may be used.

In some cases, a label may be made at least in part of a G quadruplex. For example, ends of a G homopolymer may not be G homopolymer, and thus may not bind in a tetrameric manner, and may be available for binding to a SAM which may comprise a DNA sequence complementary to a portion of a G quadruplex which does not bind in a tetrameric manner, and which may be bound to an electrode.

In some cases, one or more mismatches, or missing bases may be utilized within a tunneling label. Mismatches or missing bases may be utilized in a region where a tunneling label may binds to a self-assembled monolayer (SAM). In some cases, mismatches or missing bases may be within at least a portion of a tunneling label where a tunneling label may be double stranded before any interaction with a SAM. In some cases, one or more abasic bases, or non-natural nucleobases may be utilized in a manner similar to a base mismatch. In some cases, one or more of abasic, non-natural bases, naturally occurring nonstandard bases such as methylated C bases, methylated A bases, or any other type of naturally occurring or synthetic nucleobase, and modifications thereof may be utilized.

In some cases, a modified base may comprise at least in part a modified adenine. The modified adenine may have a substitution at the 7th position from a nitrogen to a C—H group, thus forming a 7-deazaadenine. Base pairing of an adenine modified in this manner may not be affected, and an associated tunneling current may be increased (potentially to almost same current level as for guanine). In some cases, a guanine nucleobase may be modified in a similar manner. A modified guanine may potentially increase a tunneling current from a natural guanine tunneling current, and may be able to achieve a much higher tunneling current with modified-GC rich tunneling label compounds.

A tunneling label (e.g., a tunneling label compound) may comprise double stranded nucleic acids, single stranded nucleic acids, or a combination thereof. In some examples, a tunneling label comprises partially double stranded and partially single stranded nucleic acids, wherein the nucleic acid strand may have two "sticky ends" wherein a sticky end may comprise either a 3' or 5' ends or both single stranded sections of the nucleic acids extending past a double stranded region of a label, wherein both strands of a complementary pair may extend past the complementary section. In other embodiments a tunneling compound may have a single longer strand which extends past both ends of a shorter double stranded section such that the single longer strand may interact with self assembled monolayers on both electrodes of an electrode pair.

In some cases, locked nucleic acids (LNA) and or peptide nucleic acid (PNA) may be utilized as a part of a tunneling label so as to enable shorter complementary SAMs which may have less binding to any target ssDNA. In some cases, nucleic acids which comprise complementary portions of SAMs and tunneling labels may comprise at least in part left hand helix DNA (L-DNA), such that hybridization may occur between the SAMs and the tunneling label compounds, while the SAMs may not bind to a target ssDNA strand due to opposite helix rotation. In some cases, a combination of locked DNA and L-DNA may be utilized to prevent binding of target ssDNA, while enabling short complementary regions on the SAM and the tunneling label compound.

In some cases, a dendrimer may be used as a label, and or as a stuck end. A dendrimeric structure may provide a number of simultaneous alternative pathways, allowing a single dendrimeric structure to effectively mitigate variations which might result from differences in crystal structure of electrodes and variations in currents which might result thereby. Diverse properties of dendrimers may result in a versatile tunneling/hopping label that may bind to a SAM in many ways and via many sites. A dendrimeric structure may comprise the same or different sequences of nucleic acids. In some cases, at least a portion (e.g., at least about 1%, 5%, 10%, 15%, 20%, 25%, 30%, 35%, 40%, 45%, 50%, 55%, 60%, 65%, 70%, 75%, 805, 85%, 90%, 95%, or more) of a dendrimer comprise the same or a similar sequence of nucleic acids. In some cases, at least a portion (e.g., at least about 1%, 5%, 10%, 15%, 20%, 25%, 30%, 35%, 40%, 45%, 50%, 55%, 60%, 65%, 70%, 75%, 805, 85%, 90%, 95%, or more) of a dendrimer have different sequences.

In some cases, the same dendrimer moiety may be used as label for all nucleotide bases. In some cases, a fluid containing different nucleotide base may be brought into a flow cell such that interaction with polymerases may bind the nucleotides as a subcycle within a sequencing cycle. Different base containing fluids may be brought into a flow cell such that interaction with polymerases may bind the nucleotides sequentially with same dendrimer label for each cycle. In some cases, after a subcycle, a nucleotide base containing fluid may be removed, and a wash buffer may be introduced to separate different types of nucleobases, and a different nucleotide base containing fluid comprising the same type of dendrimeric label may be brought into the flow cell so as to enable interaction with polymerases may bind labeled nucleobases. Sample nucleic acid sequence may thus be determined from patterns of nucleotide bindings detected via tunneling/hopping currents through the dendrimer caused by a bias voltage.

In some cases, a single label or dendrimeric structure with multiple labels may also comprise multiple nucleotides bound to the single structure. In some cases, the multiple nucleotides may be a same type of nucleobase; in other cases different nucleotides may comprise different types of nucleobases. In further cases the dendrimeric structure may comprise a single type of label; in other cases, the dendrimeric structure may comprise different types of labels. In some cases, wherein a number of different binding moieties may be desired, such as when testing a number of different types of nonstandard or epigenetically modified nucleobases, a dendrimeric structure may be identified by the combination of different labels which may be bound thereto as an identification code.

In some cases, a label and or SAM used to hybridize to or bind a tunneling label so as to increase a tunneling current through a tunneling label may comprise natural unmodified nucleobases. In some cases, modified bases (e.g., naturally occurring bases, or non-naturally occurring bases) are utilized. In some cases, the backbone may comprise a naturally occurring phosphate backbone with ribose. In some cases, non-naturally occurring modifications, such as sulfur modifications, or any other modifications may be utilized, including removing charge associated with the backbone, by for example, utilizing a PNA instead of a ribose, or by replacing the OH group on the phosphates with an uncharged group. Any other backbone modification, such as those used for aptamers, such as xeno nucleic acid (XNA) backbones, L-DNA, locked DNA, or A form DNA may also be utilized.

In some cases, in order to change the conductance of a label, different solvent conditions may be utilized. For example, a label which may have a B form when in a completely or largely aqueous solvent, may take on an A form upon change of solvent conditions. For example, adding an alcohol, such as ethanol or isopropanol may result in a change of the label to a shorter more compact structure, wherein the bases may not be primarily perpendicular to each other, but may instead be slightly offset. In such a B form, a conductance associated with a label sequence may be higher than the situation where the label sequence is in an A form, particularly when the label sequence does not have a primarily regular sequence, such as GCGC, or homopolymer AAAA. In some cases, a label which is in a form modified from a B form may have a higher level of hopping than the case where the label sequence is in a B form. While in a primarily B form, conductance may occur through the label in a primarily tunneling manner, and in a non B form, such as an A form, a label conductance may occur primarily through a hopping manner. In some cases, a label may be in a Z form. Differences between different forms may be characterized in several ways, including e.g., the diameter of a helix (20 angstroms for standard B form, 23 angstroms for A form, and 18 angstroms for Z form), the rise per base pair (3.32 angstroms for standard B form, 2.3 angstroms for A form, and 3.8 angstroms for Z form), the number of base pairs per revolution or turn (10.5 base pairs for standard B form, 11 base pairs for A form, and 12 base pairs for Z form), and a variety of other characteristics. A polymer may be described as being primarily in one form when one or more of the different characteristics are less than or equal to about 50%, 40%, 30%, 20%, 10%, 5%, 1%, or less of the difference between the different forms for the particular characteristic. For example, a nucleic acid strand under a particular solvent condition may be considered to be in a primarily B form when the rise per base pair is greater than 2.81 angstroms, and less than 3.56 angstroms, thus being greater than half the difference between A form and B form, less than half the difference between Z form and B form.

In some cases, ribonucleotides may be utilized. The ribonucleotides may largely take on an A form. The ribonucleotides may permit higher conductivities for label sequences which may be variable, potentially significantly variable, while permitting an A form for the label while in an aqueous or primarily aqueous solvent.

In some cases, in order to allow for more uniform and higher conductance associated with tighter and or more uniform binding of hybridized labels and SAMs and or intra label binding, modified bases may be utilized. The modified bases may have a stronger or weaker binding. Modified bases may be utilized in a pattern as a part of the "stuck ends" of the SAM, and or the "sticky ends" of the label, and or of bases at the ends of portions of labels and or stuck ends which may be double stranded portions, so that fraying may occur less often than nominally uniform binding, and conductance may be maintained at a higher average value until denaturation occurs.

In some cases, a portion or portions of a tunneling label may comprise a triplex or quadruplex form of nucleobase polymers, such as is naturally formed by having four three-mer homopolymer guanine regions in relatively close proximity to each other in a single strand, whereby Hoogsteen base pairing binds the guanine bases into a quadruplex, and may do so more stably than a standard duplex binding. Such a complex may comprise a single strand, two strands, three strands, or four strands. A quadruplex complex may have a higher conductivity than a natural duplex, as a result of the additional pi binding.

In other cases, 7-deazaguanine bases may be utilized to prevent undesired or inadvertent quadruplex formation. In cases where quadruplex formation may be undesirable, 7-deazaadenine bases may be utilized, wherein a tunneling conductivity of 7-deazaadenine bases may be much higher than a conductivity of standard adenine bases, and may also serve to prevent Hoogsteen binding that might otherwise occur between guanine bases.

In some cases, modified bases may be used as a part of a tunneling label and or a nucleobases set used to determine a sample base and or a modification to a sample base. Non-limiting examples of modified bases include 5-methylcytosine, N6-methyladenosine, N3-methyladenosine, N7-methylguanosine, 5-hydroxymethylcytosine, pseudouridine, thiouridine, isoguanosine, isocytosine, dihydrouridine, queuosine, wyosine, inosine, triazole, diaminopurine, ß-D-glucopyranosyloxymethyluracil, 8-oxoguanosine, or 2'-O-methyl adenosine, 2'-O-methyl cytidine, 2'-O-methyl guanosine, or 2'-O-methyl uridine, any of the known 140 epigenetic RNA modifications, or combinations thereof.

In some cases, an oligo used to hybridize to an oligo bound to an enzyme or polymerase may have a longer length, or a tighter binding, for example, as a result of using PNA or other uncharged oligos, or locked DNA. Hybridization of an oligo bound to an enzyme or polymerase may anneal at a higher temperature than a hybridization between a tunneling label and an oligo bound as a part of a SAM intended to increase a tunneling current of a tunneling label.

In some cases, a tunneling conductance label may comprise a quadruplex nucleic acid polymer. A quadruplex nucleic acid polymer may be formed from one, two, three, or four nucleic acid polymers. A quadruplex nucleic acid polymer may be formed with Hoogsteen binding of guanosine bases or naturally occurring epigenetically modified nucleotides, or non-naturally occurring nucleotides so as to form a high conductance label, with a conductance which may be higher than a duplex nucleic acid polymer. In some cases, multiple quadruplex labels may be utilized. Quadruplex labels may be used in combination with duplex labels and or other types of labels. Quadruplex labels may be configured to have sticky ends. Sticky ends may enable binding of labels to SAMs bound to electrodes of an electrode pair. Sticky ends may be further configured to have a linker bound to a nucleotide to be tested for binding and or kinetic behavior.

Figure 1J:
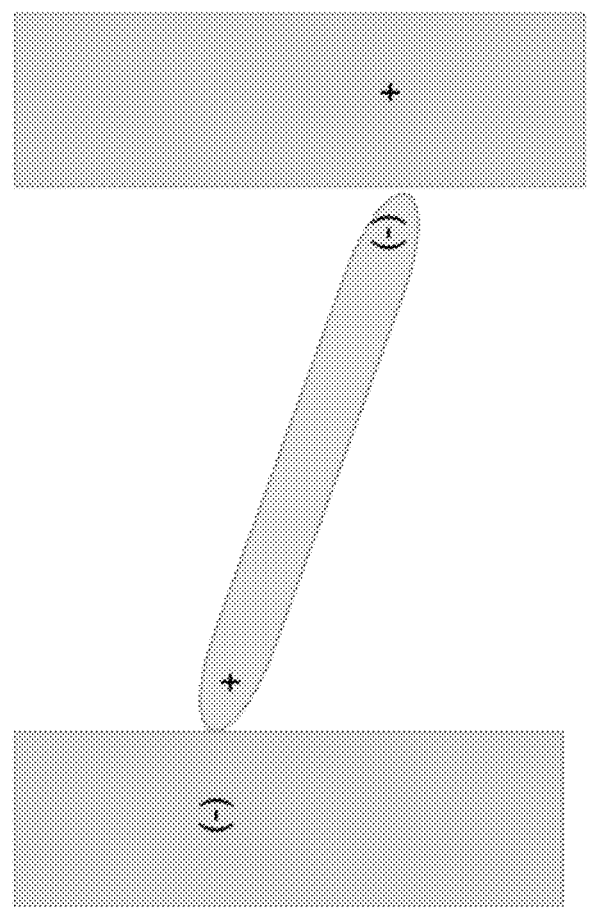
FIG. 1J depicts a zwitterionic molecule and its association with two electrodes.
Figure 1K:
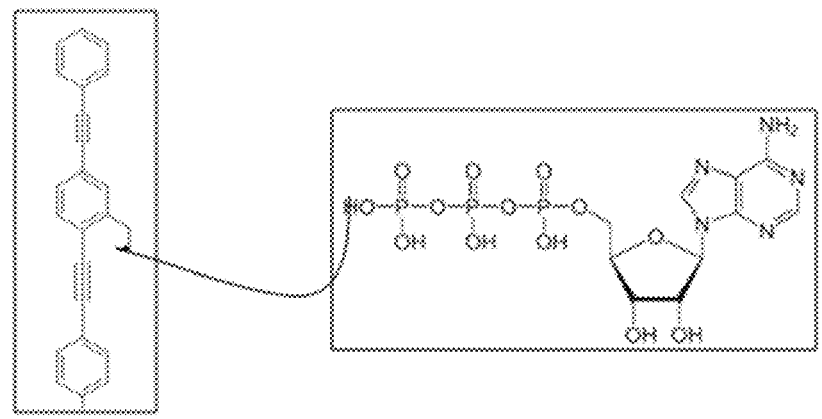
FIG. 1K shows a conductive label bound to a nucleotide.

In some cases, tunneling labels may be bound to a 5' phosphate chain of a nucleobase. Labels may be bound through a PEG or alkane linker or other suitable flexible chain, which may be a chimeric chain between a label and a nucleobase as shown in FIG. 1K, wherein a triphosphate is shown, although other lengths of phosphate chains may be utilized, or other chains may be utilized as described hereinafter. In some cases, a label may be bound to a nucleobase at the 3' position. A label may be bound through a cleavable linker, which may be a photocleavable or a chemically cleavable linker. A cleavable linker may leave a label bound to an enzyme complex until a label may be intentionally removed.

In some cases, a label may be bound to a nucleobase, which nucleobase may be bound by an enzyme. An enzyme may comprise a polymerase. Other labels and associated nucleobases which are not bound by an enzyme may be removed. A label may be bound to a SAM. A nucleobase may be incorporated and a linker may thus be cleaved between a nucleobase and its associated label. A label may then be measured, whilst still bound by the SAM, thus allowing measurement with localization of labels to target nucleic acid strands after cleavage.

In some cases, wherein synthesis of a desired label may be difficult, particularly when combined with binding, which may be covalent binding of a linker to a desired nucleotide, a label may be constructed of several parts and thence assembled rather than being synthesized as one piece. As shown in FIG. 1I, a main core oligo 120, which may have a linker 121, may be combined with unbound oligos 123A and 122B which may be complementary to portions of core oligo 120 and to stuck ends 124A and 124B. Previously free, but now ligated oligos 122A and 123B may now be bound using ligation to a core oligo 120 to form a or more complete label, wherein a desired nucleotide may have been bound to a terminal end of linker 121 either before ligation or after ligation.

In some cases, labels may be set at fixed conductance ratios, which may be in at set ratios in linear space, in log space, or in exponential space. In some cases, differences in label conductances may be set as a function of background noise levels. For example, a spacing of conductance levels may be set as a function of noise levels convolved with a defined conductance level, so that an overlap of conductance distribution may correspond to a desired overlap between different labels.

In some cases, a noise level may include kinetics of diffusing nucleotides which are not bound by a polymerase complex. In some cases, a noise level may comprise associated binding of sticky ends of nucleotides, which are not bound by a polymerase complex, to stuck ends of a SAM which may be bound to electrodes of an electrode pair. In some cases, a noise level may be dominated by a noise associated with diffusion and associated binding of sticky ends to stuck ends of a highly conductive label. This may require the least conductive label to be significantly farther separated in conductance from the next more conductive label. In some cases, both sticky ends of label may comprise the same sequence, while in other cases, two sticky ends of a label may comprise different sequences.

In some cases, a label portion of a molecule, which molecule may include a linker and a nucleobase, may be chosen as a zwitterionic compound with one side being positively charged and the other side being negatively charged. In some cases, a label portion of a molecule may have a net negative, a net positive, or a net neutral charge. In some cases, the label portion may have two ends each having a net negative charge and a net positive charge respectively. The net positively and net negatively charged ends may each be attracted to a different electrode, as shown in FIG. 1J wherein a zwitterionic label is shown between two electrodes, wherein the differently charged ends of the zwitterionic label may be attracted to two different electrodes with differing potentials. In some cases, a label may have a net neutral charge. For example, when a label may be formed using PNA bases or by modifications to linking phosphate groups such that the phosphate groups are uncharged.

In some cases, a label portion may have a slightly longer size than an electrode gap or binding location. For example, a zwitterion or similar molecule with different net charges at opposing ends of the label portion of the molecule may be stretched across a tunneling gap and may make a tunneling connection to the two electrodes when an electric field is applied.

Use of Other Types of Labels

In some cases, fluorescent labels may be utilized, for example to detect kinetics of binding. Fluorescent labels may be detected using a system which may comprise a zero mode waveguide nanopore, a TIRF detector, or detection of fluorophores localized by a nanopore. A fluorophore may be detected prior to entry in a nanopore in the cis side of a nanopore structure. In some cases, a fluorophore is detected just after exit in the trans side of a nanopore structure. In such cases, a polymerase may be fixedly bound to a zero mode waveguide or nanopore, such that transient binding of nucleotides may be observed as a result of binding. Different colors or wavelengths of fluorescent labels may be associated with different nucleotides in a set of nucleotides, thus allowing differentiation therebetween as described hereinabove with respect to tunneling and or hopping labels.

In some cases, charge blocking labels may be utilized. Charge blocking labels may be utilized such that a difference in current through a nanopore may be reduced as a result of the presence of a charge blocking label, during a period while being bound by an enzyme. An enzyme may be a polymerase. A polymerase may be fixedly or transiently bound to a nanopore. Different sizes of charge labels may be associated with different nucleotides in a set of nucleotides, thus allowing differentiation between nucleotide types, as described hereinabove with respect to tunneling and or hopping labels.

In some cases, electrochemical labels may be utilized. Electrochemical labels may be utilized such that a bound nucleotide may produce a current as a result of oxidation and reduction at two different electrodes of an electrode pair, which may be maintained at a voltage appropriate for the oxidation and reduction. In some cases, a same electrochemical label may be utilized for more than one type of nucleotide. A difference in diffusion may result in a different average current being generated for the different nucleotide types, as a result, for example, of different diffusion rates for the different nucleotides. Different diffusion rates may result from associating a same electrochemical label with different additional moieties. Different additional moieties may be electrochemically inactive. Different additional moieties may slow diffusion of an electrochemical label which may be linked to a nucleotide.

In some cases, different electrochemical labels may be utilized, and a current associated with an electrode pair may be measured at different times. A different potential may be utilized for one or both electrodes with respect to a bulk solution potential, such that currents associated with different electrode pairs may be used to differentiate different electrochemical labels.

In some cases, more than one electrode pair may be utilized. More than one electrode pairs may be associated with an enzyme binding site, such that more than one set electrode pair may be accessible by labeled nucleotides. Labeled nucleotides (e.g., labels associated with nucleotides) may be bound by an enzyme. Different electrode pairs may have one or both electrodes at different potentials with respect to a bulk solution, such that currents associated with different electrode pairs may be used to differentiate different electrochemical labels.

In some cases, a combination of multiple sets of different electrodes may be used, such that such that currents associated with different electrode pairs may be used to differentiate different electrochemical labels. Different nucleotides which may have a same electrochemical label may further comprise one or more additional moieties, such as proteins. The one or more additional moieties may or may not be the same. In some cases, one or more additional moieties may be different such that a same electrochemical label may have different diffusion rates and thus different currents.

In some cases, a single label molecule may comprise one nucleobase bound through a linker. In some cases, a single label molecule may comprise multiple nucleobases bound through one or more linkers to a single label. In some cases, all of the multiple nucleobases may be of a same type of nucleobases. In some cases, some of the multiple bases may comprise different types of bases. Different types of bases may comprise different types of nucleobases, such as adenosine or guanosine, or may be modified nucleobases, for example epigenetic modifications or any other type of modification, including backbone modifications. In some cases, a single label molecule may comprise one or more nucleobases, and one or more labels, wherein labels may be the same or may be different, possibly having different binding mechanisms, potentially with different binding kinetics, or different conductances.

In cases where multiple labels may be bound together and associated with one or more nucleobases, a system may be configured such that a kinetics of binding may be slow relative to current measurement capabilities of a system, and at least a portion (e.g., at least about 5%, 10%, 15%, 20%, 25%, 30%, 35%, 400,%, 45%, 50%, 55%, 60%, 70%, 80%, 90%, 95%, or 99% or more) of the labels may be identified as a result of the kinetics and or conductance. Labels may have different conductance and or different binding kinetics. In some cases, for each label, some or all fractions of labels may be identified. In some cases, a moiety bound to the labels may be identified as a result of identification of labels, thus allowing a larger number of different types of labeled moieties to be identified while using a smaller number of individual identifiable labels.

In some cases, a same or different binding moieties, which may be a sticky end, may be utilized. Binding moieties may be utilized for different base types. Different base types may comprise epigenetic modifications. Different binding moieties may comprise different sequences. Different sequences may have different kinetics, such that average conductance may be influenced by kinetics. In some cases, small changes in a sequence associated with binding to a SAM comprising a polynucleotide may make only small changes in the conductance, but may make substantial differences in the average binding time, thus making an average current significantly different.

In some cases, fluorescent labels, charge blocking labels, or electrochemical labels may be bound, linked or associated with different nucleotide types. In some cases, fluorescent labels, charge blocking labels, or electrochemical labels may be bound, linked or associated with other different moieties. Non-limiting examples of moieties include amino acids, oligonucleotide probes, aptamers, antibodies, or any other types of binding moieties, or combinations thereof. In some cases, differentiation between different target moieties may be effectuated by binding or localization of one moiety in an area of a detection region, such that interaction between one moiety and another moiety to which a label may be bound may be detected, and different target moieties may be detected by detecting different labels.

In some cases, different moieties may be detected by using assays similar to a proximity ligation assay. In an assay, two different binding moieties may both bind to a target moiety. An increase in local concentration may allow additional interaction between different binding moieties, which may then interact as a result of ligation, hybridization or other binding interaction. Ligation, hybridization or other binding interaction may then allow detection as a result of local proximity of two binding moieties labels, as by for example, FRET between two different fluorophores; electrochemical pairing of two electrochemical moieties in association with electrode pairs wherein a potential between two electrodes may be inappropriate for either of the single electrochemical moieties, but may be appropriate for the electrochemical pair; combining two tunneling and or hopping oligo labels, wherein either label may be too short to span a gap between two electrodes of an electrode pair, or may only be complementary to a SAM on one side, but a hybridized or ligated combination of two labels may allow detection as a result of extending the length of combined labels, which may further serve to allow simultaneous hybridization to SAMs on both electrodes of an electrode pair.

In some cases, a physical blocker may have a net charge, such as a negative charge or a positive charge, or may have a net neutral charge, or minimal positive or negative charge, or may have a magnetic or para-magnetic core or associated moiety, such that a physical blocker may be moved in response to an external force, such as an electric field, an electroendosmotic flow, a magnetic force, or any combination thereof.

In some cases, a physical blocker may be bound to an enzyme, such as a reverse transcriptase or any other desired type of enzyme, and may be bound through an appropriate linker, such as an alkane linker, a PEG linker, or any type of linker, which may be a polymer, a chimeric polymer, or a polymer combined with other moieties. In some cases, a physical blocker may be bound or attached to a complexed oligo after complexation, for example by ligation; a non-complexed portion of a physical blocker may be provided at a higher, potentially much higher concentration than a concentration of complexed portions prior to attachment or binding. In other cases, a physical blocker may be elongated before or after complexation.

In some cases, a physical blocker may comprise a circular nucleic acid, which may be a circularized sample nucleic acid, or may be a synthetic or copied natural nucleic acid; a circularized nucleic acid may complexed and may be extended, thus creating a nucleic acid ball which may act as a physical blocker, and may be extended either prior to or after binding of a polymerase or other enzyme to a sensor. If a physical blocker forming circular nucleic acid is extended after binding or attachment of a polymerase or other enzyme to a sensor, a polymerase or other enzyme may be provided with a sufficiently low concentration relative to a binding rate that an extension may occur such that an extended circular nucleic acid may be sufficiently enlarged so as to prevent binding by another polymerase or other enzyme at a same sensor wherein an existing polymerase or other enzyme may be bound.

In some cases, extension of circular nucleic acids may be largely prevented prior to attachment or binding to a sensor by providing a continuous flow of additional polymerases or other enzymes, circularized nucleic acids, incorporable nucleotides, and catalytic divalent cations, wherein not all of polymerases or other enzymes, circularized nucleic acids, incorporable nucleotides, and catalytic divalent cations may be available for complexation and extension prior to introduction to a sensor.

In some cases, a physical blocker may be larger than a width or spacing of a gap between electrodes of an electrode pair. A physical blocker may be longer than a length of electrodes of an electrode pair. In some cases, a physical blocker may be at least about 110%, 125%, 150%, 160%, 170%, 180%, 190%, 200% (or more) larger in width or length than the electrodes of an electrode pair, such that even when considering factors including e.g., a length of linkers between an enzyme and a binding surface, dimensions of an enzyme, and a length of any linker from an enzyme to a binding surface in association with an electrode structure comprising an electrode pair, more than one enzyme and physical blocker pair may not be bound to a same electrode pair as a result of a physical blocker sterically interfering with a binding of another enzyme and physical blocker pair.

Cleaning of Electrodes

In some cases, removal of a SAM may be effectuated by use of an electric field, as has been described for the removal of amine or thiol SAMs. In some cases, a SAM may be removed and reapplied to the electrodes. In some cases, a SAM may be removed and a same type of SAM may be applied to a same electrode(s) so as to renew a SAM. In some cases, a SAM may be removed, and a different type of SAM may be applied to electrodes.

In some cases, a surface of an electrode pair may be cleaned. A surface may be cleaned using an electrochemical cleaning process. An electrochemical cleaning process may be combined with a wash step to remove any contaminants which may be bound to a surface of an electrode prior to introduction of reagents associated with a formation of a SAM.

In some cases, an electrochemical cleaning process may be used to remove contaminants from an electrode surface after applying a SAM. A process may utilize a voltage. A voltage may be sufficient to remove contaminants, but insufficient to remove a SAM.

In some cases, plasma cleaning may be utilized, at least in part to clean a sensor or set of sensors. In some cases, a high temperature oxidative cleaning may be used to clean a sensor or set of sensors. A temperature may be greater than or equal to about 500° C., 600° C., 700° C., 800° C., 900° C., 1,000° C., 1,100° C., 1,200° C., 1,300° C., 1,400° C., 1,500° C., 1,600° C., 1,700° C., 1,800° C., 1,900° C., 2,000° C. or higher. In some cases, a piranha, sulfuric acid, KOH, NaOH or other oxidative or reductive cleaning method may be utilized to clean a sensor or set of sensors.

In some cases, in order to allow wetting of a sensor structure by an aqueous or primarily aqueous solvent, which may be utilized in a method with the sensors, cleaning, which may be effectuated prior to bringing a primarily aqueous solvent into proximity with sensors, or may be effectuated by use of miscible solvents, which are not primarily aqueous, and which may subsequently be replaced with a primarily aqueous solvent, mixtures which lower a contact angle, electrowetting or a combination of any of the above may be utilized. For example, alcohols may be utilized to allow wetting when a primarily aqueous solvent may be incapable of fully wetting a sensor structure, which may comprise a nanogap. In some cases, an electrowetting potential may be used which may be −0.5V to −0.7V, −0.7V to −1.0V or less than −1.0V relative to Ag/AgCl in order for proper electrowetting of a nanogap structure to occur wherein gold or other noble metal sense and bias electrodes may be utilized. An equivalent potential associated with other metals may be used.

In some cases, wetting and or cleaning of a sensor structure may be effectuated using an addition of a surfactant to an aqueous solvent which might otherwise be incapable of wetting a sensor structure. In some cases, a surfactant may be a nonionic surfactant such as glycerol esters or terdodecyl mercaptan. In other cases, a surfactant may be an anionic surfactant such as alkyl ester sulfate or dodecyl benzene sufonate. In further cases, a surfactant may be a cationic surfactant such as dodecyl amine or imidazole. In yet further cases, a surfactant may be an amphoteric surfactant, a silicon surfactant, a fluorinated surfactant, or a polymeric surfactant.

In some cases, wetting and or cleaning may be effectuated with an alcohol, or a mixture of alcohol and aqueous reagents, which may include an ethanolic KOH mixture. An alcohol, or a mixture of alcohol and aqueous reagents, may be utilized to clean sensor surfaces such that wetting with a primarily aqueous solvent may occur, or wetting with a primarily aqueous reagent may occur due to e.g., pinning or hysteresis after replacement or dilution of a reagent with a higher organic content. In some cases, a primarily aqueous solvent may contain no organic solvents. In some cases, a primarily aqueous solvent may contain a sufficiently low percentage of organic solvent (e.g., less than or equal to about 20%, 15%, 10%, 9%, 8%, 7%, 6%, 5%, 4%, 3%, 2%, 1%, 0.5%, 0.1%, 0.05%, 0.01% (wt %, vol %, or mol %) or less) such that the activity of an enzyme utilized as a part of a detection method may be inhibited by less than or equal to about 90%, 80%, 70%, 60%, 500%, 40%, 30%, 20%, 10%, or less.

In some cases, wetting of a sensor structure may be effectuated with a solvent which may not otherwise be able to wet all or part of a sensor structure by application of a wetting potential to one or more electrodes of a sensor or set of sensors, which may include all of the sensors on a chip. In some cases, a bulk fluid potential may be effectuated using a quasi-reference electrodes, such as, for example, an Ag/AgCl reference electrode which may also be used as a counter electrode. In some cases, a counter electrode, which may be a platinum electrode, may be used in addition to a reference electrode, which may be an Ag/AgCl electrode.

In some cases, a counter electrode and or reference electrode or quasi-reference electrode may be incorporated into a chip. A chip structure may include a micro, nano or macro fluidics system. A fluidics system may be integrated as a part of a chip assembly. A fluidics system may be a part of an external fluidics system. A fluidics system may be upstream or downstream of one or more fluidic interfaces to a chip assembly. In some cases, one or more reference electrodes may be utilized. Reference electrodes may be utilized, which may include aqueous or nonaqueous electrodes. Reference electrodes may include a saturated calomel reference electrode, a copper/copperII sulfate electrode, or any other appropriate reference electrode. In some cases, different types of counter electrodes may be utilized, including stainless steel, nickel, gold, or carbon.

In some cases, a salt bridge may be utilized to separate reference and or counter electrodes from sensor electrodes, such that salts appropriate for, for example, a reference electrode, do not interfere with proper functioning of sensor electrodes. For example chloride ions needed for proper functionality of an Ag/AgCl reference electrode may result in removal of gold, which may be a part of a sensor electrode. Such a salt bridge may include a polymer to prevent fluidic movement which might result from static pressures or other sources of bulk fluid movement, or may not include such a polymer and may thus permit fluidic exchange through a pathway between a reference and or counter electrode, and a sensor electrode pair or set of sensor electrodes.

In some cases, a method may be utilized to insure that wetting has occurred. Such a method may utilize redox cycling moieties such as ferrocenium/ferrocene, or ferrocene derivatives, or hexamineruthenium, wherein changes in electrochemical currents may be measured, and differences observed may indicate wetting of electrodes and or nanogaps associated with sensor electrodes, particularly as a function of potentials and hysteresis and pinning. In some cases, capacitive measurements of double layers associated with electrodes of sensors may be measured, and changes in capacitance may be measured as an AC waveform, which may be utilized to determine a capacitance associated with electrodes of a sensor, and a DC potential, which may be changed so as to determine a wetting potential or potentials associated with sensor electrodes.

In some cases, wetting potential may be effectuated by a negative potential, which may be applied to the electrodes of a sensor relative to a reference electrode. A negative potential may be effectuated by changing a potential of one or more electrodes of a set of sensor electrodes, or may be effectuated by changing a potential of a reference and or counter electrode relative to one or more electrodes of a set of sensor electrodes, or both potentials of a set of sensor electrodes and a potential of reference and or counter electrodes may be changed relative to each other. In some cases, a wetting potential may vary for different portions of a sensor, for example, when one electrode is formed with predominantly one crystal plane, for example a 111 crystal plane, while another electrode may have a different crystal plane or a mixture of crystal planes. In such cases, a different voltage may be applied for different electrodes relative to a reference electrode, such that different electrowetting potentials present for different crystal planes, and may thereby offset different wetting angles associated with different crystal planes.

In some cases, a dewetting potential or potentials, which may be aligned with expected crystal planes as described hereinabove, may be applied in a manner similar to a wetting potential, which may allow for quicker removal of fluids which may be effectively in contact with an electrode or set of electrodes. A fluid may, for example, be at least partly blocked from contacting one or more electrodes as a result of a SAM which may bind to one or more electrodes. A fluid in contact with such a SAM may be considered to be in effective contact with an electrode or set of electrodes. A dewetting potential may also permit an exchange of fluids to occur without exposing a sensor or set of sensors to a mixture of fluids as typically occurs when one fluid is replaced with another, as a sensor or set of sensors may not be in effective contact with fluids at a time of exchange. For example, one set of labels may be exchanged with another set of labels, or one set of ions such as Calcium may be exchanged with another set of ions, such as magnesium, and may leave an extended DNA strand bound to an enzyme, such as a polymerase with only hydration that would be expected from a 100 percent humidity environment. In some cases, a pressure, which may be a positive or negative pressure, may be used to help wet surfaces, which may include nanogaps or other electrode structures. In some cases, a pressure, which may be a positive or negative pressure, may be used with other wetting aids such as surfactants, low surface energy solvents, or electro-potentials.

Electrode Cleaning and Electrode Bound Self Assembled Monolayers

In some cases, a self-assembled monolayer (SAM) may comprise thiolated DNA, wherein monolayers on different electrodes may be a same monolayer sequence and or orientation of DNA, wherein the 3' end or the 5' end may be bound to a thiol or other binding group, and may thence be bound to an electrode. In some cases, a different sequence and or orientation may be utilized for monolayers on different electrodes, wherein different electrodes may be functionalized in separate groups as a result of changing a bulk fluid potential and or a bias potential between electrodes, such that thiolation occurs on some electrodes, and not on other electrodes whilst one type of monolayer compound is made available for binding to one set of electrodes. Potentials of a bulk solution and or bias electrodes may be modified such that thiolation of a different set of electrodes may occur. Such modification may be effectuated in a manner that prevents new thiol groups from binding to an electrode set with a previously bound monolayer, or additional thiolated molecules may be substantially prevented from binding as a result of full occupancy of binding sites by the existing monolayer.

In some cases, other binding mechanisms may be utilized so as to provide improved tunneling paths. Non-limiting examples of binding mechanisms may include proteins, antibodies, aptamers, other organic polymers, or combinations thereof. Binding between a binding portion of a label and SAM associated with an electrodes may desirously increase tunneling or tunneling and hopping current between electrodes.

In some cases, SAMs may utilize a single thiol to bind to an electrode surface. In some cases, a dithiol such as a carbodithiolate linker may be utilized to form at least a part of a SAM compound. In other cases, amines, diamines, carboxylates, phosphines, alkylsiloxanes, trichlorosilanes, perfluoroalkyls, or any other appropriate binding groups may be utilized to bind to an electrode or a dielectric between electrodes or other regions associated with a set of sensors.

In some cases, a method for attaching a SAM may comprise a number of steps, which may include: providing a salt solution. The salt solution may comprise: Saline Sodium Citrate (SSC, 1 M NaCl+100 mM Sodium Citrate); hybridizing nucleic acids in the salt solution, which may comprise a sequence of GGG CCC GGG and a thiol group, which may be a base bound thiol or dithiol group, and other nucleic acids, which may be complementary or sufficiently complementary as to remain bound. The method may further comprise preparing electrode pair sets, which may comprise gold or other noble metals, by boiling in piranha solution for 15 to 20 minutes, and thence removing the piranha solution with clean 18 Gohm water.

A solution of hybridized nucleic acids may thence be brought into contact with the electrode pair sets for a period of time to allow binding of hybridized nucleic acids to electrodes utilizing thiol or dithiol groups. A contacting time may be greater than or equal to about 1 minute (min), 10 min, 20 min, 30 min, 40 min, 50 min, 60 min, 1.5 hours (hrs), 2 hrs, 3 hrs, 4 hrs, 5 hrs, 6 hrs, 7 hrs, 8 hrs, 9 hrs, 10 hrs, 12 hrs, 14 hrs, 16 hrs, 18 hrs, 20 hrs, 22 hrs, 24 hrs, 26 hrs, 28 hrs, 28 hrs, 30 hrs, 35 hrs, 40 hrs, 45 hrs, 50 hrs, or more. In some cases, a contacting time may be less than or equal to about 5 days, 4 days, 3 days, 2 days, 1 day, 20 hrs, 15 hrs, 10 hrs, 8 hrs, 6 hrs, 4 hrs, 2 hrs, 1 hr, 40 min, 20 min, 10 min, 5 min, 1 min, 30 seconds (sec), 20 sec, 10 sec, or less. In some cases, a contacting time may be between any of two values described herein, for example, from about 1 min to about 10 min, from about 1 hr to 3 hrs, from about 3 hrs to about 10 hrs, or from about 10 hrs to overnight. A solution of hybridized nucleic acids may be removed, and a wash, which may comprise a salt solution, or may comprise clean 18 Gohm water may then be used to further remove any remaining unbound hybridized nucleic acids.

In some cases, an oxidative or reductive cleaning of bias and sense electrodes may be utilized, which may make use of a sulfuric acid potential sweep from 0 to +1.2V re Ag/AgCl, or may use a method for cleaning a set of electrodes which may comprise: applying a 10 mM solution of KOH; sweeping a potential of the set of electrodes from 0.0 volts to −1.3V relative to Ag/AgCl; removing the potential and thence the KOH solution, followed by a wash with deionized water.

As nucleic acids may form unwanted amine bonds between bases of nucleic acids and a surface, a solution of mercaptopropanol, mercaptoethanol, mercaptohexanol, methyl mercaptan, 1-mercapto-11-undecanol, 1-Propanethiol, 2-Propanethiol, Butanethiol, tert-Butyl mercaptan, Pentanethiols, Thiophenol, Dimercaptosuccinic acid, Thioacetic acid, dithiols, or other sulphurous groups which may bind to noble metals may be used as a backfill Sulphurous groups may displace amine binding between bases and electrode surfaces, and may further displace some larger nucleic acids which may be bound to electrode surfaces.

Sulphurous groups, which may comprise mercaptopropanol, may be mixed with a salt solution as previously described, and the reagent mixture may brought into contact with electrodes, so that the sulphurous groups may bind thereto. A binding may be for less than or equal to about 5 hrs, 4 hrs, 3 hrs, 2 hrs, 1 hr, 50 min, 40 min, 30 min, 20 min, 10 min, 9 min, 8 min, 7 min, 6 min, 5 min, 4 min, 3 min, 2 min, 1 min, or less. In some cases, the binding may last for at least about 1 min, 5 min, 10 min, 30 min, 50 min, 1 hr, 2 hr, or more. In some cases, the binding may last for about 1 min to 10 min, for about 10 min to 30 min, for about 30 min to 2 hrs, or for more than 2 hrs. In some cases, a potential may be utilized to speed a binding of a SAM to an electrode, which may be a sense or bias electrode. Such a potential may be from −0.5V to −0.2V, from −0.2V to 0.0V, from 0.0V to 0.2V, or from 0.2V to 0.5V, all relative to Ag/AgCl when using gold electrodes. In some cases, potentials may be modified as appropriate for other metals or references both for formation of SAMs and as appropriate for other processes wherein potentials may be described. In further cases, a potential sweep may be utilized when an optimal potential for binding of a SAM binding moiety may not be fully conducive to formation of a SAM due to electrostatic attraction of other portions of a SAM; thus in some cases, a potential may be swept between surface potentials which may be more optimal for binding, and potentials which may be more optimal for preventing steric hindrance due to surface attraction of other parts of a SAM moiety.

A sulfurous group containing reagent mixture may thence be removed, and electrodes may be washed, which may be with a salt solution, and or clean 18 Gohm water.

In some cases, different dendrimers may be utilized in binding regions, which may be a SAM binding region. In some cases, a single dendrimer may comprise multiple binding moieties, such as, for example, different DNA sequences. In some cases, different binding regions may comprise different binding moieties. In some cases, multiple binding moieties may be utilized in a single binding region. As a result of these different localizations of different binding moieties, regions may effectively be encoded.

In some cases, a different linker, such as a PEG, alkane or any other appropriate polymer functionalized with, for example, a thiol at one end, and another functional group at another end may be used to bind one or more locations on an enzyme or polymerase. In some cases, more than one linker may be used to bind an enzyme or polymerase into position.

In some cases, labeled nucleotides may be utilized wherein a nucleotide may have net negative charge, net positive charge, or net neutral charge. In some cases, SAMs utilized to increase tunneling currents through tunneling labels, and or tunneling labels may utilize nucleobases with negative, positive, neutral, or any combination of charges on different nucleobases.

In some embodiments structures associated with electrodes may have a SAM applied in a specific manner. First a device may be treated by adding a SAM with a functional group that may bind to a metal of both electrodes as well as associated dielectric surfaces such as a dielectric which may form a spacer between a bias electrode and a sense electrode, and thereby form a bottom to a nanogap. Then a voltage may be applied to a set of electrodes with respect to a bulk solution, so as to remove functional groups from electrodes, and thereby functional groups may remain on associated dielectric surfaces.

In some cases, SAMs may be formed using aptamers, allowing binding and detection of various types of molecules, such as proteins. Different oligos may be utilized for SAMs, and may bind to different parts of a protein, and may also be designed to bind in close proximity, to each other on the surface of a protein, so that larger amounts of current may be generated. In some cases, SAMs may be formed using multiple different types of aptamers, allowing binding of multiple types of proteins, and or tighter binding of a single protein.

In some cases, SAMs may comprise antibodies, allowing detection of various antigens, including various proteins, but also a variety of other types of antigens. Different antibodies may be utilized on different electrodes of an electrode pair, so that a sandwich assay may be created. Antibodies may be utilized as a part of a conductive path, which may include a target antigen. In some cases, antibodies may be combined with aptamers, either to optimize binding and or to optimize conductance. SAMs may be formed using antibodies, allowing detection of various antigens, and may be formed with multiple antibodies, allowing detection of multiple antigens, or more specific binding of a single antigen.

SAMs may comprise a mixture of different types of binding moieties, which may include one or more types of hybridizing nucleic acids, one or more types of aptamers, one or more types of antibodies, and one or more types of any other appropriate binding moiety, and may be formed in any proportion between different types of different binding moieties.

An electrode pair may be configured with a SAM on one electrode and no SAM on an adjoining or opposing electrode. SAMs may utilize different types of binding mechanisms to bind to a electrode, such as thiols, amines and other binding mechanisms. Different target binding mechanisms may be utilized, for example, a SAM may comprise an aptamer, while a SAM on an opposing/adjoining electrode may comprise an antibody.

In some cases, mixtures of different types of binding mechanisms may be utilized with a same target binding molecules. For example, a same aptamer type may be bound with amines and thiols.

In some cases, multiple different targeting molecules may be utilized within a SAM on a single electrode, or on adjoining/opposing electrodes, so that multiple targets may be targeted using a same electrode pair. For example different proteins with different conductances when captured may be targeted using different binding molecules or may be captured using a universal binding capture molecule, wherein different conductances may allow determination of which target has been captured.

In some cases, binding and or release of a target by SAM may be assisted by the use of an electric field, as has been described for improving the binding speed in forming amine or thiol SAMs, for example, by increasing a hybridization binding and or increasing a rate of denaturation by changing a potential on electrodes, which may be different potentials which may in part correspond to differences in crystal plane, and may further allow matching of crystal plane point of zero charge and associated potential to a desired tunneling potential between electrodes.

In some cases, SAMs may be formed with differing ratios between different moieties comprising a SAM. In some cases, a SAM binding ratio may not match a molarity ratio, but may also result from different sizes and binding efficiencies of different moieties. In some cases, a SAM may be formed with a mixture of binding and non-binding moieties so that a number of binding moieties on a surface may not be driven by kinetics and time, but may be primarily be a competitive reaction. In some cases, a number of different types of moieties may form a SAM, and may be formed with ratios between different binding members formed primarily by competition. Such moieties may comprise spacers, label binding, target binding, enzyme binding moieties, and may be different and placed at different concentrations on one or more surfaces, or at a same concentration on one or more surfaces.

In some cases, rather than attaching a strand of a nucleic acid or other polymer, a nucleic acid or other polymer may be synthesized locally. A synthesis may use fields associated with electrodes of an electrode pair to control attachment of individual bases as desired such that different sequences may be generated at different sensors, thus allowing, for example, different sensors to detect different amplification products from a multiplex real time PCR reaction, hybridization assay, or another type of assay which may wish to detect a number of different types of moieties, for example, different sequences of nucleic acid polymers.

In some cases, electric fields associated with electrodes of an electrode pair may have voltages applied at different times so as to allow binding of different pre-synthesized oligos and to enable different sensors to detect different amplification products from a multiplex real time PCR reaction, hybridization assay, or another type of assay which may wish to detect a number of different types of moieties, for example, different sequences of nucleic acid polymers.

In some cases, a SAM may be formed using a mixture of binding and non-binding moieties. A binding moiety may comprise a nucleic acid polymer with a specific sequence. A non-binding moiety may comprise a nucleic acid polymer with a different sequence, a different polymer such as a PEG polymer, alkane polymer, or other appropriate polymer which may not bind specifically or nonspecifically to a moiety which binds specifically to a binding moiety, or may comprise a chimeric polymer which may not bind specifically or nonspecifically to a moiety which binds specifically to a binding moiety, or may comprise a non-polymeric moiety, which may not bind specifically or nonspecifically to a moiety which binds specifically to a binding moiety, so that a number of binding moieties on an electrode surface may not be driven by kinetics and time, but may instead be driven by competition between different moieties competitively.

In some cases, a non-binding moiety, which may be utilized with an electrode which may comprise a noble metal, such as ruthenium, rhodium, palladium, silver, osmium, iridium, platinum, and gold, and may comprise other metals, may utilize a thiol attachment to a noble metal, and may comprise a moiety such as a solution of mercaptopropanol, mercaptoethanol, mercaptohexanol, methyl mercaptan, 1-mercapto-11-undecanol, 1-propanethiol, 2-propanethiol, butanethiol, tert-butyl mercaptan, pentanethiols, thiophenol, dimercaptosuccinic acid, thioacetic acid, dithiols, or other sulphurous groups which may bind to noble metals. Such a non-binding moiety may further comprise an alkane, PEG (polyethylene glycol), or other polymer, which may be of any desired length, and may be of 1, 2, 3, 4, 5, 6, 7, 8, 9, 10, or more than 10 units in length.

In some cases, a backfill may be used. A backfill may comprise a non-binding moiety as described hereinabove. Steps in such a process may comprise binding a stuck end as shown in FIG. 1L, subsequently binding a backfill after a stuck end SAM may be formed as shown in FIG. 1M; in further cases a surface concentration of stuck ends may be quantified by hybridizing a moiety which may be useful in an RTPCR amplification process and then washing away unhybridized RTPCR amplifiable moieties as shown in FIG. 1N, followed by denaturation and capture of amplifiable RTPCR moieties as shown in FIG. 1O, and subsequently quantifying and normalizing with reference to surface area and hybridization efficiency. In other cases, a backfill may be formed at a same time as a SAM which may comprise binding moieties. In some cases, a SAM or at least a portion of the moieties comprising a SAM may be hydrophilic, such that a surface which may have a SAM bound thereto, may effectively have a higher energy surface, and may thereby wet more easily.

In some cases, ratios between different binding members may be set by competition, which may include binding preferences as a result of the use of different spacers, label binding, target binding, enzyme binding moieties, which may be different and may be associated with a surface so as to create different surface concentrations, or at a same surface concentration. A concentration in solution may be the same or different. In some cases, an effective surface concentration may be the same or different as a result of different size or binding efficiencies of different binding moieties.

In some cases, mixtures of different types of binding mechanisms may be utilized with a same target binding molecules. For example a same type of aptamer may be bound with amines and thiols, or two different aptamers may be bound using different binding methods.

In some cases, multiple different targeting molecules may be utilized within a SAM on a single electrode, or on adjoining/opposing electrodes, so that multiple targets may be targeted using the same electrode pair. For example, different proteins with different conductances when captured may be targeted using different binding molecules or may be captured using a universal binding capture molecule, wherein different conductances may allow determination of which target has been captured.

In some cases, electrodes may be configured to capture a single molecule or complex, or may be configured to capture multiple targets of the same type, wherein a current level measured may be utilized to determine a number of molecules captured.

In some cases, a set of electrodes may be cleaned, and a SAM layer may be created on a set of electrodes. Various measurements may be made utilizing at least a portion of a set of electrodes, and thence a SAM may be removed utilizing a cleaning process. Another SAM, which may be of the same configuration type, or of a different configuration type, may be applied and additional measurements may be made. Such a cycle may be repeated as many times as is desirable. A cycle may be limited, for example, by fouling or erosion of the chip sensors. A cleaning process may be utilized between different samples, which may allow an appropriate certainty that a previous sample may have been removed, degraded, or otherwise rendered such that a subsequent measurement may be unaffected with a certain tolerance.

In some cases, a SAM may be formed utilizing hybridization oligos. Hybridization oligos may be configured with an alkane or PEG linker polymer bound to one end of a hybridization oligo, which may be a 3' or a 5' end of an oligo. A thiol or dithiol group may then be bound to a terminal end of a linker alkane, PEG, or other more conductive chain such as some of other conductive polymers described hereinabove, which may thence be utilized to bind to an electrode surface. A length of an alkane or PEG or other conductive linker polymer is not limited, and may be at least about 1, 2, 3, 4, 5, 6, 7, 8, 9, 10 units, or more than 10 units in length. In some cases, a length of a linker polymer may be uniform. In some cases, different lengths may be used for different binding moieties, or for a single type of binding moiety. In further embodiments a backfill, which may comprise a single type or different types and may comprise, a single length of a linker or different lengths. In some cases, a length utilized for a binding moiety may be the same, or predominantly the same as a length utilized for a non-binding moiety. A length utilized for a binding moiety may be longer or predominantly longer than a length utilized for a non-binding moiety. A length utilized for a binding moiety may be shorter or predominantly shorter than a length utilized for a non-binding moiety.

In some cases, a SAM, which may utilize a linker bound to a 3' end of a hybridization oligo, may be bound to one electrode of an electrode pair, while a linker which may be bound to a 5' end of a hybridization oligo may be bound to another electrode of an electrode pair. In some cases, differential binding of one SAM type to one electrode of an electrode pair, and second SAM type to a second electrode of an electrode pair, may be effectuated by utilizing different potentials at different times for different electrodes.

For example, using 111 crystal plane gold electrodes and an Ag/AgCl reference electrode, with a first SAM type in proximity to both electrodes of an electrode pair, a potential of −0.4 may be applied to a first electrode of an electrode pair, thus causing a SAM to bind to a first electrode, while 0.5V may be applied to a second electrode of an electrode pair thus causing a SAM to not bind to a second electrode. A potential of a first electrode of an electrode pair may then be brought to 0.5V, thus preventing further binding, and a second type of SAM may be brought into proximity to both electrodes of an electrode pair, and thence a potential of −0.4 may be applied to a second electrode of an electrode pair thus causing a second SAM to bind to a second electrode, while 0.5V may be applied to a first electrode of the electrode pair thus causing a second SAM to not bind to a first electrode. Thus different SAMs may be applied to different electrodes of an electrode pair, permitting hybridization of both ends of a single ssDNA strand, which single ssDNA strand, which may be a label, and may be partly double stranded.

In some cases, SAMs may be formed using oligos which may be completely synthesized externally. Alternatively or additionally, when highly customizable targeted may be desirable, SAMs may be at least partly synthesized locally using electric field(s), wherein different nucleobases may be introduced and bound at different times on different electrodes, for example, as described by Heller et. al. in U.S. Pat. No. 5,929,208, which is incorporated by reference in its entirety. Customization may be utilized so as to perform different types of tests utilizing different sets of sensors, or may be utilized so as to localize and bind different portions of a sequence using targeting, wherein oligos, which may be utilized for targeting may be bound to measurement sensors, or may be bound to additional electrodes which are separate from those electrodes utilized for measurement sensors, wherein additional electrodes may be utilized only for targeting, or may also be used for another purpose. Customization may result from local synthesis, or partial local synthesis, or from binding of externally synthesized oligos to specific or random electrodes.

Enzymatic Binding to Surfaces

In some cases, center dielectric regions may comprise titanium $TiO_2$, $SiO_2$, $GeO_2$, $Si_3N_4$ or other oxides, carbides, or nitrides. In some cases, an amidogen group may be utilized to bind a linker or functional group to a center dielectric region, such as for example, a $Si_3N_4$ center dielectric region. An amidogen group may comprise one or more of aldehyde, ester, halogenide, epoxide, imine, isocyanate, and combinations thereof. Alkane phosphonic acid and $NaN_3$ may be used to create azide functional groups on center dielectric regions, particularly on $TiO_2$ dielectric structures.

In some cases, azide functional groups may be created prior to binding of a polymerase to the device utilizing amine groups which may be an intrinsic part of a polymerase, or may be a part of a moiety which is bound to a polymerase, and may be bound through a linker. In some cases, a part of a linker which may be used to bind a polymerase or other enzyme to a dielectric may be made to be cleavable. In other cases, chlorides may be replaced with azide groups to functionalize a linker, and the functionalization may be effectuated within an instrument as a part of run or method.

In some cases, binding or association with center dielectric regions may comprise silanization. Silanization may utilize aminopropyltriethoxysilane with activation using glutaraldehyde. In some cases, carboxylic acid terminal groups, such as carboxylic acid esters groups may be utilized to bind to oxides or nitrides. In some cases, alkyl or alkenyl functional groups may be utilized to bind to hydrogen terminated surfaces of dielectric materials. Attachment may optionally be effectuated by use of photoactivation.

In some cases, an enzyme may be modified. An enzyme may be modified such that a functioning part may be an original size of an enzyme or polymerase, while overall size may be expanded. Such modified enzyme or polymerase may be disposed in a sensor with a cross sectional shape of an inverted cone or pyramid between a top portion and a sensing portion. As nucleotide bases with labels interact with an enzyme or polymerase, an enzyme or polymerase may extend a double stranded part of a target DNA or polynucleotide by one base. Sensing electrodes may generate a signal caused by the placement or effective high local concentration of a label of a bound or incorporated nucleotide base in a gap between two electrodes.

In some cases, a polymerase may be associated with (e.g., bound to) sidewalls of a structure. A structure may comprise one or more electrodes of a sensor structure. A polymerase may be associated with a structure using hybridization and or ligation. A polymerase may be hybridized or ligated to an oligo which may be a part of a SAM. An oligo may be utilized to facilitate higher tunneling currents by, for example, hybridization to a tunneling label. In some cases, a polymerase may be hybridized or bound to an oligo which may not be used to facilitate higher tunneling currents, and may have a different sequence than a sequence which may be used by an oligo used to facilitate higher tunneling currents.

In some cases, two electrodes may be used as a pair for a single sensor associated with an enzyme or other moiety for which label binding monitoring may be desired. In some cases, more than one electrode pair (e.g., at least about 2, 3, 4, 5, 6, 7, 8, 9, 10, or more electrode pairs) may be utilized in association with an enzyme or other moiety for which label binding may be desired. In some cases, some or all of the electrode pairs may have a same or a different gap therebetween.

In some cases, a system may comprise a single sensor. A single sensor may be configured to monitor or detect a single enzyme and or target analytes. In some cases, multiple enzymes and or target analytes may be detected or monitored simultaneously or sequentially by a single sensor. In some cases, a system may comprise a plurality of sensors, for example, greater than or equal to about 2, 3, 4, 5, 6, 7, 8, 9, 10, 20, 30, 40, 50, 60, 70, 80, 90, 100, or more sensors. Each sensor may be configured to monitor or detect one or more enzymes and or target analytes.

In some cases, systems of the present disclosure may comprise a blocker (e.g., a physical blocker). A physical blocker may be configured to achieve a higher percentage (e.g., greater than or equal to about 35%, 40%, 50%, 55%, 60%, 65%, 70%, 75%, 80%, 85%, 90%, 95%, or more) of electrode pairs with a single enzyme or other moiety associated thereto instead of a Poisson distribution. Non-limiting examples of physical blockers include a nanobead, nanorod, protein complex, DNA complex, carbohydrate polymer or carbohydrate complex, polymer, an adipocyte lipid droplet, a non-adipocyte lipid droplet, gold nanobeads, cellulose nanobeads, polystyrene nanobeads, latex nanobeads, or any other appropriately sized nanoparticle or combination of moieties which may create an appropriately sized nanoparticle. In some cases, only one physical blocker may be associated with an electrode pair.

In some cases, at least a portion of a physical blocker comprises a polymer, which may be a chimeric polymer, and may be of sufficient size as to comprise a physical blocker, or a significant portion of a physical blocker. In some cases, a polymer may be functionalized at a first terminus, and an enzyme may be bound to the functionalized terminus.

In some cases, a linker, which may be a polymer or chimeric polymer, binding an enzyme and a surface of an electrode structure, which may comprise an electrode pair, may comprise a nucleic acid polymer, and a nucleic polymer may comprise a sequence such that a secondary structure may be formed, and a secondary structure may serve to form a physical blocker which may be larger than a random sequence without secondary structure may otherwise form.

In some cases, an enzyme may be bound to a surface of an electrode structure which may comprise an electrode pair by one linker, or may be bound by more than one linker, while there may be a one to one correspondence between enzymes and physical blockers.

In some cases, a moiety to be observed may be loaded into a device along with a loading compound or loading reagent. A loading compound or loading reagent may then be removed prior to adding a moiety which interacts with a previously loaded moiety. In some cases, a loading compound may comprise a polynucleotide, and may further comprise a nucleotide bound with a primer. In some cases, a primer may be partially extended prior to loading. In some cases, a loading compound may be removed by providing nucleotides and allowing a first loaded moiety, which may be a polymerase, to fully extend and release a loading compound, which may be a polynucleotide; released loading compounds may thence be removed with any nucleotides, and target polynucleotides, which may be primed prior to introduction to a sensor volume, or may introduced with primers, wherein priming occurs within a sensor volume; primed polynucleotides may thence be bound by polymerases, and may thence be sequenced as described herein. In some cases, a loading compound may comprise natural DNA; in other cases, a loading compound may comprise non-natural DNA which binds to a polymerase.

In some cases, a system may optionally create a target complex. A target complex may comprise a polymerase or other appropriate enzyme, a sample nucleic acid strand or test or loading nucleic acid strand, and appropriate non-catalytic or catalytic divalent cations so as allow binding of the nucleic acid strand by a polymerase. A target complex may be introduced to an array of sensor electrode pairs, and may thence be bound to electrodes of an electrode pair. In some cases, a target complex may be bound to a dielectric which may comprise a material used to form a gap between electrodes of an electrode pair, which may be silicon nitride, silicon oxide, germanium oxide, or other standard semiconductor dielectric materials.

In some cases, a moiety which may be bound to a target complex may catalyze removal of other remaining binding sites, while a binding ligand used to bind a target complex may be left bound. For example, an exonuclease or nicking enzyme may be associated with other desired portions of a complex on a long linker. An exonuclease and or endonuclease enzyme may cleave portions of molecules (DNA in this example), such that binding of other complexes may be reduced or prevented. For example, an enzyme which may progressively cleave nucleobases from an end of a single stranded nucleic acid, or an enzyme that cleaves locations other than an end of a single stranded nucleic acid strand, but not a double stranded nucleic acid strand, may be effectively inactivated with respect to a strand binding a target complex by having a strand bound to a target complex hybridize to a binding moiety which may comprise a substantially complementary nucleic acid, thus forming a double stranded nucleic acid, which would not be degraded by the described enzymes.

In some cases, a sample or target nucleic acid strand or set of sample or target nucleic acid strands may be introduced to a chip in combination with a set of divalent cations such that a complex comprising at least a polymerase, a divalent cation, and a sample or target nucleic acid may be formed by complexing. Divalent cations may be catalytic or non-catalytic, and may be introduced to a fluid environment of a polymerase such that a divalent cation may bind to a catalytic active site of a polymerase prior to introduction of a sample or target nucleic acid, after an introduction of a sample or target nucleic acid, with a sample or target nucleic acid, or any combination thereof.

In some cases, a sample nucleic acid strand or test or loading nucleic acid strand, may comprise a complementary double stranded end, so that an enzyme with exonuclease activity may not degrade a sample nucleic acid strand or test or loading nucleic acid strand. A sample nucleic acid strand or test or loading nucleic acid strand may be protected from degradation by an endonuclease by utilizing a fully double stranded nucleic acid strand with a nick site at a point wherein a polymerase with strand displacement activity may be bound.

In some cases, an enzyme may be bound to a nucleic acid polymer or chimera polymer which may comprise nucleic acids using enzymatic binding, which may not be a sample or target nucleic acid. In some cases, a nucleic acid polymer may comprise a hairpin structure, thus allowing priming and thus enzymatic binding of individual enzymes to individual nucleic acid polymers or chimeric polymers which comprise nucleic acids. In other cases, an additional nucleic acid polymer may be provided, such that a primed nucleic acid structure may be formed, and may be bound enzymatically by, for example a polymerase.

In some cases, more copies of a nucleic acid polymers or chimera comprising a nucleic acid polymers may be provided relative to a number of enzymes, such that each enzyme may bind to a nucleic acid polymer or chimera comprising a nucleic acid polymer. In some cases, more copies of enzymes may be provided, such that each nucleic acid polymer or chimera comprising a nucleic acid polymer may bind with an enzyme, thereby forming an enzymatic binding. A separation step may thence be performed, such that the moiety provided at a higher concentration relative to a moiety provided at a lower concentration which does not bind to a moiety provided at a lower concentration may be removed from those moieties provided at a lower concentration, thereby providing a complex(s) of enzymes and nucleic acid polymers or chimera comprising nucleic acid polymers bound using enzymatic binding.

In some cases, a second terminus of a polymer may be bound to a magnetic or paramagnetic bead or particle. In other cases, a second terminus may be functionalized such that a second terminus may be bound to a surface of an electrode structure with an electrode pair.

In some cases, a second terminus may be bound to a magnetic or paramagnetic bead or particle, and a second linker may be bound to one of a magnetic bead or particle, an enzyme, or a linker binding a magnetic or paramagnetic bead or particle, and an enzyme. A second linker, which may be bound to a particular polymer of a first linker at one terminus, may be bound to a surface of an electrode structure which may comprise a pair of electrodes.

In some cases, a polymerase of other enzyme may be bound or associated with an electrode or utilizing a SAM, wherein a SAM, which may be bound to an electrode or set of electrodes, may comprise a mixture of moieties, and may comprise a mixture of different nucleic acids types, at least one type of which may be utilized as stuck end, and another may be utilized to bind a polymerase or enzyme. In some cases, effective melting temperatures between a nucleic acid which may comprise a stuck end and a nucleic acid which may comprise a moiety which binds a polymerase or other enzyme may be different, wherein a melting temperature of a nucleic acid which may comprise a stuck end may be less than an effective melting temperature of a nucleic acid which may comprise a moiety which binds a polymerase or other enzyme, and may be less by 1 degree Celsius, 2 to 5 degrees Celsius, 5 to 10 degrees Celsius, 10 to 20 degrees Celsius, 20 to 30 degrees Celsius, or greater than 30 degrees Celsius for a given same set of conditions, which may include salt concentrations, temperature and solvent. In other cases, a SAM which may bind an enzyme or polymerase may be bound to a dielectric, which may be a dielectric which may serve as a spacer to separate the electrodes of an electrode pair.

In some cases, an operating temperature which may allow for denaturation of a sticky end from a stuck end may allow a polymerase or other enzyme to remain hybridized, and thus may allow an exchange of label types or removal of labels while retaining bound polymerases or enzymes.

In some cases, a polymerase or enzyme which may be hybridized to a part of SAM which may be complementary to a nucleic acid which may be bound to the polymerase or enzyme, and may thence be ligated to a SAM, wherein a SAM may comprise a nucleic acid which may be partly single stranded and partly double stranded, such that a nucleic acid bound to a polymerase or enzyme may be ligated to a SAM, or a nucleic acid which may be bound to a polymerase or enzyme may be partly double stranded, and partly single stranded, such that a nucleic acid comprising a portion of a SAM and a nucleic acid bound to a polymerase or enzyme may be ligated together.

Use of Tunneling Labels for Nucleic Acid Sequencing

In some cases, a nucleotide base identification method may include synthesizing a double stranded polynucleotide between two electrodes by means of a polymerase present in a vicinity of a gap between two electrodes, and detecting an increase in tunneling current between electrodes as nucleotide bases are incorporated or bound between two electrodes. A polymerase may be provided with a primed target nucleic acid strand, wherein a single stranded portion may provide a template for incorporation (addition) of complementary nucleotides, which may be nucleotides with tunneling labels.

In some cases, an enzyme or polymerase may be considered to be in a vicinity of a gap between two electrodes when a labeled moiety bound by an enzyme or polymerase may be able to bind or interact with both electrodes such that a measurable tunneling current may be detected as a result of an interaction of the label bound to a labeled moiety with both electrodes.

Incorporation or binding of a base with a tunneling label may cause an increase in tunneling current going from one electrode to another. Many other methods which may result in localization of labeled moieties are possible, including as nonexclusive examples, hybridization of the label of a labeled nucleotide, labeled probes, ligation of labeled probes, binding in a triple stranded formation of a labeled probe, binding of amino acids, which may be labeled by a ribosome.

Figure 2A:
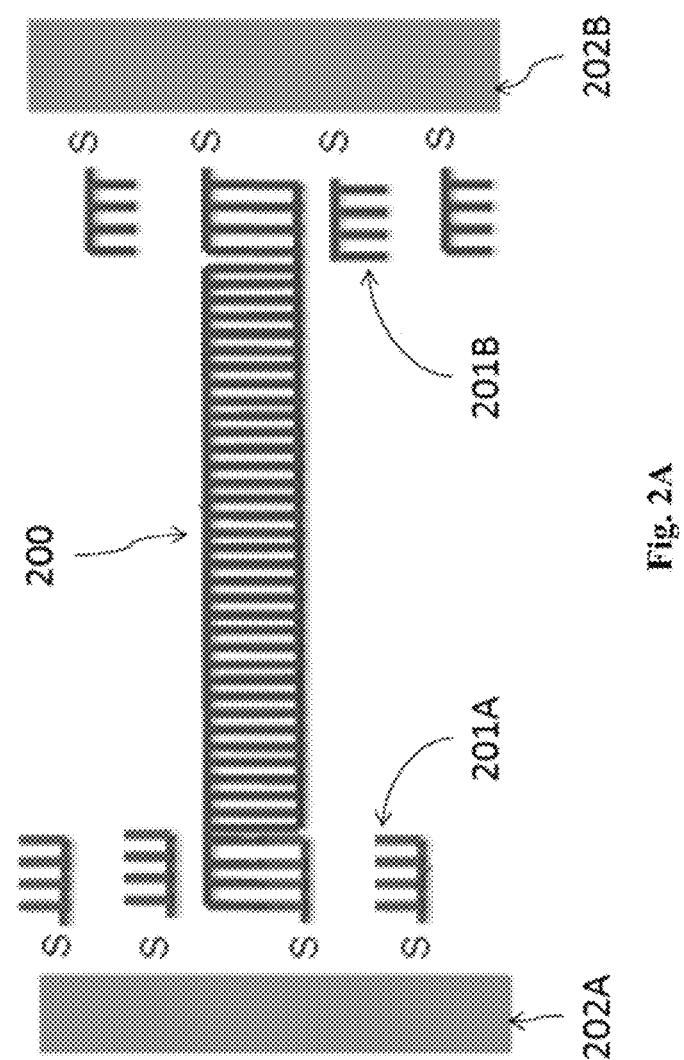
FIG. 2A shows a DNA label bound to two electrodes by the SAMs bound thereto.

A tunneling label may be a moiety or a single molecule, or a single molecule and a hybridized partly complementary nucleic acid polymer reversibly attached to a base that may be incorporated or bound, as shown in FIG. 2A wherein a tunneling label 200 is shown with its sticky ends bound to stuck ends 201A and 201B, which are bound respectively to electrodes 202A and 202B.

In some cases, different labels may be bound to different nucleotide bases and/or to different nucleotide base types. In cases where a nucleotide may be bound or incorporated by a polymerase in a vicinity of two electrodes, a tunneling current associated with an expected tunneling current for a tunneling label may be measured for different nucleotide bases, as a result of localization of a particular type of tunneling label, which may be associated with a base which may be complementary to a base being interrogated. Different tunneling labels may therefore be engineered to provide a convenient separation of tunneling current resulting from binding or incorporation of different nucleotide bases.

Figure 2B:
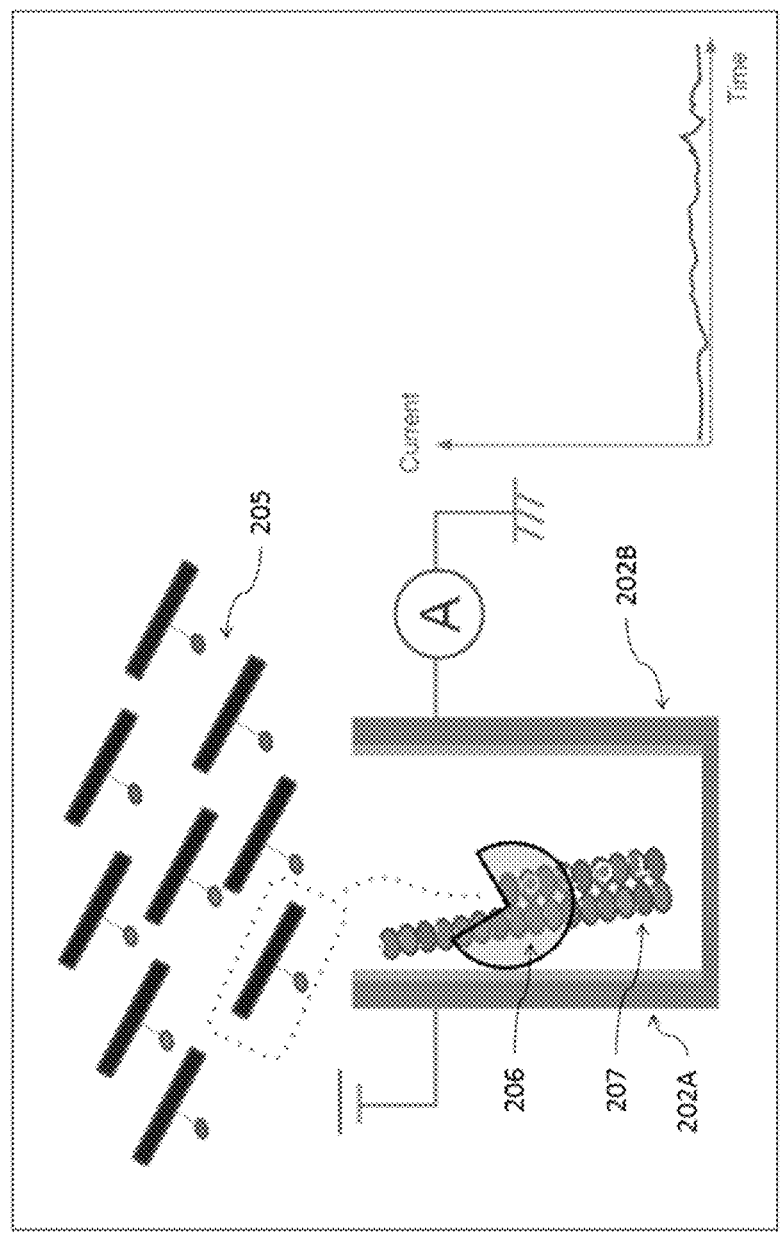
FIGS. 2B, 2C and 2D show different steps in a measurement process.

In some cases as shown in FIG. 2B, a set of nucleotides bound to labels 205 may be brought into the fluidic environment of a polymerase or other enzyme 206, which be complexed with a partially extended DNA strand 207 in a gap partly formed by electrodes 202A and 2.2B. During this time wherein no nucleotide and associated label 205 may be bound by a polymerase or other enzyme 206, essentially no current may flow between electrodes 202A and 202B.

Figure 2C:
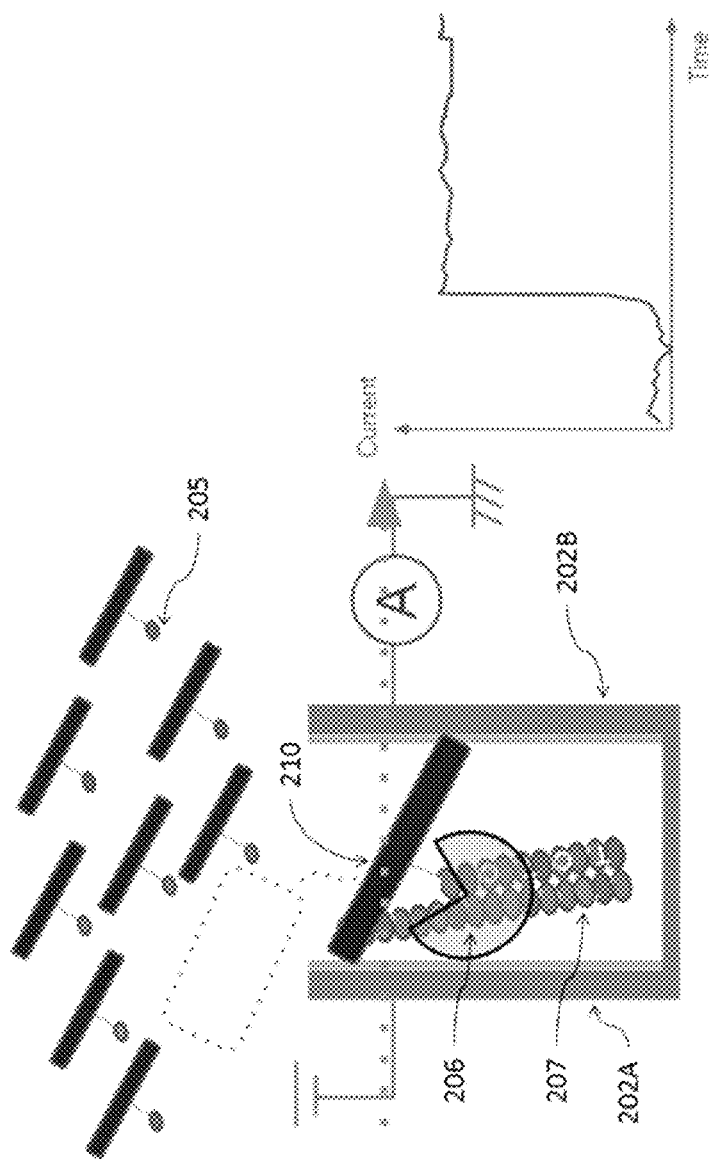
Figure 2D:
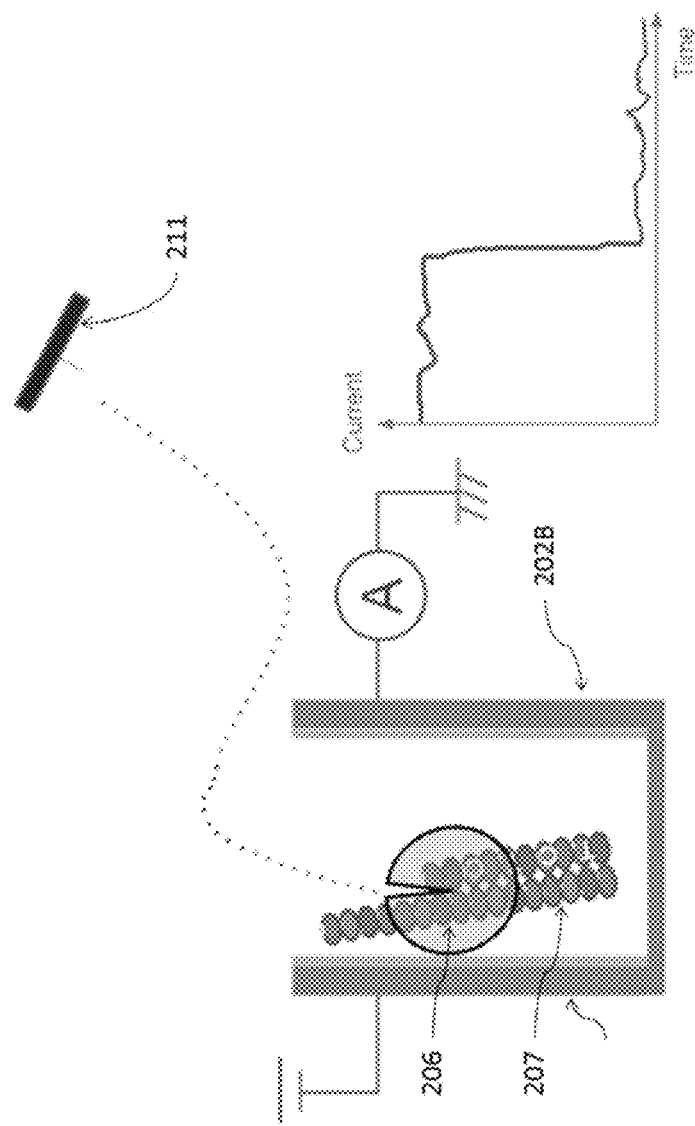

Thence as shown in FIG. 2C, a complementary nucleotide and associated label complementary 210 to an interrogated base of a partly extended DNA strand 207 of the set of nucleotides 205 may be bound by the polymerase or other enzyme 206 in a gap partly formed by electrodes 202A and 202B, thereby causing a current to flow between electrodes 202A and 202B. As shown in FIG. 2D, after removal of unbound nucleotides of the set of nucleotides with labels, a catalytic divalent may be brought into the fluidic environment of the polymerase 206 such that an incorporation of the nucleotide may be cleaved from the label of the complementary nucleotide 211, and the now unbound label of the complementary label 211 may washed away from the fluidic environment of the polymerase or other enzyme 206.

In other cases, a same label may be bound to more than one type of nucleobase. A nucleobase may be an unmodified nucleobase, or a modified nucleobase, wherein a binding time of a nucleobase may be different, so as to create a distinguishable difference in an average current.

In some cases, a label which may bind to a self-assembled monolayer (SAM) may be bound or associated with a nucleotide base. A label may be bound or associated with a 3' of a nucleotide, to a 5' of a nucleotide, to a base of a nucleotide, or to any combination thereof. A binding or association may be broken or dissociated as a result of an enzymatic process, as a result of a chemical step, such as a chemical or photochemical cleavage, or as a result of kinetics or temperature change.

In some cases, different types of bases which may have correspondingly different labels may be introduced into a system, e.g. in an aqueous solution. At a particular sensor, when one base may be incorporated or bound to a single strand via a complexed polymerase, a tunneling current may be used to identify what base or modified base has been bound or added using associated with differing tunneling currents associated with different labels corresponding to different nucleotide bases or modified nucleobases.

In some cases, once binding of a base with a label has been measured, a base with a terminator, which may be a 3' terminator, a 2' terminator, or any other type of terminator may be introduced to a system which may prevent further incorporation of additional nucleotide bases. This may prevent any phase error issues. This, in turn, enables utilizing long reads without worrying about phase errors.

A base with a label may be prevented from incorporation as a result of utilizing a buffer without appropriate catalytic cations required for incorporation, or may be prevented as a result of utilizing an unincorporable nucleotide, such as (without limitation) a nucleotide with substitutions in the phosphate chain such as replacing the alpha, beta or both phosphates with an arsenic, Sn, Bi or N, a PNA nucleotide, an L-DNA nucleotide, a locked DNA nucleotide, a ribonucleotide, an adenine monophosphate, an adenine diphosphate, an adenosine, a deoxyadenosine, a guanine monophosphate, a guanine diphosphate guanosine, a deoxyguanosine, a thymine monophosphate, a thymine diphosphate 5-Methyluridine, a thymidine, a cytosine monophosphate, a cytosine diphosphate cytidine, a deoxycytidine, a uracil monophosphate, a uracil diphosphate, a uridine, and a deoxyuridine. Generally, an unincorporable nucleotide may be bound by a polymerase, but not incorporated into a growing polynucleotide strand by a polymerase.

In other cases, once binding of a base with a label has been measured with a buffer which does not have appropriate catalytic cations for polymerase incorporation to occur, a buffer without catalytic cations may be replaced with a buffer which does not have incorporable nucleobases, but does have appropriate catalytic cations such as magnesium and or manganese. In some cases, a buffer used to bind but not incorporate nucleobases which contains nucleobases may first be replaced with a buffer which does not have incorporable nucleobases, and does not have catalytic cations useful for incorporation of nucleobases, while subsequently a buffer with catalytic cations may be introduced for the purpose of allowing incorporation nucleobases which may still be bound.

In some cases, subsequent to incorporation of nucleobases, a new buffer lacking catalytic cations with incorporable tunneling labeled nucleotides may replace a buffer which has catalytic cations. In some cases replacement may be performed in two steps, wherein a new buffer without incorporable nucleobases and lacking catalytic cations may be flowed to replace a buffer with catalytic cations, and subsequently a buffer lacking catalytic cations but with incorporable nucleobases with tunneling labels may be introduced.

In some cases a measurement process may occur while a buffer which tightly binds nucleobases is utilized with polymerases such that a polymerase effectively does not release a correct (complementary to a nucleobase on a target strand) nucleobase after binding of a correct nucleobase. Such a buffer may comprise at least in part calcium ions, but may not comprise other non-catalytic cations capable of occupying a catalytic metal binding site, in some cases, a buffer which tightly binds nucleobases may bind and not release a nucleobase after binding of a nucleobase until conditions are changed. In other cases, a buffer which may comprise calcium and other metals which may occupy a polymerase catalytic binding site, but which allow a polymerase to release a complementary bound nucleobase. Such other metals may comprise at least in part zinc, barium, strontium or other divalent metal cations. Modified bases may be incorporable or may be unincorporable. Modified bases may comprise tunneling (or other labels such as fluorescent labels) labeled naturally occurring epigenetically modified bases, or may be tunneling (or other labels such as fluorescent labels) labeled non-naturally occurring nucleobases. Thus in some cases, more than four label types may be used.

In some cases, kinetics of nucleotide binding, and complementarity to an interrogated base may be measured as a function of a current effectuated by associated tunneling tags, whereby differences in modifications or lack thereof of complementary nucleobases may be measured as a function of binding kinetics. In some cases, modified labeled nucleobases may be utilized which may bind for a longer or shorter time to non-epigenetically modified bases or to epigenetically modified bases. In some cases, detection of oxidation of guanine, which may be DNA guanine or RNA guanine, may be detected when the guanine base is oxidized to 8-hydroxyguanine by changes in relative binding efficiencies to adenine, whereby upon being oxidized, kinetics of binding to adenine becomes similar to kinetics of binding to cytosine.

In some cases, a single nucleotide type may be added to a system for incorporation at a time. In this case, there is no need for different labels corresponding to different nucleotide bases to have different tunneling current characteristics. Instead, one looks to see if incorporation or binding has happened. If an expected tunneling current is registered, a type of the complementary base may be identified and a polynucleotide may be sequenced in this fashion. In other cases, a single labeled incorporable nucleotide may be combined with other nucleobases, wherein the other nucleobases may be unincorporable as previously described hereinabove. In some cases, a single nucleotide type may be added to a system for incorporation at a time. In this case, there is no need for different labels corresponding to different nucleotide bases to have different tunneling current characteristics.

In some cases, four or more different types of nucleobases may be provided, wherein at least a subset of nucleobases may be provided with tunneling label compounds bound thereto to triphosphates, and nucleobases may be unterminated. A reaction may thus occur without the need for addition of nucleobases, wash steps etcetera, except as needed to replenish concentrations of nucleobases. Nucleobases may be provided with catalytic metal cations such as magnesium and manganese, and may further be provided with noncatalytic cations such as calcium, zinc and other divalent cations as described herein, such that kinetics of polymerase binding and incorporation may be slowed so that binding and incorporation kinetics may be more easily observed and measured.

In other cases, a multistep method may be utilized, wherein nucleobases provided may have tunneling label compounds reversibly bound to a base portion of a nucleobase instead of being bound to a ribose portion of a nucleobase. In some cases, a terminator as described herein may be provided, which may be bound to the 3' of the ribose of nucleobases.

In some cases, a set of nucleobases which may have bound tunneling label compound(s) and 3' terminators may be provided such that a single base extension reaction is effectuated. In some cases, remaining nucleobases may be removed prior to reading of electrode pair sensors to determine whether and which of different tunneling label compounds may be bound as part an extension reaction; in other cases, measurement may be effectuated before removal of nucleobases, as background from presence of remaining nucleobases does not significantly interfere with a determination of whether and as appropriate which tunneling label compounds may be bound to an extended strand.

In some cases, a tunneling label may be bound to a terminator. In some cases, a tunneling label may be bound to a phosphate chain. In some cases, a label may be bound to a base using a cleavable linker which is not a terminator.

In some cases, terminators and labels may be simultaneously removed from a extended strand using a single chemical step, such as a Tris(2-carboxyethyl)phosphine hydrochloride cleavage step. In other cases, cleavage of tunneling label compounds and terminators may occur as a result of separate reactions. In some cases, several sets of nucleobases may be utilized and allowed to bind to polymerase complexes. Nucleobases sets may comprise unmodified bases, modified bases, or combinations of modified and unmodified bases.

In some cases, wobble base pairings may be utilized as a part of a set, wherein wobble pairings may include guanine-uracil (G-U), hypoxanthine-uracil (I-U), hypoxanthine-adenine (I-A), and hypoxanthine-cytosine (I-C), among other wobble base pairings. In some cases, a wash step may be effectuated prior to introduction of nucleobases as described hereinabove and thus begin an additional cycle of sequencing. In some cases, terminators may comprise 3'-ONH3 groups, 3'-O-allyl groups, 3'-O-azidomethyl groups, or may comprise combined terminator and tunneling label compound similar to a Virtual Terminator™ which utilizes fluorescently labeled nucleobases such as those used by Helicos, or may utilize a combined terminator and tunneling label compound similar to a Lightning Terminator™ which utilizes fluorescently labeled nucleobases such as those used by LaserGen.

In some cases, nucleobases may be provided with tunneling labels bound to a phosphate chain, which may be extended from a tri phosphate to a tetraphosphate, pentaphosphate, hexaphosphate, septaphosphate, or longer phosphate chains, and may further comprise a linker which may comprise an alkane or poly(ethylene glycol) or other appropriate linker chain, which may be configured to be flexible as an alkane chain may be, or may be configured to be comparatively inflexible as an alkyene chain may be.

In some cases, a single tunneling label may be used for all bases. Nucleobases may then be introduced, wherein one or more bases may be labeled, and other bases may not be labeled. Some or all bases may be unincorporable. Catalytic divalent metal cations may not be provided thereby preventing incorporation. Different sets of nucleobases may thence be provided in turn, such that different types of nucleobases may be labeled, and other bases may be unlabeled at time, so that utilizing Boolean logic a base complementary to a next target base may be determined. Sets of bases may be washed out using a reagent solution which may not contain sufficient quantities of divalent cations appropriate for binding nucleobases. A reagent solution may comprise cations, which may be useful for retaining hybridization of sample DNA and primers or extended primers. A subsequent set of nucleobases to be tested may thence be brought such that a subsequent set of nucleobases may interact with and bind with polymerase complexes. A subsequent set of nucleobases may further comprise one or more divalent cations, such that subsequent nucleobases may bind for substantially longer than subsequent nucleobases would bind in the absence of divalent cations.

One or more sets of incorporable terminated or unterminated nucleobases may then be provided with or without catalytic metal cations respectively, such that a single base may thence be bound or incorporated, remaining nucleobases removed, and catalytic metal cations provided such that a bound base may be incorporated as needed.

In some cases, no clonal amplification may be required as single molecule detection may be used; in other cases, a clonal population may be used to increase signal levels, and set of polymerases may be associated with one or more localized clonal populations which may be in the vicinity of one or more electrode pairs.

In some cases, a method of the present disclosure may include:
  a) introducing labeled nucleotides and divalent calcium and subsequent binding of nucleotides;
  b) removing unbound labeled nucleotides, using a divalent calcium wash solution; c) reading labels of bound nucleotides, thereby determining which nucleotide is bound at each sensor;
  d) incorporating bound nucleotides by introduction of magnesium and or manganese; and
  e) removing magnesium and or manganese using a calcium wash solution.

Figure 2E:
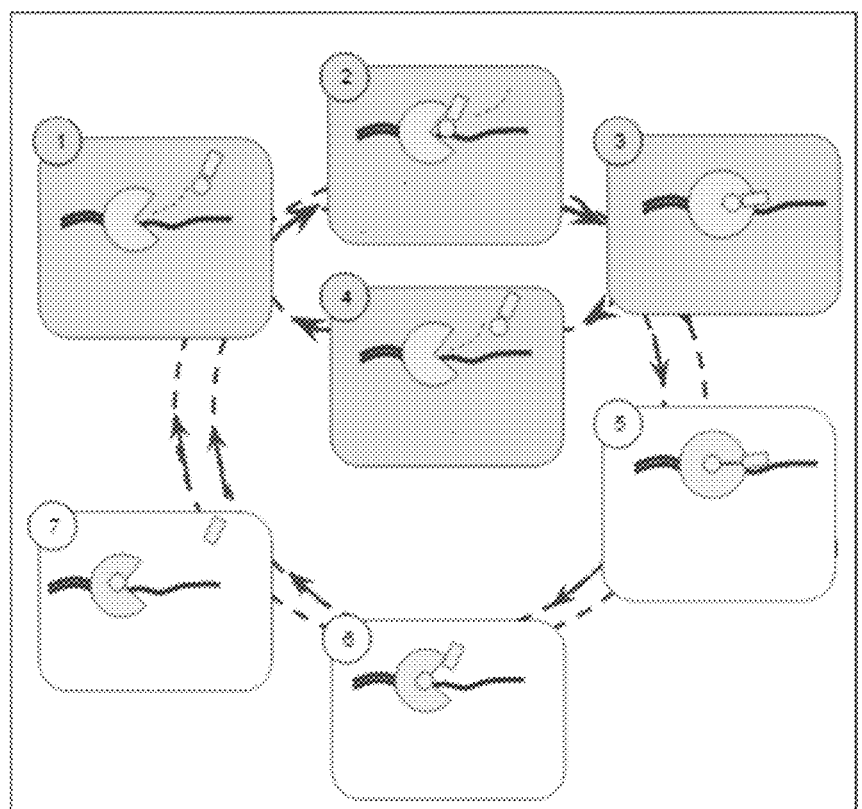
FIG. 2E shows a process flow diagram for a polymerase and associated sequencing method.

In some cases, a method of the present disclosure may include:
  a) introducing one or more labeled nucleotide types and optionally one or more unlabeled nucleotides, which may be naturally occurring nucleotides including epigenetically modified nucleotides, or synthetic nucleotides, in a mixture comprising calcium and optionally other non-catalytic divalent cations;

b) measuring label(s) in calcium and optionally at least one other non-catalytic divalent cation; determining label type and optionally label kinetics;
c) washing out label(s) with at least a divalent cation other than calcium, magnesium and manganese; and optionally repeating steps a), b) and c) using different label nucleotide combinations, which may include other types of nucleotides;
d) introducing a set of optionally unlabeled nucleotides to be incorporated in a calcium buffer, which may be canonical bases or may be epigenetically modified bases or synthetic bases, so as to bind the nucleotides'
e) washing out unbound nucleotides with a calcium buffer wash;
f) introducing magnesium and or manganese buffer and incorporate bound nucleotides; and
g) removing magnesium and or manganese buffer with a buffer which does not contain magnesium and or manganese, which may comprise other divalent cations Such a process is shown in a process flow diagram in FIG. 2E, wherein in step 1, a polymerase may be introduced to a set of nucleotides, which may be bound in step 2, whereupon in step 3 the polymerase may undergo a conformational change and may close between thumb and palm securely binding a nucleotide; thence the polymerase may undergo another conformational change and may open in step 4 wherein the bound nucleotide is allowed to be released, and moving back to step 2; these steps 1-2-3-4-1 may be repeated several times prior to step 5 wherein a phosphoryl transfer may occur with concomitant nucleotide incorporation, followed in step 6 of the release of the pyrophosphate after a conformational change by the enzyme opening the thumb from the palm and associated label, followed in step 7 by the movement of the polymerase to the next base to be interrogated and the diffusive migration of the pyrophosphate and label from the fluidic environment of the polymerase.

Figure 2F:
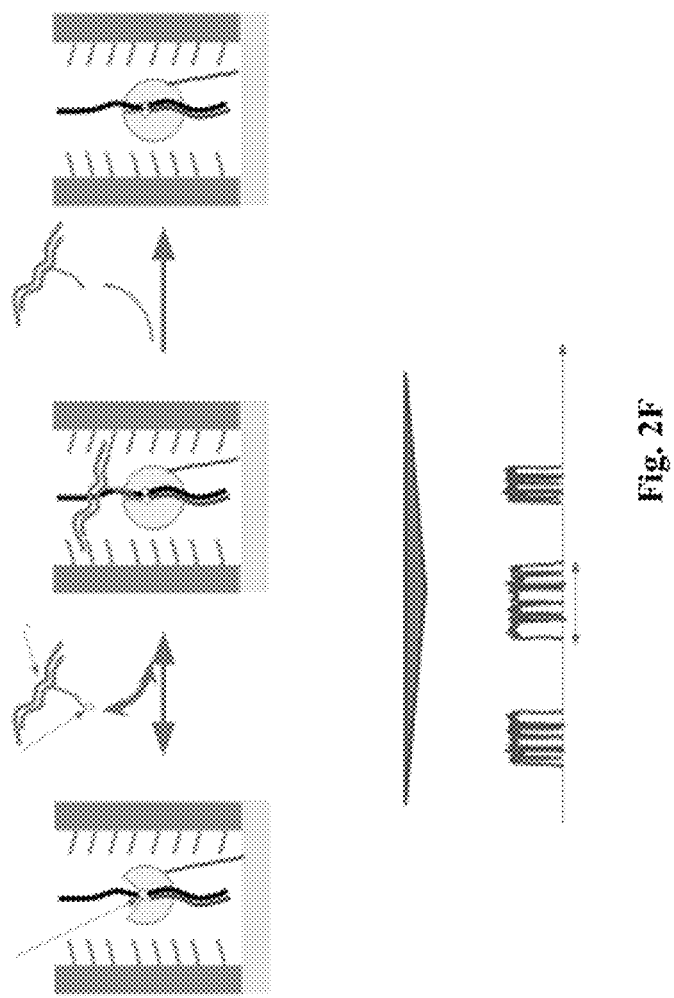
FIG. 2F pictorially shows the several steps of an epigenetic sequencing method and resultant current.

This situation is also shown pictorially in FIG. 2F wherein a labeled nucleotide is shown between two states (left and middle structures with associated polymerase) corresponding to states 1 and 3 of FIG. 2E, wherein in the center state the labeled nucleotide is bound by the polymerase, and is held for a time while the label may bind and release from the stuck ends bound to the electrodes, which may be at least partly as a result of ion exchange in the polymerase between a cation which may fixedly bind the nucleotide, and one which may allow release of the nucleotide; after a desired period of time, the buffer mixture may be exchanged, resulting in a single nucleotide being bound by the polymerase, without other nucleotides in the fluidic environment of the polymerase, and the buffer may be changed to include at least a divalent cation which may allow the polymerase to incorporate the bound nucleotide, thus reaching the state shown in the right hand structure. The current produced may thus be depicted by the trace shown in the bottom of FIG. 2F, wherein there may be clumps of short pulses, wherein the clumps correspond to time periods wherein a nucleotide may be bound by a polymerase, and the short pulses in the clump may correspond to the time periods during when the nucleotide may be bound by the polymerase and may also be hybridized to the stuck ends.

In some cases clumps of current pulses which result from hybridization may come only while a nucleotide is bound, and each clump may vary in width, time between clumps, and average current magnitude of clumps. In other cases, in a manner similar to nucleotide binding, a width of a pulse and time between pulses can vary significantly. An average current magnitude may also change for a same label or label type, either in a single sensor or in between different sensors; in some cases different crystal planes, different widths of electrode spacings and concomitant angles between double stranded sections such as hybridized stuck and sticky ends and double stranded central portions of labels, and resultant current may be different depending on which sticky end of a set of accessible sticky ends a particular hybridization happens to utilize. In further cases, stray pulses may result from other stray nucleotides. This may give a single stray pulse, or, less often, a small set of pulses, which may result in an average background current with an associated distribution of current. Such background currents may be characterized, normalized and removed from measured signals, wherein such normalization may be performed on a global basis, an individual sensor basis, or an appropriate intermediate level of normalization.

In some cases, simultaneous detection, and formation and reformation of complexes may be utilized using several different labeled nucleotides. Different nucleotides may have different enzymatic binding kinetics, different hybridization binding kinetics, different label conductances, or combinations thereof.

In other cases, quantitation by a level of signal may result from kinetics, wherein an average current over a period of time may indicate a type of label, and thus may indicate an associated nucleotide type to which a label may be bound, and an average time period for which a label may be bound, for example, to a complex which may comprise a polymerase, primed nucleic acid, and nucleotide comprising a label. A current level may vary as a result of the $K_{on}$ and $K_{off}$ for one or more different nucleotides and associated labels.

In some cases, one or more types of enzyme with phosphatase activity may be included with a reaction mixture, such that one or more enzymes with phosphatase activity may reduce a number of hydrolyzed bases and thus prevent or reduce a number of normally labeled bases bound by a polymerase enzyme which are not labeled, or bases which should be incorporable, which are not incorporable due to truncated phosphate chains. In other cases, an anticipated average current may compensate for lack of signal due to hydrolyzed bases by tracking average signals and compensating for increased levels of hydrolysis; compensation may be done using a curve or formula for expected increase in a number or percentage of hydrolyzed bases, or may be derived from measured current levels.

The Use of Tunneling Labels for RNA Sequencing

In some cases, RNA dependent RNA polymerases may be utilized for a RNA sequencing extension experiment, such as RNA dependent polymerases utilized by RNA viruses, such as polioviral 3Dpol, vesicular stomatitis virus L, and hepatitis C virus nonstructural NS5B protein, or eukaryotic RNA dependent RNA polymerases.

In some cases, wherein a sample RNA strand may be sequenced or may have a sequence determination or quantitation assay performed, an RNA ligase may be used to bind universal primers or primers which also comprise a barcode, such as T4 RNA ligase 1, which may be useful for binding ssRNA primers, or primers which may comprise a barcode, to a sample ssRNA strand, or T4 RNA ligase 2, which may be useful for binding hairpin RNA primers or primers which may comprise a barcode and may be chimeric such that a primer may further comprise DNA ligated to a sample ssRNA strand.

In some cases, a reverse transcriptase may be utilized, such as HIV reverse transcriptase such as HIV-1 or HIV-2 reverse transcriptases, a commercial reverse transcriptase such as Affinityscript (Agilent) (Arezi and Hogrefe 2009), Maxima (ThermoScientific), Rocketscript™ (Bioneer), Thermoscript™ (Life Technologies), and Monsterscript™ (Illumina) or (AccuScript; Stratagene), a non-LTR-retrotransposon, or a group II intron reverse transcriptase such as those from *Lactococcus lactis* and *Thermosynechococcus elongatus*, a high accuracy reverse transcriptase such as RTX (reverse transcriptase xenopolymerase), or Phi6 RNA polymerase.

In some cases, a reverse transcriptase stop may result during a sequencing step. A base causing a reverse transcriptase stop, which may be a naturally occurring base, or may result from a binding as described hereinafter, may be identified, or may simply be identified as a reverse transcriptase stop position, wherein a base cannot be identified as a result of a binding moiety. Multiple sequencing steps may occur wherein repeated reads of a same location with a reverse transcriptase stop may occur prior to a step whereby one or more of removing of a binding moiety or providing of a base which may base pair with a modified base, thus permitting incorporation of a complementary base and subsequent further extension of a complementary strand being extended.

In some cases, a reverse transcriptase stop may be effectuated by a reverse transcriptase. A reverse transcriptase stop may result from the inability of a RNA dependent RNA polymerase or a DNA dependent DNA polymerase being unable to incorporate a complementary base either due to base modifications, or due to binding moieties being bound to a base causing a reverse transcriptase stop.

In some cases, a reverse transcriptase stop may result from a naturally occurring modified base, or by an oxidized base. A subsequent sequencing step may utilize a modified base which may be able to base pair with a base which caused a reverse transcriptase stop.

In other cases, a reverse transcriptase stop may be effectuated by one or more antibodies, enzymes other molecules, or combination thereof preferentially binding with or interacting with one or more modified bases. A subsequent sequencing step may utilize a modified base, which may base pair with a modified base which caused a reverse transcriptase stop in order to allow incorporation of a base and to allow further extension of a complementary strand. In some cases, antibodies, enzymes or other molecules may be removed by a processing step, thus allowing further extension of a complementary strand.

In some cases, a sequencing method which may be a skip read method may be utilized, whereby additional primer extension during a skip period may be caused to cease as a result of a reverse transcriptase stop. A subsequent step may identify a modified base which caused a reverse transcriptase stop, followed by sufficient sequencing steps as to identify a location of a reverse transcriptase stop and causative modified base.

In some cases, particularly wherein an RNA or DNA dependent polymerase may not have displacement activity, or may have weak strand displacement activity, an RNA or DNA helicase may be used in combination with DNA dependent polymerase, RNA dependent RNA polymerase or reverse transcriptase to aid in reading through secondary structure, or to displace a complementary strands, miRNAs, lncRNAs, or other moieties which may be bound to a target DNA or RNA strand.

In some cases, a DNA or RNA helicase may be bound through a linker to a DNA polymerase, reverse transcriptase or RNA dependent RNA polymerase so as to improve the likelihood of conjoint operation, thus better removing secondary structure. In some cases, a DNA or RNA helicase may be provided unassociated with a DNA polymerase, reverse transcriptase or RNA dependent RNA polymerase. In some cases, in addition to a DNA or RNA helicase in association with a DNA polymerase, reverse transcriptase or RNA dependent RNA polymerase, additional polymerase helper proteins may be added, such as single stranded binding proteins. In some cases, ribosomes may be utilized instead of polymerases, whereby sets of labeled tRNAs may used to decode codons, and thereby give a codon map of an mRNA, and or providing direct monitoring of translation. In some cases, ribosomes may be utilized with labeled amino acids, thereby allowing direct monitoring of translation.

The Use of Tunneling Labels for Other Sequencing Methods

In some cases, a system for tunneling and or hopping detection may use a method which may comprise the use of RNA dependent RNA polymerase, DNA dependent DNA polymerase, or reverse transcriptase to create a second strand, wherein a hairpin primer may be ligated at one or both ends of an RNA strand using RNA dependent and or DNA dependent ligases and or engineered ligase which can ligate either RNA or DNA to create a circularized strand which may be repeatedly read using the polymerase and labels.

In some cases, a ribozyme may be utilized as an RNA dependent RNA polymerase, which may include modified ribozymes such as ribozyme 24-3 or other modified ribozymes. In some cases, other cations other than Mg, such as manganese or other divalent cations may be used to catalyze an incorporation reaction which may utilize a nucleobase. A nucleobase may comprise canonical, epigenetically modified, or synthetic nucleobases, which may comprise a ribose sugar, or may comprise a backbone of any other kind as described herein. In some cases, non-catalytic cations, other than Ca, may be used to hold a nucleotide, which may comprise canonical, epigenetically modified, or synthetic nucleobases, and which may comprise a ribose sugar, or may have a backbone of any other kind as described herein.

In other cases, a DNA or RNA ligase may be used to ligate universal primers or primers which may comprise a barcode. Primers may be a single stranded primer, double stranded primer, or a hairpin primer. In some cases, an assay may utilize both RNA and DNA ligases, for example for a single sample, which may comprise both RNA and DNA in a same sample, for example to allow sequencing of both RNA and DNA from a same sample. RNA and DNA ligases may be utilized with different aliquots of a sample in different reaction volumes. Different reaction volumes may be in different areas of a chip, in different chips, or in a separate fluidics device. RNA and DNA ligases may be utilized for a single sample in a common reaction volume or volumes, which may be in an area of a chip, in different chips, or in a separate fluidics device.

Long Reads

In some embodiments, it may be desirable to utilize long reads or multiple reads with separations therebetween when sequencing repetitive sequence regions which might otherwise create ambiguous sequence assemblies. In some cases, an array of sensors may allow a skip period of a skip read method to progress at different rates in different portions of a chip or chips. A difference in rate may result from differences in available concentrations of incorporable nucleotides, differences of concentrations of unincorporable nucleotides, temperature, types or variants of polymerase, or any other methods to affect kinetics of incorporation.

In cases where a long read is desired, an assay may provide one or more different types of nucleotides while provided with catalytic cations such as magnesium and or manganese for a period of time. Data may or may not be collected. A sequence may or may not be determined, or may be partially determined. During a period of time, an incorporation rate may be much higher than would be possible with other methods, whereby cycles of noncatalytic periods, catalytic periods, and wash periods may be utilized in alternation.

In some cases, unlabeled, or a mixture of labeled and unlabeled nucleotides may be utilized during a time period which may quickly extend a primer, but may or may not provide high quality sequence data. In some cases, alternatively or additionally, labeled, and or unlabeled nucleotides may be utilized in combination with terminated bases, where terminated bases may result in preventing a polymerase from further extension. In some cases, all four non-terminated base types (AGCT) may be provided, with a single type of terminated base. In some cases, less than or equal to about three non-terminated base types may be provided with one or more terminated base type. A terminated base type(s) may comprise one or more base types which are not provided in a set of unterminated bases. Terminated base type(s) may comprise one or more base types which are provided in a set of unterminated bases. Terminated base type(s) may comprise a combination of bases which may be provided in a set of unterminated bases and bases which are not provided in a set of unterminated bases. In other cases, different sets of non-terminated and or terminated bases may be used, where different base types may be terminated or unterminated in different sets of bases.

Terminated bases may have terminators removed, and a same set of bases, or a different set of bases may thence be provided, or a set of cycles as described whereby non-catalytic, catalytic, and wash cycles may be utilized. Terminated bases may comprise ribose 3', or 2' terminators, or may comprise virtual terminators, or Lightning Terminators™.

In some cases, non-catalytic divalent cations may include calcium, scandium, titanium, vanadium, chromium, iron, cobalt, nickel, copper, zinc, gallium, germanium, arsenic, selenium, rhodium, or strontium, or mixture of these elements. Catalytic cations may be provided with a concentration which permits association of divalent cations with dsDNA. A dsDNA may comprise labels, extended primers or other sources of dsDNA which may be in a flow cell, as well as providing additional catalytic divalent cations for binding to polymerase and or other enzymes.

In some cases, a DNA polymerase may be utilized with DNA nucleotides. In other cases, an RNA dependent RNA polymerase (RdRP or RDP) or RNA replicase such as phi6 RNA polymerase may be utilized with RNA nucleotides. In some cases, a primer may be provided. In cases where an RdRP is utilized, no primer may be provided, and the polymerase may self prime. In some cases, detection of RNA secondary structure using kinetics may be performed.

In some cases, nucleic acid polymers or chimera comprising nucleic acid polymers may serve as enzyme blocking moieties, and may be removed after binding of enzymes to electrode structures, which may comprise an electrode pair. An enzyme blocking moiety may block extension of a primer, for example, by a polymerase which may not have strand displacement activity. Such an enzyme blocking moiety may, for example be synthesized such that standard phosphodiester bonds are not utilized, and another linkage may be utilized which may not be cleaved by an exo activity of a polymerase, such as a sulphodiester, thiodiester, or arsenodiester bond, or a phosphothioate, and may have a bond, or may comprise a moiety which may not be readily degraded by an exonuclease at one or more locations in a nucleic acid polymer, which may include a first base which might be cleaved by an exonuclease activity of a polymerase or other enzyme.

In some cases, removal of nucleic acid polymers or chimera may be effectuated by providing conditions, which may include temperatures divalent cation concentrations, and pHs, thus facilitating removal of nucleic acid polymers or chimera which may comprise nucleic acid polymers used as enzyme blockers from enzymes, and may be combined with other polymers, which may serve as enzyme blockers to prevent access by a subsequent complex, thereby allowing subsequent introduction of sample nucleic acids, and further sequencing or sequence identification of sample nucleic acids.

In some cases, nucleic acid polymers or chimera, which may comprise nucleic acids, may have a nick site with a second strand spanning the nick site, such that after binding of an enzyme blocker enzyme complex to an electrode structure, nucleotides may be provided, and an enzyme, which may have strand displacement capabilities, may extend the nucleic acid polymer or chimera which may comprise a nucleic acid polymer, displacing a second strand, and thence releasing the nucleic acid polymer or chimera which may comprise a nucleic acid polymer.

In some cases, nucleic acid polymers or chimera which may comprise nucleic acids may have a nick site with a second strand spanning a nick site, such that after binding of an enzyme blocker enzyme complex to an electrode structure, temperature and other conditions, such as salt concentrations may be changed, so that a second strand may be denatured, while retaining functionality of an enzyme. In some cases, nucleotides may then be provided, and an enzyme, which may not have strand displacement capabilities, may extend a nucleic acid polymer or chimera which may comprise a nucleic acid polymer, thus releasing the nucleic acid polymer or chimera which may comprise a nucleic acid polymer.

In some cases, an enzyme blocker or linker may comprise a nucleic acid polymer, and a nicking enzyme may be used to cleave a nucleic acid polymer at a specific location and release the enzyme blocker or linker from, for example, a surface. In some cases, an enzyme blocker or linker may comprise an amino acid polymer, and a site specific endoproteinase may be used to cleave the amino acid polymer at a specific location (or site) and release the enzyme blocker or linker from, for example, a surface. In some cases, an enzyme blocker or linker may comprise a portion thereof which may be selectively cleaved using a chemical cleavage instead of a biochemical cleavage.

In some cases, in order to increase effective coverage, a nicking process may be repeated, allowing re-reading of a previously extended sample strand. In other cases, a chemically cleavable linkage may be utilized, either in addition to, or instead of a nick site so as to allow a nick to be formed.

In some cases, one or more moieties, which may have phosphatase activity, may be provided in conjunction with a set of labeled nucleotides; such moieties may include phosphatases such as shrimp alkaline phosphatase, nucleotideases and various other known enzymes and chemical cleavage agents. Such a moiety with a phosphatase activity may prevent the binding and potential incorporation of a labeled nucleotide type which has been hydrolyzed such that it may be unlabeled and may potentially be incorporated.

In further cases, in order to compensate for changing percentages of unlabeled nucleotides relative to labeled nucleotides, particularly in a method which may measure a number of different nucleotide binding rates in order to determine a type of interrogated base, which may include determination of, for example, interrogated base methylation status, measurements of known bases and or measurements of histograms may be utilized to compensate for changing average signal levels which may result from an changed percentage level of unlabeled nucleotides, and or for other purposes such as errors in temperature control, salt concentration or other factors which might affect kinetics and or signal level of a measurement. In further cases, previously measured and thus assumed changes in signal level may be utilized to compensate for expected changes in signal level over a length of a run.

In some cases, RNA or DNA epigenetics may be determined. In other cases, both RNA and DNA epigenetics may be determined by a part of a single system. RNA and DNA epigenetics may be determined in different volumes of different chips, in different volumes of a single chip, or in a common volume in one or more chips.

In some cases, RNA and or DNA epigenetics may be determined for a single cell or set of cells which have been isolated, for example, by flow cytometry, to have a consistent characteristic, such as size, roughness or specific binding sites, to which an antibody or aptamer may be bound for identification, separation, and isolation.

In some cases, in order to stop at a desired location, or to limit a length of a series of incorporation events that may be otherwise unregulated, polymerase incorporation may be stopped by the use of, for example probes which cannot be removed by polymerase action, such as strand displacement, or 3' to 5' exonuclease activity. Such a probe may be a targeted probe, or may be a random probe. A probe may comprise a sulfur group, such that a 3' to 5' exonucleases activity may be inhibited, or may utilize an uncharged locked DNA so as to prevent a strand displacement activity from being able to displace a probe. A wash procedure may thence be utilized to remove nucleobases and or catalytic divalent cations. For example, the temperature may be raised, and or salt concentration may be reduced to allow for removal of the probe(s). A sequencing method as described herein may then be commenced, or re-commenced.

In some cases, salt concentrations and or integration times used to observe the binding and or kinetics of different sets of nucleotides as described hereinabove in optionally repeated steps a) and b) as described hereinabove may be the same for different sets of nucleotides. In other cases, a salt concentration and or integration time may be different for different sets of nucleotides as desired, for example, to reach a desired confidence level associated with epigenetic modification detection.

In some cases, tunneling and or hopping detection may utilize a method which may only make use of canonical bases, or other bases, which may be naturally occurring epigenetic bases or synthetic bases, as determined to provide lowest incorporation errors when considering either an incorporation of a particular base or an adjoining base when using a particular RNA dependent RNA polymerase, DNA dependent DNA polymerase, or reverse transcriptase to extend a primer and thereby form a second strand, which may be an RNA, DNA or cDNA strand. In some cases, additional modified bases may be utilized to prevent stalling of polymerizing enzyme, such as reverse transcriptase, as a result of epigenetic modifications such as $N^1$-adenosine, $M^3$-methylcytosine, $N^1$-methylguanosine, or other modified bases which may result in lower binding or steric hindrance.

In some cases, epigenetic modifications for tRNAs may be utilized, while in other cases, tRNA with different epigenetic modifications may be utilized. Similarly, unmodified amino acids may be utilized, while in other cases, epigenetically modified amino acids may be utilized.

In some cases, a modified base specific binding moiety may be utilized. A modified base specific binding moiety may comprise an m6A binding protein such as YTHDF1, YTHDF2, YTHDF3, or YTHDC1. A modified base specific binding moiety may be utilized in combination with one or more sets of nucleotides as a part of determining a base and or epigenetic modifications thereof. A modified base specific binding moiety may comprise a tunneling label. A modified base specific binding moiety may be unlabeled, but may influence kinetics of binding and or times between binding events of other labeled moieties such as labeled nucleotides. In other cases, modified or synthetic bases may be used in order to prevent reverse transcriptase stops, thereby limiting or eliminating truncation of production of cDNA, and thus permitting reading of a complete, or more complete RNA strand.

In some cases, antibodies may be used. Antibodies may be strongly or weakly binding to a particular nucleobase, such as m6A nucleotides. Nucleotides may be ribonucleotides, wherein kinetics and current associated with binding of labeled complementary nucleotides to sample nucleotides, which comprise a sample polynucleotide strand being interrogated by a polymerase complex, wherein sample nucleotides may have different epigenetic modifications which may be better differentiated thereby.

In some cases, modified bases including: 5-methylcytosine, N6-methyladenosine, N3-methyladenosine, N7-methylguanosine, 5-hydroxymethylcytosine, pseudouridine, thiouridine, isoguanosine, isocytosine, dihydrouridine, queuosine, wyosine, inosine, triazole, diaminopurine, ß-D-glucopyranosyloxymethyluracil, 8-oxoguanosine, or 2'-O-methyl adenosine, 2'-O-methyl cytidine, 2'-O-methyl guanosine, or 2'-O-methyl uridine in addition to canonical DNA and RNA nucleotides and other non-naturally occurring nucleotides may be utilized to determine an identity of a base being interrogated, wherein an identity of a base being identified may be any canonical DNA and RNA nucleotide, or may be 5-methylcytosine, N6-methyladenosine, N3-methyladenosine, N7-methylguanosine, 5-hydroxymethylcytosine, pseudouridine, thiouridine, isoguanosine, isocytosine, dihydrouridine, queuosine, wyosine, inosine, triazole, diaminopurine, ß-D-glucopyranosyloxymethyluracil, 8-oxoguanosine, or 2'-O-methyl adenosine, 2'-O-methyl cytidine, 2'-O-methyl guanosine, or 2'-O-methyl uridine.

The Use of Tunneling Labels for Other Applications

In some cases, tunneling label compounds and tunneling electrode pairs as described hereinabove may be utilized for applications other than for DNA sequencing. In some cases, many different nucleic acid strands forming a SAM complementary to many different targets may be bound to different sets of electrode pairs prior to introduction of target nucleic acids, and measurements of tunneling currents may be effectuated as a result of hybridization of target nucleic acids. In some cases, nucleic acid strands forming a SAM may comprise zip or barcodes, enabling detection of many different types of target molecules, with a standard set of many different nucleic acid strand types forming a SAM. In some cases, the many different nucleic acid strand types forming a SAM may be bound to different electrode sets as part of a factory process, and shipped as a complete set of many different nucleic acid strands forming a SAM. In other cases, the many different nucleic acid strand types forming a SAMs may be formed as a part of a method performed by an instrument in the field.

In some cases, nucleic acid strands which may form at least a part of a SAM may comprise a base modification. A base modification may be a thiolation of an alpha phosphate of a nucleobase, such that said a nucleic acid strands may not be extended as a part of an amplification process, but may instead only be able to hybridize to a target or amplicon. In some cases, nucleic acid strands may or may not be extendable. In cases where nucleic acid strands are extendable, a double stranded nucleic acid may be formed during an amplification process.

In some cases, universal primers may be enabled as a result of performing blunt end ligation. Ligation may be performed in an instrument. An instrument may form a system with a chip as described hereinabove. Ligation may be performed within a chip, for example, in separate volumes from volumes which contain electrode pairs used for sequencing. Ligation may be performed either manually or in other equipment separate from equipment which may form a system with a chip as described herein above.

Figure 4:
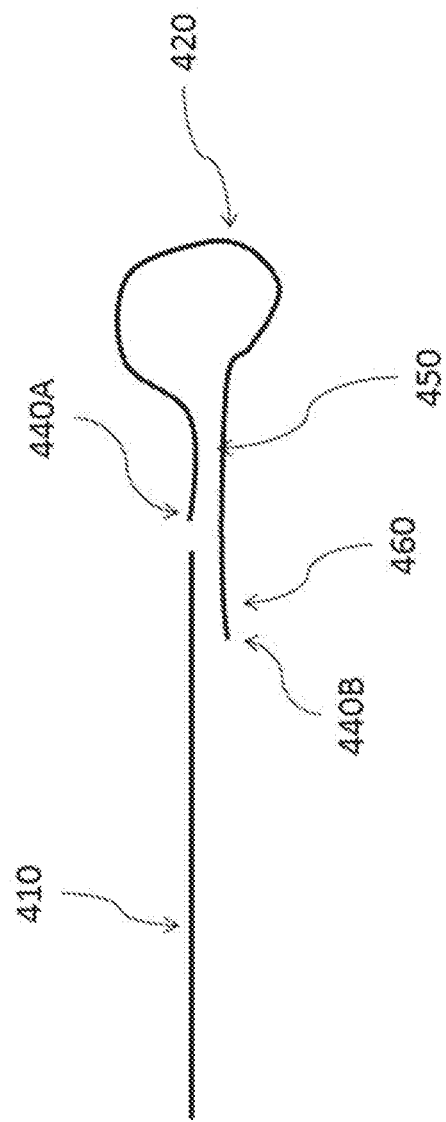
FIG. 4 shows a universal hairpin primer.

In other cases, primers may be ligated using hybridization and then ligation as depicted and described hereinafter with respect to FIG. 4. Hybridization may be specific, utilizing probes complementary to desired regions. In some cases, hybridization may be effectuated using universal bases such as inosine for a section which may overlap an end of a target nucleic acid.

In some cases, a tunneling detection electrode pair may be functionalized with a SAM. A SAM may comprise at least in part a nucleic acid strand. A SAM may utilize a same nucleic acid strand on both electrodes of an electrode pair, thus making the process of fabrication of SAMs easier. In some cases, a tunneling label compound may produce different tunneling currents when a potential is applied in different directions, due to e.g., an asymmetric atomic construction, as is often the case for compounds used molecular devices.

In some cases a tunneling current electrode pair may be used as part of system to detect quantitative PCR or digital PCR. The tunneling current electrode pair may comprise SAMs. SAMs may comprise nucleic acid sequences (e.g., nucleic acid strands). Nucleic acid strands may be at least partially complementary to a tailed probe provided in solution. A tailed probe may be consumed in an amplification reaction, such as a PCR reaction or an isothermal reaction (e.g., strand displacement amplification (SDA) or Loop mediated isothermal amplification (LAMP). SAM(s) on one electrode of an electrode pair may be at least partially complementary to a tail of a probe. Another electrode of an electrode pair may be at least partially complementary to a portion of a probe. A portion of a probe may bind to a target or amplicon strand. A portion of a probe may be effectively consumed as a part of strand extension by a polymerase during strand extension, thereby preventing binding of probes to both electrodes of an electrode pair. A reduction in tunneling current during an amplification reaction may be an indicative measurement of consumption of a probe, and thus an indicative measurement of a presence and or quantity of specific target nucleic acid present prior to said amplification reaction.

In some cases, SAMs may comprise nucleic acid strands which are at least partially complementary to primers. Primers may be complementary to a target nucleic acid or its complement. The nucleic acid strands may be at least partially complementary to tails of primers which tails may not be complementary to a target nucleic acid or its complement. At the beginning of an amplification reaction, primers may bind to one electrode or the other of an electrode pair, but may not bridge an electrode pair, and thus may not provide a tunneling path. As an amplification reaction proceeds, amplicon product may be at least partially complementary to both electrodes of an electrode pair, and may provide a tunneling pathway which may provide increasing current. Such an increase in current may be indicative of a presence of increasing amounts of amplicon from an amplification reaction.

In some cases, different electrode pairs may be used. Different electrode pairs may have different sets of SAMs. SAMs may correspond directly to different nucleic acid targets. In some cases, different electrode pairs may have different sets of SAMs corresponding to tails of primers, which may be used to permit a single type of SAM to be used with many different types of assays, as when utilizing different primers sets with a same set of primer tails.

In some cases, a system may be used as a detector for real time PCR or as an isothermal amplification (e.g., SDA). Self-assembled monolayers (SAMs) may be disposed on a surface of electrodes of an electrode pair. SAMs on electrodes of an electrode pair may comprise the same, or different oligos. Primers matching a SAM disposed on at least one electrode may then be used to detect amplification products, by e.g., detecting the complementary extended amplification product produced as a result of an amplification reaction. In some cases, primers may be used which may be complementary to the oligos of a SAM layer on at least one electrode of an electrode pair.

In some cases, unextended primers may not be long enough to span a width or spacing between electrodes, but an extended primer amplified product may be long enough to span a width or spacing between electrodes. In some cases, an oligo comprising at least a part of a SAM on one electrode may be identical or substantially identical to one primer of a primer pair, while oligos comprising at least a part of an opposing electrode SAM may be at least substantially identical to a second primer of a primer pair, thus allowing direct hybridization to oligos associated with SAMs of both electrodes of an electrode pair. In some cases, primers may comprise tails which may not be complementary to a target nucleic acid polymer. SAMs may utilize a same sequence as a primer tail, wherein primer tails may be identical for both primers, or SAMs may comprise different sequences associated with a two primers of a primer pair. A primer tail may be complementary or identical to a target sequence, or at least a portion thereof.

In some cases, an amplification product strand (or extended strand) may bind to one of the two electrodes. An extended strand may be complementary to only one set of oligos associated with the two electrodes, while a nucleic acid strand complementary to an extended strand may bind to oligos associated with a second electrode of an electrode pair. The two strands may conduct as partially single stranded and partially double stranded DNA across a gap between electrodes of an electrode pair. Two strands may hybridize to both surface bound oligos and to a complementary strand which may be also bound to oligos associated with a second electrode of an electrode pair.

In other cases, an extended primer may bind to different oligos on both electrodes, and may conduct as either fully double stranded or partly single stranded and partly double stranded. In some cases, a label may be slightly longer than the width or spacing of a gap (e.g., a nanogap), so as to insure that a label may be of sufficient length after consideration of any tolerances associated with fabrication of a gap. A gap or nanogap for a particular sensor may be wider or larger than a nominal width or size, and to insure that a label may have an opportunity to bind with a larger region of an opposing electrode after first binding to one side, a label may need to longer than a nominal gap width or spacing. If a label were to be bound to one electrode, and a length of a label were the same as the width of a gap, for the label to bind to the opposing side, a binding site would need to be perfectly aligned opposing the binding site wherein a label may be bound. Thus a label may be made to be larger, such that a label, which may be a relatively stiff label as may occur with a double stranded DNA, may bind with binding moieties which may be in a shape of a cross section of a torus on an opposing electrode, and a difference in diameter of inner and outer rings of a torus cross section may result from at least a combination of flexibility of a label, and angular flexibility of binding moieties.

A label may be designed such that after binding to one electrode a label may be able to bind with an area of an opposing electrode. An area may have an inner diameter greater than or equal to about 1 nm, 2 nm, 3 nm, 4 nm, 5 nm, 6 nm, 7 nm, 8 nm, 9 nm, 10 nm or more. An area may have an outer diameter which may be at least about 1 nm, 2 nm, 3 nm, 4 nm, 5 nm, 6 nm, 7 nm, 8 nm, 9 nm, 10 nm or more greater than an inner diameter. A label which may be able to bind in such a region may be considered to be slightly larger than a gap spacing.

A label may be longer than a width or spacing of a gap. A width of a gap may be considered to be a distance between metallic surfaces. An effective width of a gap may be considered to be a distance between binding moieties, which may be configured to be bound to linkers. Linkers may have a typical angle relative to a metallic surface of an electrode. An angle of linkers relative to a metal surface may be a function of at least a type of binding mechanism, SAM density, linker type, charge of binding moiety and or linker. In cases where a long linker is utilized for a stuck end SAM, or where a binding moiety comprises a stuck end which may be both single stranded and double stranded, and where a double stranded portion of a stuck end, which may be both single stranded and double stranded, may be closer to a linker and thus may be closer to a metallic electrode, a gap spacing or effective gap spacing may be narrower than a width or spacing between metallic surfaces.

In some cases, a single type of oligo sequence may be utilized for both electrodes of an electrode pair, and may hybridize to one sample strand and not to a strand complementary to a sample strand, thus providing partially single stranded, and partially double stranded nucleic acid polymers for tunneling and hopping conductance, which may be bound only at one end.

In some cases, it may be desirable to minimize conductance so as to not saturate detector electronics associated with an electrode pair as a result of high conductances associated with a small number of amplified product, which may not provide a statistically reliable Ct value. It may thus be desirable to minimize a conductance of individual amplified product, by for example, utilizing longer linkers between the surface and a oligos which comprise a part of a SAM and may be used to hybridize the amplified product.

In some cases, electrodes may be configured to capture a single molecule or complex. Electrodes may be configured to capture multiple targets of a same type. Measured current level may be utilized to determine a number of molecules captured.

In cases where a single target nucleic acid polymer may be targeted, multiple enzymes may be bound or associated with a single electrode pair, or with multiple electrode pairs. A sequencing or sequence detection process may not be intended to determine a sequence of a target, but may instead be utilized to detect and quantify a number of copies of a target nucleic acid polymer. This process may be performed after an amplification reaction, as a part of an amplification reaction, or without an amplification reaction.

In some cases, tunneling labels may be used to detect enzymatic activity associated with a ribozyme, wherein tRNA molecules or amino acids may further comprise tunneling labels, and kinetics and or sequence of binding and incorporation of amino acids to a protein may be monitored.

In some cases, multiple electrode pairs may be utilized to target different single nucleotide polymorphisms, using different electrode pairs with different associated complements as described hereinabove. Different conductances may be detected using a same label or different labels with different conductance levels being indicative of a relative number of SNPs in target region.

In some cases, a tunneling or tunneling and hopping detector may be utilized to detect miRNA directly, using different SAMs on different electrodes wherein each different SAM may be complementary to a different about half of an miRNAs or other very short RNA. A competitive hybridization reaction may result from competition between an miRNA or another very short RNA, which may not conduct effectively across a gap associated with an electrode pair, and a competitive oligo which may span a gap, and may be capable of hybridizing to SAMs associated with both electrodes of an electrode pair.

In some cases, detection of a miRNA or other very short RNA may be effectuated by forming a gap associated with an electrode pair with a SAM comprising oligos complementary to a bridge oligo, which may be complementary to oligos of SAMs associated with electrodes of an electrode pair. A bridge oligo may be further complementary with a targeted miRNA or other very short RNA. A bridge oligo may be introduced to and allowed to hybridize with SAMs of respective electrodes of an electrode pair thereby establishing a baseline current prior to introduction of a sample. Introduction of a sample, which may comprise a target miRNA or other very short RNA, may allow miRNA or other very short RNA to hybridize to a bridge oligo. Hybridization may cause an increase in conductance, which may then be quantified to indicate a number or concentration of miRNA or other very small RNA.

In some cases, wherein a target molecule, such as a nucleic acid strand, may be of sufficient length to span a gap associated with an electrode pair, a bridge oligo may not be used. A target molecule may be used to bind to oligos associated with SAMs bound to electrodes of an electrode pair. Oligos associated with SAMs may be complementary to part or all of a target nucleic acid strand, such that when a target nucleic acid strand is introduced and permitted to hybridize with oligos of the SAMs, an increase in conductance may be measured, and a quantity of target nucleic acid strand may be quantified.

In some cases, a target nucleic acid strand may be longer than oligos associated with electrodes of an electrode pair, and may be of sufficient length to allow hybridization of an additional probe oligo between areas complementary to oligos associated with electrodes of an electrode pair, a detection process may comprise detection of a combined target nucleic acid strand, oligos associated with the electrodes of an electrode pair, and a probe oligo.

In some cases, an oligo of a specific length may be placed between two electrodes and a conductance of an oligo may be measured, using a bias voltage between the two electrodes and measuring a current going through an oligo. A current signal may comprise tunneling or tunneling and hopping current. Certain biological or diagnostics information about the oligo may be determined based on measured currents. In some examples, a difference between an oligo with and without methylation may be determined. This method may be particularly useful if methylation of specific sites on an oligo is expected. If more than one possible methylation site may be comprised in the oligo, more than two different current levels may be measured, e.g. a first current level for no methylation, a second current level for one methylation on a first site, a third current level for one methylation on a second site, and a fourth current level for methylation of both first and second sites. This method may work well when a length of an oligo may be larger than a gap width or spacing between two electrodes. For instance, if an oligo is 100 bases or base pairs and a gap size is about 15 nanometers, this method may be very suitably used.

In some cases, a length of an oligo might be larger than the gap size. For instance one might have an oligo of 100 bases or base pairs with a 15 nanometer gap but a portion of an oligo used as a tunneling label might be 60 bases or base pairs long. In such a case one or both ends of an oligo may be hybridized to both electrodes with a portion spanning the gap. Hybridization could be performed, for example, by using complementary SAMs disposed on both electrodes. According to this method, only a conductance of a portion of an oligo or other biological sample may be measured and biological information based on the conductance may be identified. For instance one could identify whether there is one or more methylation site on an oligo as described hereinabove.

In some cases, specificity of detection of a target nucleic strand may be improved by utilizing hybridization of two oligos associated with electrodes of an electrode pair, as compared to hybridization of a single oligo of similar length to oligos associated with electrodes of an electrode pair, or a longer hybridization oligo which may be a length of a combined length of oligos associated with electrodes of an electrode pair. In some cases, specificity may be further enhanced by use of probe oligo to hybridize to a target nucleic acid strand in addition to use of two oligos associated with electrodes of an electrode pair.

In cases where it may be desirable to detect sequences having currents which are too low for accurate quantification due to high AT content, a hairpin may be utilized, which may be complementary to and may bind to a target nucleic acid polymer. A hairpin may comprise a high GC content. A hairpin may be ssDNA, dsDNA, or tetrameric. A presence of target may be determined by an increase in current due to higher proximity brought between high GC portions due to binding of target to hairpin structures. A hairpin may comprise DNA, where a region which is not high GC content may be complementary to a target nucleic acid. A hairpin may be an aptamer, an antibody, or any other binding moiety. A high GC portion may be bound to one or both electrodes of an electrode pair, either directly to conductive electrode(s), or to dielectric which may cover conductive electrode(s). In some cases, a high GC content may be a GC content greater than 50%, greater than 60%, greater than 70% or greater than 80%.

In some cases, at least a portion of a hairpin which binds to a target may be bound directly to electrodes or dielectric associated thereto, or may be a separate moiety bound to an end or between ends of a GC rich DNA region. In other cases, a region which is referred to as a high GC region may not be a nucleic acid strand, but may instead be another molecule with high tunneling or tunneling and hopping conductivity, such as other polymers or other molecules as described herein. Such a molecule may be a chimera of nucleic acids and other polymers, or may be a chimera of antibodies and nucleic acids, or may be a chimera of antibodies and other molecules with high tunneling and or hopping conductivity such as other polymers or other molecules as described herein.

In some cases, particularly where continuous sensing is desired, for example wherein a chip or sensor may be utilized as a water or air monitoring sensor, or wherein a chip or sensor may be utilized in association with a liquid or gas chromatography system, capillary electrophoresis system, or as a detector for any other appropriate separation system, a single sample partition may be used. A single sample partition may be a continuous aqueous or gaseous partition. A single sample partition may use a tunneling and or hopping detector and may monitor continuously output from a separation technique. A separation technique may be performed with resets, for example to allow a wider dynamic range, or to reduce an effect of nonspecific binding, or over an entire run so as to integrate signal, which may be advantageous when an input concentration may be low. A separation technique may increase local concentration for easier and or more accurate detection.

In some cases, a tunneling and or hopping detector may be utilized in association with a gas chromatograph, wherein binding moieties may be bound or associated with electrodes of an electrode pair, and may thence bind specifically or nonspecifically with a target molecule.

In some cases, wherein a liquid chromatography separation may be performed in conjunction with tunneling detection, a streaming potential of unknown magnitude may be generated. Allowing a surface to float relative to underlying electrode potential may allow an appropriate tunneling potential to be applied, which may be effectuated using dielectric covered electrodes and an AC potential applied between electrodes.

In some cases, a label may be bound to an antibody. An antibody may target a protein antigen, an epigenetically modified nucleotide such as a 6-mA RNA base, or other modified RNA or DNA nucleotides.

Sensor Chip: General Usage

In some cases, systems and methods of the present disclosure may utilize a chip. A chip may comprise a reusable chip. A chip may have at least some of target analytes, enzymes, and SAMs removed between different runs. Removal may be effectuated by e.g., raising temperature, decreasing ion concentration, chemical cleaning, plasma cleaning, enzymatic cleaning, electropotential cleaning, any other type of cleaning procedure, or combinations thereof. Such cleaning may include nucleases, proteinases such as proteinase K. Cleaning may comprise changes of potential between electrodes and bulk solution such that thiolated SAMs may be removed, or any other methods. In some cases, a chip may be monitored at various sensor regions to determine how many sensors are active and producing good quality data. In some cases, a chip may be programmed, for example in a local flash memory with a programmed life for a certain number of runs. A programmed chip lifetime may reduce sequencing costs significantly, while maintaining reliability.

In some cases, electrons or holes interacting with a tunneling label may tunnel into a tunneling label or may tunnel through, and may hop through a tunneling label. Electrons or holes may tunnel through part of a tunneling label, and hop through other parts of the tunneling label. Electrons or holes may repeatedly transition between some regions of a tunneling label wherein tunneling may occur, and regions wherein hopping may occur.

In some cases, a high data density may be achieved. A high data density may result from a minimal amount of raw data being produced per base. A high data density may be achieved as a result of an ability to determine which of four or more base type may be present with a single readout of a sensor, as opposed to current sensors which require many readings per base. An asynchronous chemistry method may require frequent measurements because a time when a reaction will occur is unknown. In other cases readings of multiple pixels may be needed in order to determine a color associated with fluorophores associated with different base types. As provided herein, as few as a single reading may be sufficient to determine which nucleobase type has been bound or incorporated, as a magnitude of a signal may indicate both a presence of a base and which type of base. Thus a chip producing high data density with a limited data output capability may produce significantly more output bases per unit time than previously existing systems, which may require reading of multiple pixels for each color, and may require four colors corresponding to the four standard bases. A higher data density may facilitate reduced computational hardware and or time to analyze a data set.

In some cases, a system as described herein may measure or interrogate each base more than once depending of the application and if deemed helpful for overall accuracy in a particular measurement. In some cases, a system may use a single sample to perform one or more tasks, including sequencing DNA, sequencing RNA, determining epigenetics of DNA with or without chemical modification, determining epigenetics of RNA with or without chemical modification, determining copy numbers of DNA which include determination of aneuploidy, determining expression level of different transcripts, determining the presence and quantity of different proteins, and determining the presence and quantity of other biological molecules of interest. In performing such tests for a single sample, a system may utilize a combination of RNA dependent polymerases and DNA dependent polymerases. Different types of polymerases may be utilized in different chips. Different types of polymerases may be utilized in different volumes of a single chip. Different types of polymerases may be utilized in different volumes of two or more chips or may be utilized together in a single volume of one or more chips.

In some cases, a system may comprise a chip with electrode structures, and may not comprise an amplifier or row and or column select associated with different sensors, Circuits needed for measurement may not be a part of a chip, but may be a part of an additional chip or circuit. In other cases, local amplifiers, and optionally row and or column select circuits may comprise a part of a chip, while integration, double correlation, analog to digital conversion and digital input output ports may not be a part of the chip, but may be a part of an additional chip or circuit.

Sensor Electrodes

A system of the present disclosure may be a highly scalable system. For example, millions or billions of sensors may be disposed on a single chip similar in size to current DNA sequencing electronic sensors, including two electrodes separated by a gap, with a very small pitch on a single device. In some cases, a chip may have a very high density of sensors. For example, a single chip may have a sensor density greater than or equal to about 5,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, 20,000,000, 30,000,000, 40,000,000, 50,000,000, 60,000,000, 70,000,000, 80,000,000, 90,000,000, 100,000,000, 200,000,000, 300,000,000, 400,000,000, 500,000,000, 600,000,000, 700,000,000, 800,000,000, 900,000,000, 1,000,000,000, 2,000,000,000, 3,000,000,000, 4,000,000,000, 5,000,000,000 or more sensors/inch$^2$. In some cases, older modes for circuit processing may be utilized, such that various custom chip designs can be fabricated without the cost of a state of the art high density mode such as 14 nm or the soon to be effectuated 10 nm modes. In some cases, a density of sensors may not be restricted by optical or diffusional crosstalk.

In some cases, a massively parallel design of a chip using lithographic processes may be used to place a large number of sensors on a substrate. Each sensor may have two electrodes separated by a gap. Individual sensors may be separated by a pitch size. A pitch size may be the same or different in X and Y axes. Each sensor may have an individual or multiplexed electronic path to place a bias voltage between electrodes on an electrode pair and or read out a tunneling current. As such, each electrode may be individually addressable and readable, or may be read out in groups, for example in rows, wherein an analog to digital converter may present for each column. In some cases, multiple analog to digital converters may be present associated with each column, for example at the opposing ends of a column, or may be interspersed within a column. Electrodes on each sensor may be made from gold, platinum, copper, palladium, silver, or other coinage or noble metals, or graphene. The use of coinage or noble metals may facilitate thiol bonding to electrodes.

In some cases, a gap size between electrodes comprised in sensors may be designed so that electrodes may be parallel or within 1, 2, 3, 4, 5, 6, 7, 8, 9, or 10 degrees of parallel. The electrodes may also be designed to have a spacing such that SAMs may be placed on electrodes, and an enzyme may fit between SAM layers bound to electrodes in a gap therebetween.

Figure 3A:
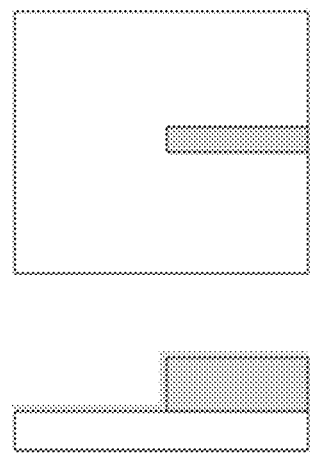
FIGS. 3A-3D show the steps in fabricating nanogap sensor.
Figure 3B:
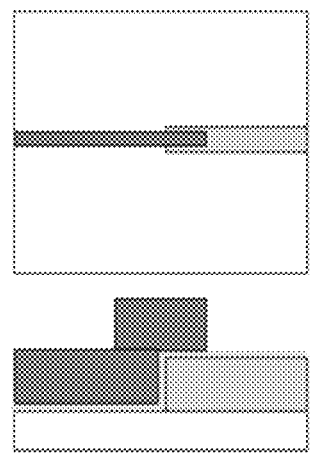
Figure 3D:
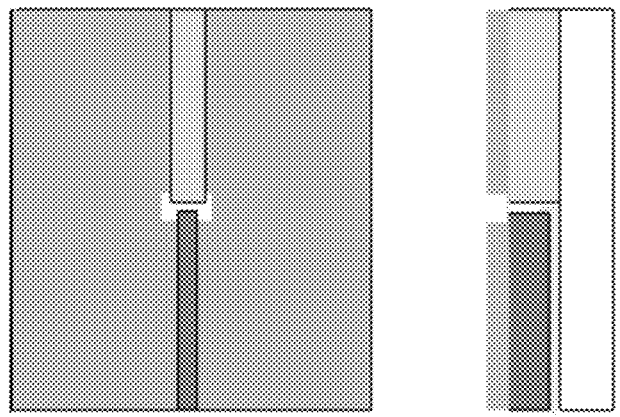
Figure 3C:
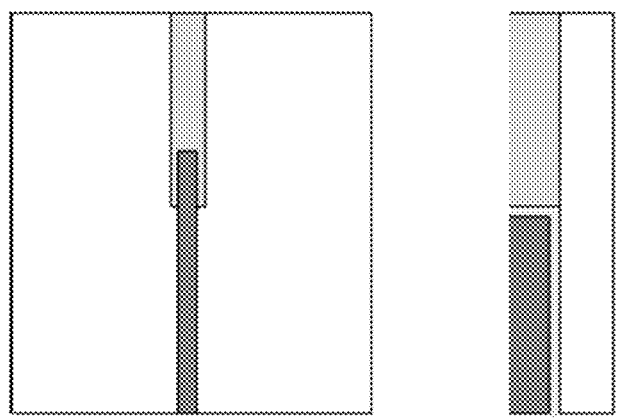
Figure 3E:
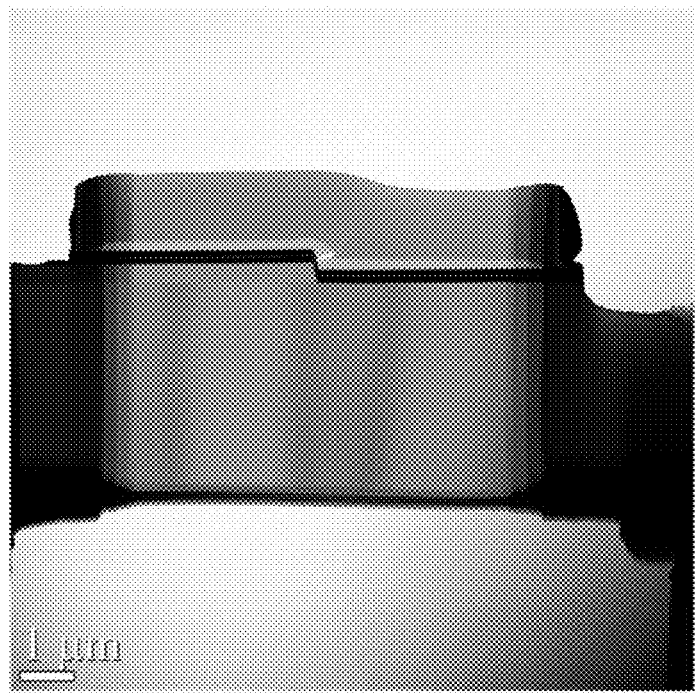
FIGS. 3E-3I show SEM and TEM images of sensors formed using the process shown in FIGS. 3A-3D.
Figure 3F:
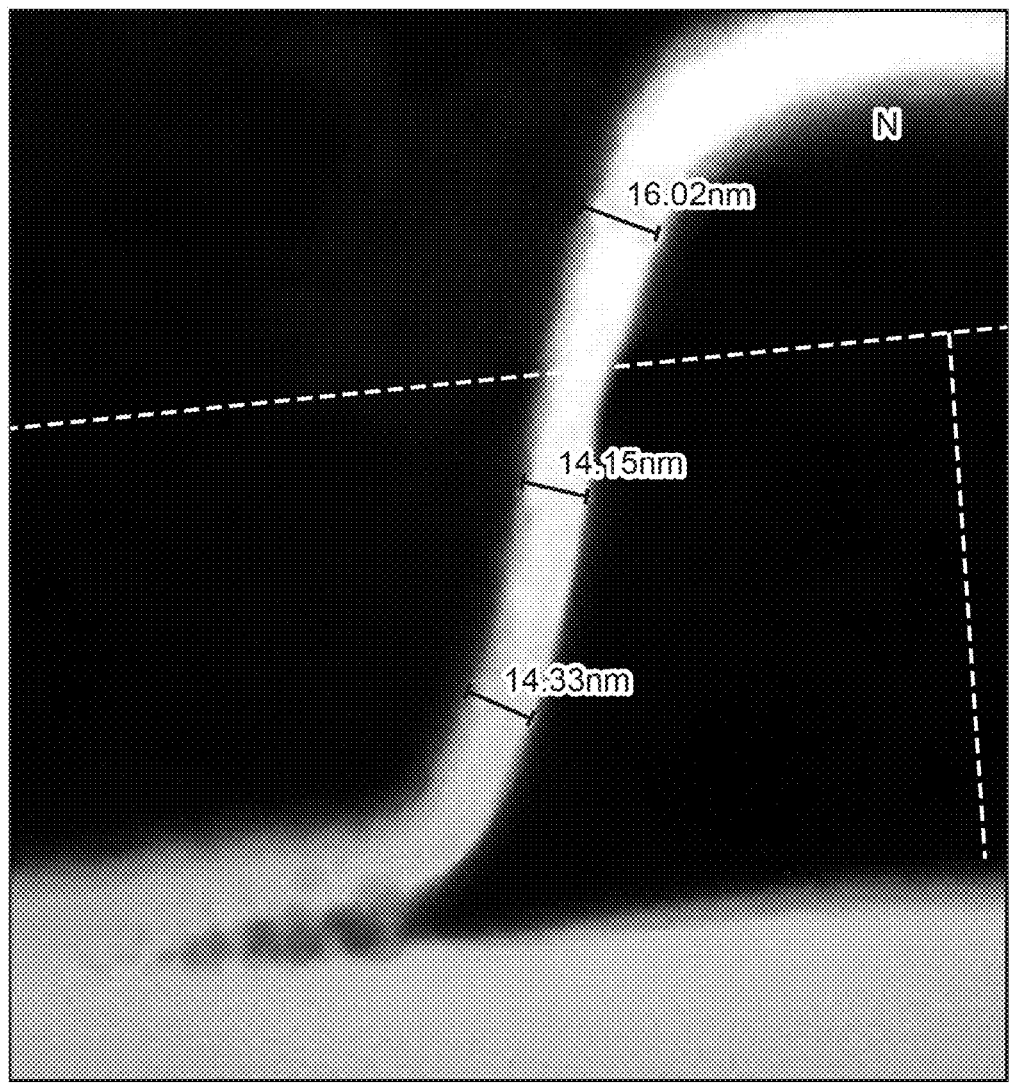
Figure 3G:
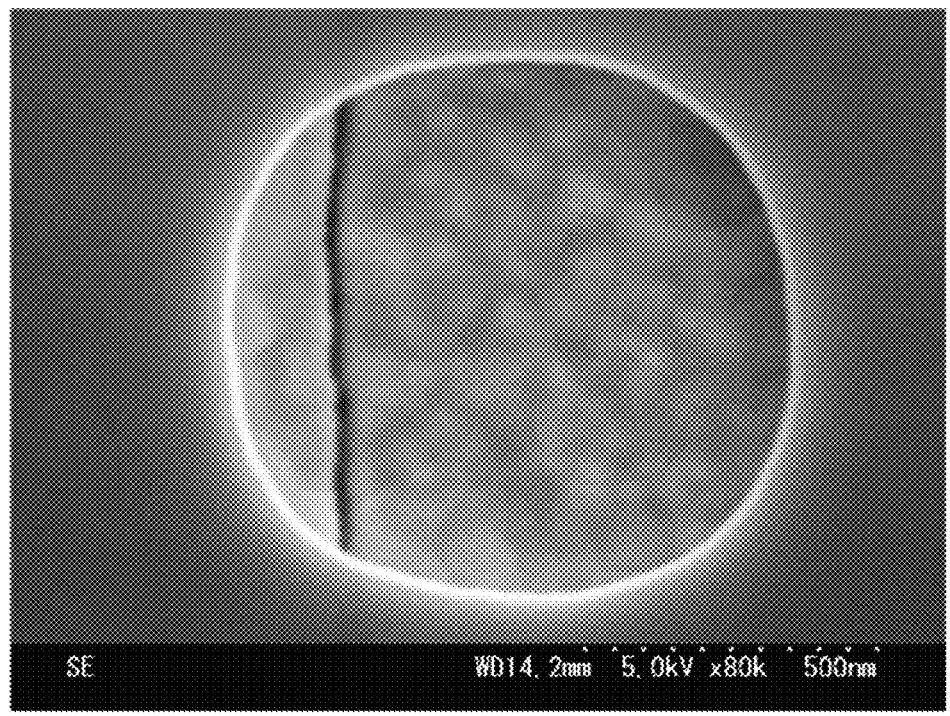
Figure 3H:
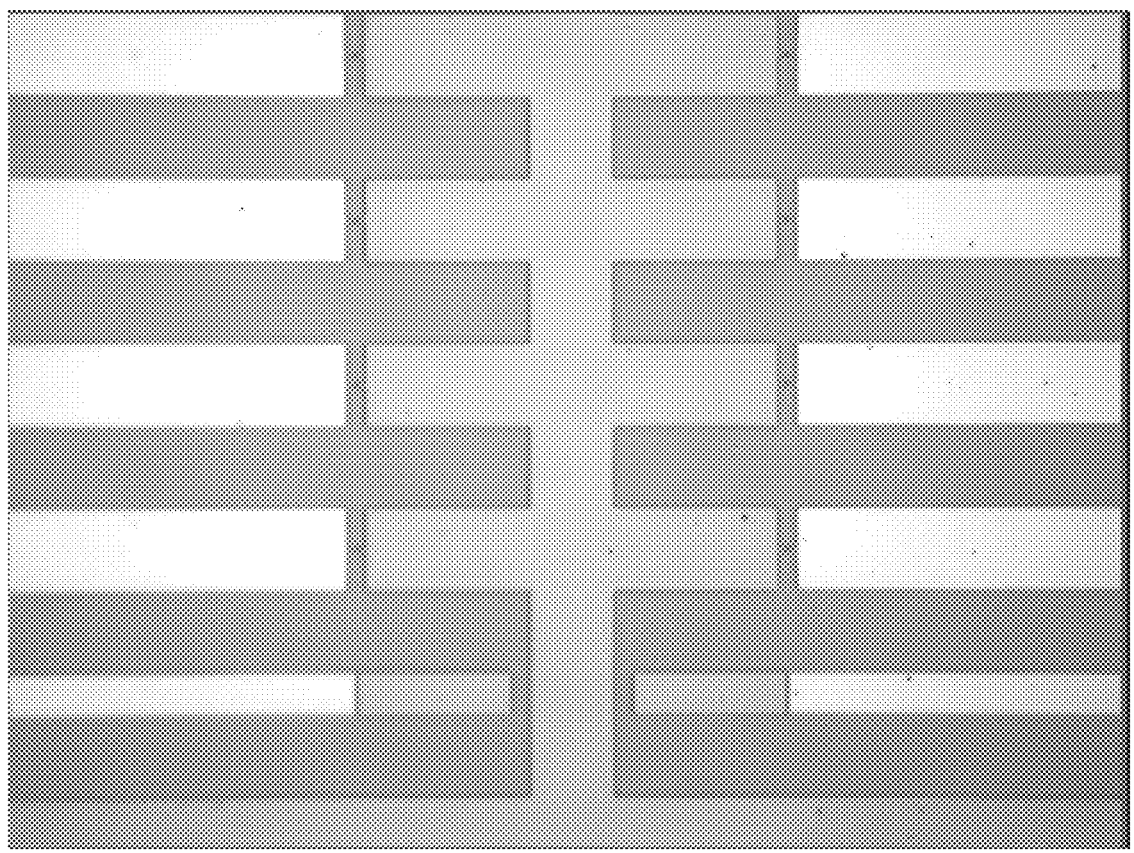
Figure 3I:
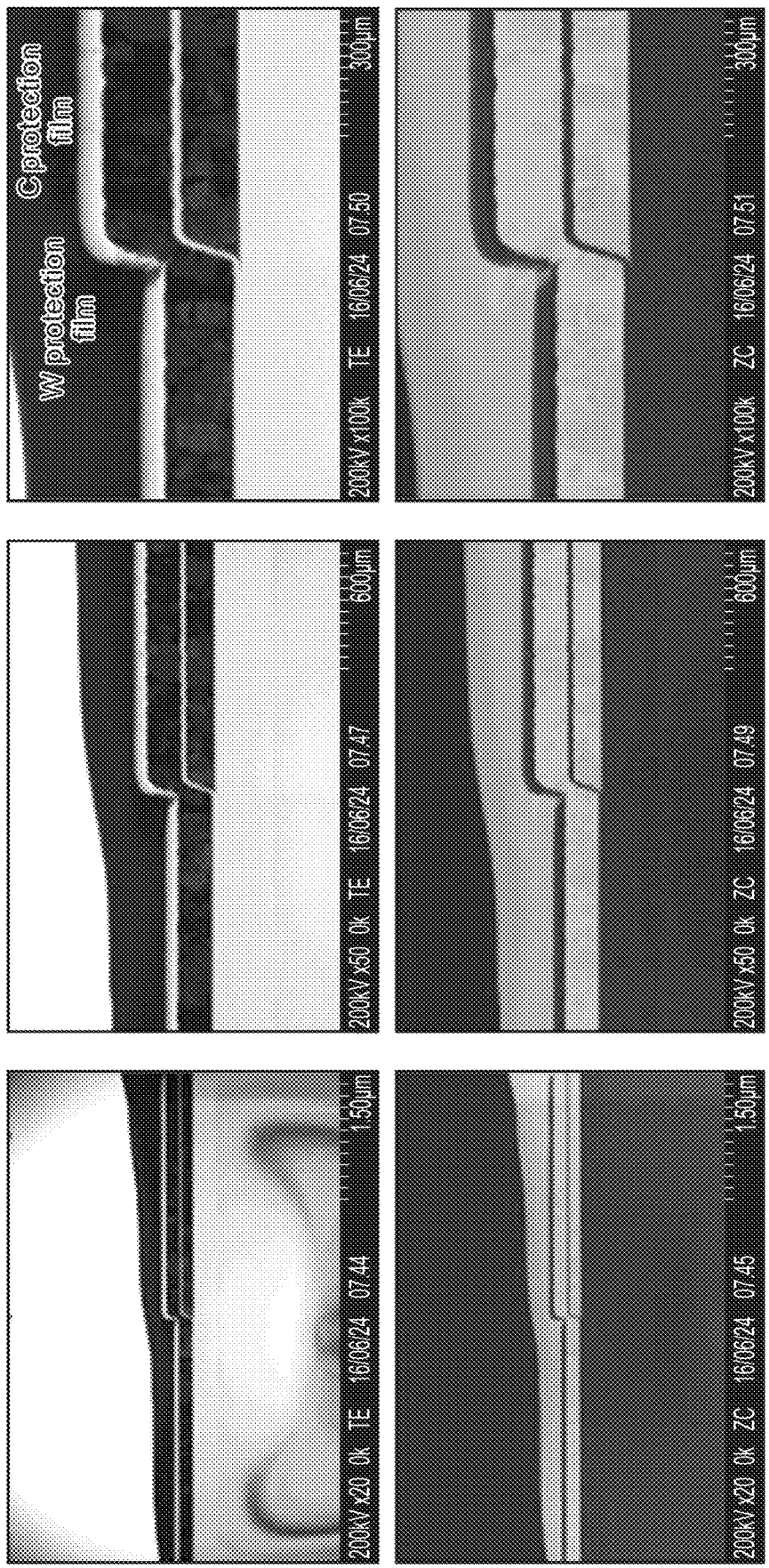
Figure 3K:
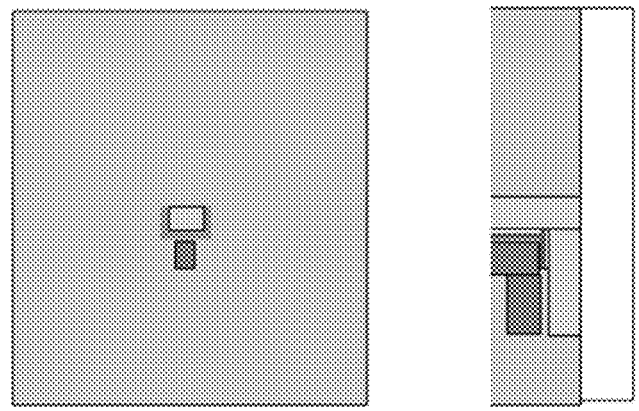
FIGS. 3J and 3K show another method for forming a nanogap sensor.
Figure 3J:
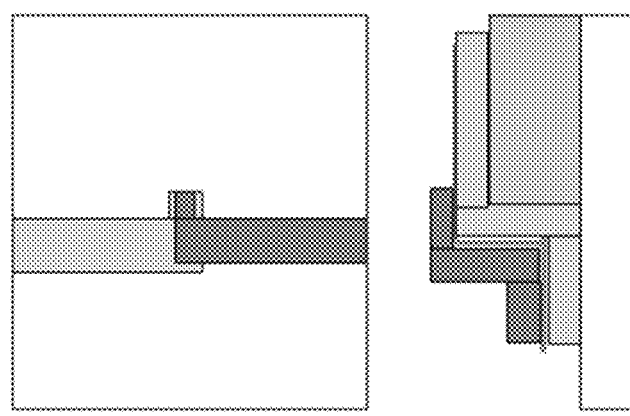
Figure 3L:
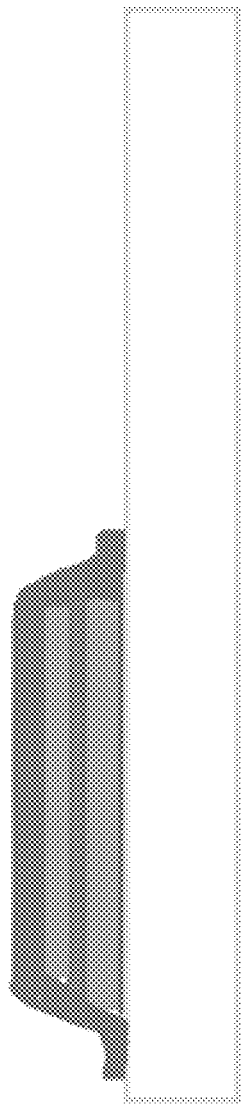
Figure 3N:
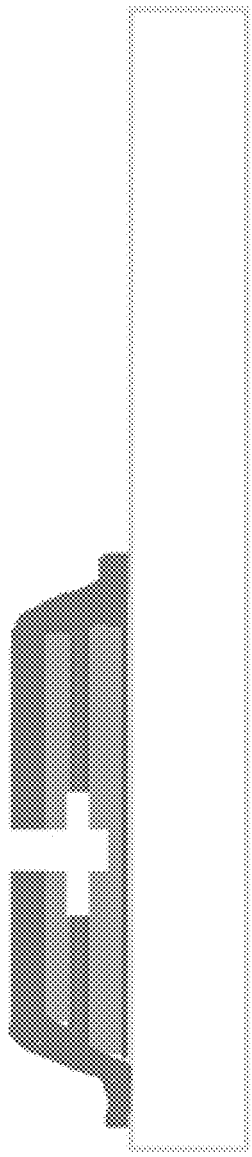
Figure 3O:
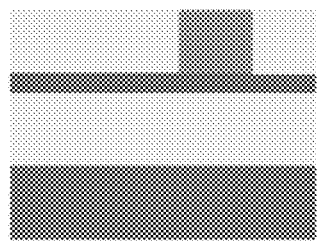
FIGS. 3O-3V show another method for forming a nanogap sensor.
Figure 3P:
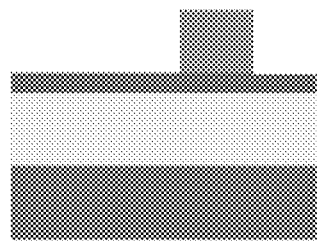
Figure 3R:
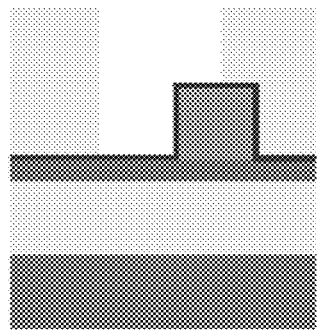
Figure 3Q:
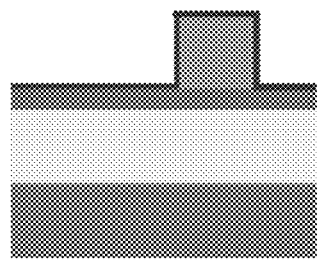
Figure 3S:
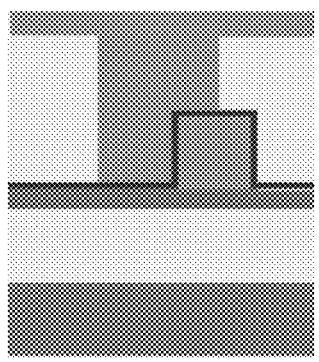
Figure 3T:
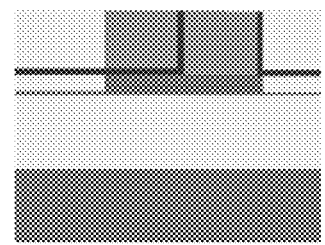
Figure 3V:
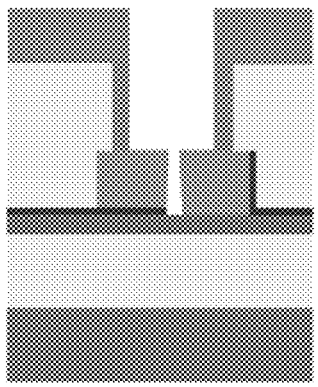
Figure 3U:
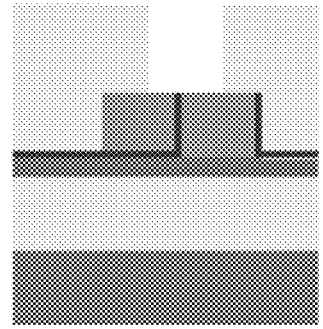
Figure 3W:
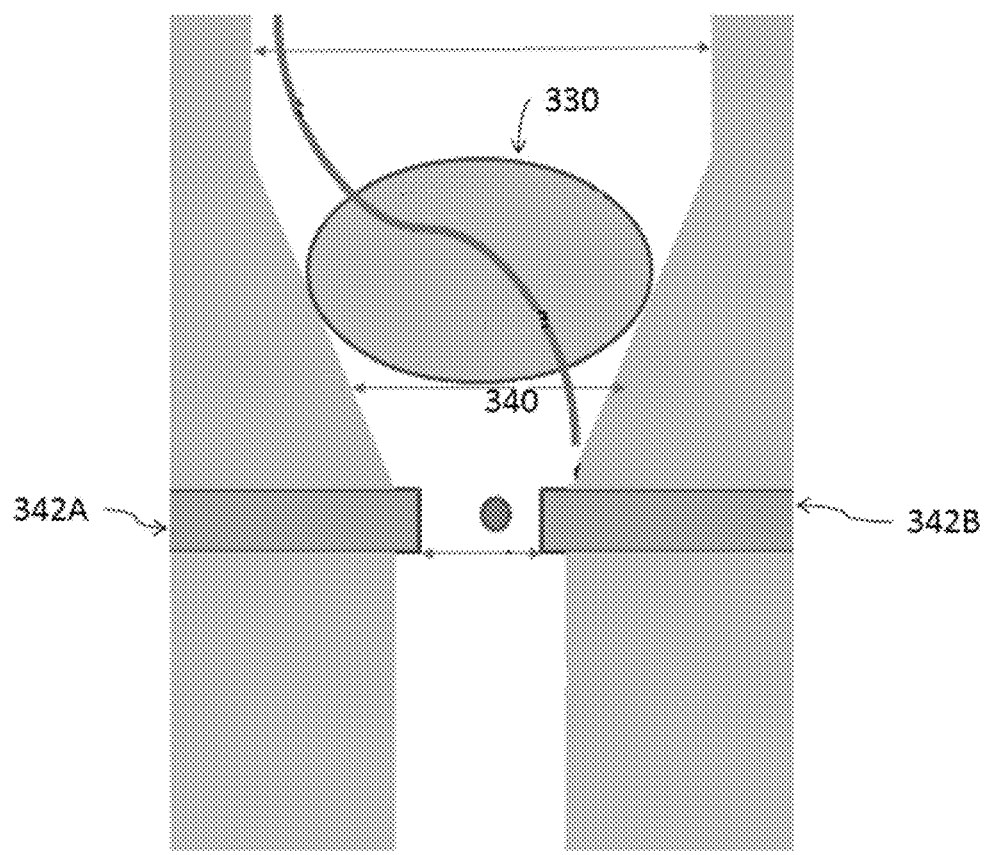
FIG. 3W depicts a nanogaps sensor with a narrower nanogap.

In some cases, as shown in FIG. 3W, electrodes, or a structure associated with electrodes may be angled with respect to each other, and may be formed using a KOH etch to create inverted truncated pyramids. Electrode pairs 342A and 342B associated thereto may be formed with an angle with respect to each other, or may be fabricated with facing sides parallel or essentially so as described hereinabove. A structure may have an entrance which may have a width sufficient to allow entrance for a polymerase or other enzyme 330, while having angled surfaces 340 which may be too narrow for a polymerase to fit therebetween, and may further have electrodes which may have a spacing which may be significantly narrower than a polymerase or other enzyme 330, such that a label shorter than a diameter of a polymerase or other enzyme may be utilized.

In some cases, a gap size between electrodes may be narrower or smaller than about 10 nm, allowing measurement of conductance using a nucleic acid label with about 30 base pairs. In some cases, a gap may be larger or wider than about 2-3 nm to avoid creation of TLF false positives and to ease manufacturing.

In some cases, a set of fluidic channels may be utilized to distribute reagent sets, enzymes and or polymerases to electrode pairs disposed on or adjacent to a substrate. In some cases, a fluidic channel may be a width corresponding to a physical readout configuration for a chip, such as a number of rows per multiplexed amplifier. A fluidic channel may be of a height sufficient to readily supply reagents and enzymes, which may be a height of 100 nm to 200 nm, 200 nm to 500 nm, 500 nm to 1 μm, 1 μm to 5 μm, 5 μm to 10 μm, 10 μm to 50 μm, 50 μm to 250 μm, or greater than 250 μm. A width of a fluidic channel may be made to be fairly narrow, as it may be of a width which may correspond to hundreds or thousands of sensors, and thus a tolerance with a height may be significantly tighter than would be the case if a fluidic channel were to cover an entire chip. In other cases, a gap (e.g. a nanogap) associated with a sensor may be wider than a width of an enzyme or polymerase. A width of an enzyme or polymerase may be considered to be a minimum dimension of an enzyme or polymerase wherein an enzyme or polymerase may be complexed with a partly single stranded and partly double stranded nucleic acid, and the thumb of an enzyme or polymerase may be open with respect to the palm of an enzyme or polymerase. An axis of a nucleic strand along the length of a nucleic acid portion bound within or to an enzyme or polymerase and complexed within an enzyme or polymerase may be parallel with metallic surfaces which comprise a gap or nanogap. In some cases, at least one electrode of an electrode pair may be covered, partially covered, or not covered with dielectric, and a second member of a pair may be covered, partially covered, or not covered with a dielectric.

In some cases, a sensor may comprise an electrode pair. An electrode pair may be configured to detect tunneling or tunneling and hopping labels, or may be used to detect target moieties directly. In further cases, rather than utilizing a gap as described hereinafter, an electrode pair may be formed without creating a gap or nanogap, but may otherwise be formed in a similar way, excepting that an RIE step to form the gap may not be performed. In such cases, the active areas of the electrodes may be substantially coplanar. In such cases wherein a polymerase, enzyme, or other moiety utilized in a measurement may be bound to a dielectric which may form a spacing between a sense and a bias electrode, a linker associated with a label and or length of a label may need to be formed in such a manner as to be longer than would be needed if a polymerase, enzyme or other moiety were bound at the midpoint between a sense and a bias electrode in order to take into account tolerances in positional binding and movement of the polymerase, enzyme or other moiety utilized in a measurement. Additional tolerances which may be considered may include for example, diffusion with respect to the binding point of a polymerase, enzyme or other moiety utilized in a measurement due to diffusional movement permissible due to a length of a linker by which a polymerase, enzyme or other moiety utilized in a measurement may allow, or rotation of a polymerase, enzyme or other moiety utilized in a measurement.

In some cases, instead of a pair of electrodes, triples, quads, or arrays (e.g., linear arrays) of electrodes may be used. Electrodes may be configured in an arrangement such that electrodes may be substantially coplanar with a same or with different distances between different electrodes.

In some cases, electrodes may be covered or partially covered with a dielectric, such that a DC current may be minimal, and may not be measurable in some cases, but an AC field may be applied and a tunneling current may be determined in addition to any capacitive currents. This may allow utilization of tunneling and or hopping current detection in conjunction with separation by another methods, such as electrophoretic separation, where fields associated with electrophoretic separation may otherwise influence tunneling currents and or binding to tunneling electrodes as potentials associated with an electrophoretic field may not be well determined or controlled, or may be variable.

In some cases, detection and quantitation may be achieved either using kinetic detection as described hereinabove, which may be kinetic detection of multiple molecules, or detecting a number of copies which may be fixedly bound. In some cases, a dynamic range may be increased by increasing a number and or size of electrode pairs.

In some cases, a structure may be fabricated using a variety of standard semiconductor processing methodologies, which may include, for example and as shown in FIGS. 3A to 3D:

1) starting with a planarized substrate;
2) applying a silicon oxide layer, which may be applied using a chemical vapor deposition method;
3) applying a photoresist, which may be a UV sensitive mask or an ebeam mask;
4) exposing the photoresist, wherein the exposing may use a standard photomask, or may use a direct write method such as an ebeam;
5) developing the photoresist;
6) applying a metal layer, which may be applied utilizing a sputtering method, as shown in the top view of FIG. 3A;
7) removing the undesired portions of the metal layer, which may be removed using a lift off method;
8) applying a dielectric layer, which may be a silicon nitride layer, and may be applied with a thickness which may be a desired electrode gap spacing as shown in the bottom view of FIG. 3A;
9) applying a photoresist, which may be a UV sensitive mask or an ebeam mask;
10) exposing the photoresist, wherein the exposing may use a standard photomask, or may use a direct write method such as an ebeam;
11) developing the photoresist;
12) applying a metal layer, which may be applied utilizing a sputtering method;
13) removing the undesired portions of the metal layer, which may be removed using a lift off method as shown in FIG. 3B;
14) planarizing the surface, which may expose the desired portions of the electrode structure, and may be effectuated using a CMP (Chemical Mechanical Polishing) method as shown in FIG. 3C;
15) applying a dielectric, which may be a silicon nitride or silicon oxide layer, which may be applied using a chemical vapor deposition method;
16) applying a photoresist, which may be a UV sensitive resist or an ebeam resist;
17) exposing the photoresist, wherein the exposing may use a standard photomask, or may use a direct write method such as an ebeam;
18) developing the photoresist;
19) performing a dry etch, which may be a reactive ion etch, which may form a nanogap between the electrodes, and may form a well like structure above the electrodes; and 20) removing the photoresist, which may comprise an SPM (sulfuric acid and hydrogen peroxide) step, and may comprise an ashing step as shown in FIG. 3D.

Such a structure is shown in FIG. 3E, which shows a cross section of a single sensor, in FIG. 3F which shows a closeup view of a nanogap and two opposing electrodes, in FIG. 3G which shows a top well structure in the top oxide layer and two electrodes with a nanogap between with crystal grains being apparent in the electrodes, FIG. 3H which shows a number of sensors and metal interconnects, and in FIG. 3I which shows cross section of such a structure at different zoom levels.

In other cases, which may be utilized in order to improve orientation of crystal grains, and which may result in having opposing 111 crystal planes as opposing surfaces of electrodes in electrode gaps, wherein an initial layer may be a dielectric layer, upon which the first electrode forming metal layer may be formed, and thence the gap spacing dielectric, and then the second electrode forming metal layer, resulting the cross sectional view shown in FIG. 3J, wherein both electrodes are formed in the same depositional direction from the a face opposing the active surface of the first electrode, to the active surface of the first electrode, to the intermediate gap spacing dielectric, and then the active surface of the second electrode and finally the inactive second surface of the second electrode opposite the active surface area of the second electrode. A dielectric is then deposited, and the structure is planarized, resulting in the structure shown in cross section in FIG. 3K.

In some cases, in order to better center an enzyme, polymerase or other moiety which may be utilized as a part of a measurement or a moiety which may be a size of a moiety used as a part of a measurement, and wherein it may be desirable to prevent steric hindrance in the function of an enzyme, polymerase or other moiety, it may be desirable to create one or more layers over active surfaces of electrodes, which may be longer (thicker) than a SAM which may be utilized as a part of a later measurement. The length (or thickness) of a layer, which may be a metal layer which may be formed by electroplating, or a dielectric layer, or a SAM layer, may be formed prior to binding or attachment of an enzyme, polymerase, or other moiety used as a part of a measurement process; an enzyme, polymerase or other moiety may thence be bound or attached, for example to a dielectric layer which may form a gap spacing between electrodes, and an enzyme, polymerase or other moiety may thus be spaced away from electrodes; the layer used to space an enzyme, polymerase or other moiety from electrodes may then be removed, and if needed or desired, a SAM may thence be bound to electrodes.

In other cases, a structure may be formed in which may utilize a vertical electrode structure, rather than a horizontal electrode structure as described heretofore. For such a structure and as shown in FIG. 3L, first an oxide layer may be deposited, then a first electrode metal layer, then a gap spacing dielectric layer, then a second electrode metal layer, and then a covering dielectric layer.

Then as shown in FIG. 3M, an etch pattern is formed which may cut vertically through the top dielectric, the second electrode metal layer, the gap spacing dielectric layer, and may cut through a portion or all of the second electrode metal layer, which etch may be performed using an ion milling process or any other appropriate anisotropic etch process. Then as depicted in FIG. 3N a wet etch may be performed which may preferentially etch a gap spacing dielectric, thereby forming electrode structures with opposing 111 crystal planes.

In other cases, a damascene or dual damascene process may be utilized; starting with a planarized substrate; applying an oxide layer, which may be applied using a chemical vapor deposition method; forming a patterned oxide layer with an opening for a desired metal volume may be formed and a metalization layer formed over the oxide layer. A CMP process may be utilized to remove excess metal leaving a structure as shown in FIG. 3O. The patterned oxide layer may then be removed, leaving the structure shown in FIG. 3P. A spacer layer, which may be a silicon nitride layer, may then be applied over the structure as shown in FIG. 3Q. A new patterned oxide layer may then be formed, wherein an opening is formed next to and over the first metal volume as shown in FIG. 3R. An additional metal layer may then be formed, including in the opening left in the second patterned dielectric layer as shown in FIG. 3S. The structure may then be planarized as shown in FIG. 3T. A third patterned oxide layer may then be formed using chemical vapor deposition followed by applying a resist layer and patterning the resist layer, and thence using a dry etch leaving a structure as shown in FIG. 3U. A photo resist may again be applied, a wet or dry etch may be utilized to form a structure as shown in FIG. 3V.

Sensor Electronics

Since an array of sensors may be made as an integrated semiconductor device in the present disclosure, it presents great advantages in terms of accuracy, integration and scaling. In some cases a high data bandwidth may not be required, particularly for a system utilizing a synchronous chemistry method. A system chip may be massively parallel and only sensors that register an incorporated nucleotide may be read out. A chip may initially be mapped to determine which sensors are providing useful data, and a map, which may exist in a flash memory on a chip, or may exist elsewhere as a part of other portions of a system. This makes a system throughput, including data throughput effectively much higher, and may aid in making calibration and accuracy very reliable. In some cases, a single measurement may be used. In some cases, an incorporated or bound labeled nucleotide may be measured multiple times until a desired accuracy is achieved.

In some cases, a sensor may be utilized to measure binding and or incorporation kinetics, so that epigenetic information may be determined as a part of a sequencing process, which may require reading a sensor multiple times, and potentially at a higher frequency than might otherwise be required. In such cases, only a portion of a chip may be utilized at a time, or a smaller chip may be utilized in accordance with a maximum data output capability.

In some cases, a sensor may be associated with a local amplifier, such as a 4T circuit, similar to that used in a CMOS imaging sensor. In some cases, a capacitor may be used to integrate a current produced by a tunneling electrode pair. A capacitor may serve to average variations due to binding and release of a label from an electrode pair. A capacitor may serve to average variations in binding locations which may cause variations in a magnitude of current produced by an electrode pair, as well as averaging a background, which may result from direct tunneling between electrodes, and or between SAM constituents, and or as a result of other moieties which may be transiently bound such as a target DNA, unbound nucleotides or other molecules which may be intended parts of a system, or other contaminants. Such an averaging capacitor may be useful to improve signal to noise, and or to allow a longer time between measurements than would otherwise be possible without a capacitor, while retaining charge from tunneling current.

In cases where a current combined with an integration time may be larger than may be desirable for a size and voltage associated with a charge integrating capacitor, a negative gain may be utilized as a part of an amplifier associated with each sensor or with a capacitor. Negative gain may be useful if e.g., significant variation in binding time, position may be a part of a measurement, or a long time is desired for other reasons between measurements. As shot noise may not be anticipated to play a significant role in a measurement, an increase in shot noise, which may result from a negative gain, may cause an insignificant decrease in signal to noise for a sensor. Such a design is schematically shown in FIG. 3X, wherein a potential is shown as being applied to a bias electrode, with the output of a sense electrode being fed to a row select transistor which would shunt all current from the input sense electrode to ground if a sensor is in disabled state, while becoming an open in an enabled state allowing current to flow to a current mirror configured for negative gain. The output from the current mirror is shown as being connected to an integrating capacitor with an associated reset transistor which may reset the capacitor by fully discharging the capacitor when the RD node is configured to be at a ground potential.

In some cases, a gap size may be greater than or equal to about 5, 6, 7, 8, 9, 10, 15, 20, 30 or more nm or more. Such a gap size may provide additional advantages such as ease of manufacturing and greater tolerance to a size of the gap. In such cases, a tunneling label or tunneling and hopping label may be configured to be larger than the gap size so that an angle of a bound tunneling label with respect to the surface of the first electrode opposing the second electrode, may be 5-10 degrees, 11-20 degrees, 21-30 degrees, 31-40 degrees, 41-50 degrees or more than 51 degrees. For instance, a 9 nm-gap may be used with a label of double-stranded DNA of about 30 base pairs or greater. A 12 nm-gap may be used with a label of double-stranded DNA of about 40 base pairs. A 20 nm-gap may be used with a label of double-stranded DNA of about 60 base pairs. A gap size may be configured to fit commercially available or readily constructible DNA oligos of specific lengths.

In some cases, a bias voltage may be turned off for most of a run while sequencing a polynucleotide. This may help minimizing molecules sticking or adsorbing to electrodes due to electrostatics which in turn could cause artifacts. In some cases, a bulk solution potential may be modified during a part of a run to minimize molecules sticking or adsorbing to electrodes. In some cases, a background signal (which may be due to an ion current) may be minimized due to a small exposed electrode metal surface area. In some cases the exposed metal surface area of each sensor may be less than 1,000,000 $nm^2$, less than 400,000 $nm^2$, less than 100,000 $nm^2$, less than 40,000 $nm^2$ or less than 10,000 $nm^2$. This may improve a signal to noise associated with measurement of tunneling current. A background signal may be determined form sensors which may not have bound enzymes, and may thus not have signals. In some cases, an electronic tag may be chosen in a way to optimize a tunneling current. A size of the molecule may be chosen to be slightly longer than a gap between two tunneling electrodes, which may include a tolerance associated with fabrication of the gap, or may be chosen to be slightly longer a binding position associated with SAM(s) bound to the tunneling electrodes, which may take into account variation in binding location of the SAM(s) on electrodes and or variation in a size of a gap between electrodes.

In some cases, current levels may be selected for a set of labels such that a ratio of currents may be of a fixed level in log space between different labels, such as having a highest conductance label which with an applied bias of 0.1V may produce 1 nA of current at 100 percent duty cycle, and may produce an average current of 250 pA at a 25 percent duty cycle corresponding to a 50 percent duty cycle for nucleotide binding events and a 50 percent duty cycle for hybridization events during nucleotide binding events; thus utilizing a factor of four between different labels a next most conductive label may produce an average current of about 64 pA, the next most conductive label an average current of about 16 pA, and the least conductive of a set of four (four is used here in a non-limiting exemplary manner) may have a current of about 4 pA. In some cases, a bias voltage may be used between two tunneling electrodes of a pair of tunneling electrodes wherein one electrode of a pair may have a positive voltage and the other electrode of a pair of electrodes may have a negative voltage with respect to each other.

In some cases, binding and or tunneling associated with tunneling labels compounds may be temperature sensitive. Thus in some cases a chip with electrode pair sensors may utilize temperature control. Temperature control may utilize a fixed temperature throughout a nucleobase measurement and or incorporation cycle, or may utilize different temperatures for different portions of a cycle.

In some cases, compounds having natural backbones may be utilized as part of a nucleotide associated with a SAM and or tunneling label compound. In some cases, other types of backbones, and or sugars or sugar substitutes may be utilized, such as peptide nucleic acids, locked nucleic acids, hydrolysis resistant bases such as morpholino bases, dideoxide bases, L-DNA, glycol nucleic acids, threose nucleic acids, or any other type of nucleic acid.

In some cases, differences in tunneling currents may result from different types of tunneling label compounds associated with different nucleobases. In some cases, a tunneling current may be influenced by a length or a stiffness of a linker between a nucleobase bound by a polymerase and bound through a linker to a tunneling label compound which may at least in part comprise nucleobases.

In some cases, binding to SAMs may be the same for a set of tunneling label compounds. In other cases, binding to a SAM may vary as a result of differences in charge associated with tunneling label compound. In some cases, binding to a SAM may vary due to nucleobase sequence or nucleobase type such that binding kinetics and average tunneling currents may be affected, whilst average tunneling currents may not be affected.

In some cases, target nucleic acids may be complexed with polymerases prior to introduction into a volume with electrode pairs. A polymerase may be bound in a vicinity or fluidic environment of the electrode pairs. Polymerases may be bound in the vicinity of electrode pairs prior to introduction of target nucleic acids, and target nucleic acids may then be introduced to a polymerase to form a complex. In some cases, after a set of sequencing cycles is complete, buffer conditions may be modified such that nucleic acids may be released from polymerases, washed from a fluidic environment, and a new set of nucleic acids may be directed into a fluidic environment and complexed with polymerases. Nucleic acids may be concentrated using a DC field, magnetic field, dielectrophoresis or both.

In some cases, a single volume may be utilized as a part of a single chip, so that any input fluids may interact with any of electrode pairs on a chip. In other cases, several volumes which may be fluidically separate may be provided, so that different fluids, which may comprise different samples, may be introduced to or through any fluidically separate volumes. Valving may be provided integrally as a part of a chip design, or multiple input and output ports may be provided. In some cases, different parts of a chemistry may be performed in different volumes, so that a single chip may take data for a greater percentage of time. For example if four fluidic steps are required, each taking a minute, and a time needed to read out a volume is a minute, then five fluidic volumes may be provided, so that one volume may take data, and four other volumes may each be performing different fluidic deliveries. After a minute has transpired, each volume may then begin a different task. Thus data may be produced continuously.

In some cases, a same chemistry may be performed in all volumes of a chip. In other cases, different chemistries may be performed in different volumes. For example, one volume may perform a low coverage epigenetic method, while another volume may perform a method that provides long reads, and thus structure, while another volume may perform a method that maximizes throughput as measured in nucleobases read per bytes transmitted out of chip. Different volumes may be of a same size, or may be of different sizes. A single sample or single set of samples may be utilized in one or more volumes, or different samples or different sets of samples may be utilized in different volumes. As a part of attachment of primers, which may be universal primers, bar codes or zip codes may be used for a single sample, or may be used for a sample set.

In some cases, one or more reference electrodes may be supplied as a part of a chip so that a bulk fluid potential may be controlled with respect to a potential of electrodes of electrode pairs. Reference electrodes may be true reference electrodes, quasi reference electrodes, counter electrodes, auxiliary electrodes, or any combination thereof. In some cases, one or more electrodes may be placed outside a chip, for example through a fluidic line which interacts with a fluidic volume with electrode pairs.

In some cases, a reference and or counter electrode, or pseudo reference electrode may be utilized in a manner such that it effectively acts as a gate electrode, wherein, for example a tunneling label which may have different conductances depending upon an oxidation state, and a reference and or counter electrode, or pseudo electrode may be utilized to oxidize or reduce a label, particularly a portion of a label which may be bound to a bias or sense electrode; an oxidation or reduction of a label may result in a change in a tunneling current amplitude.

In some cases, polymerases or polymerase complexes may be positioned randomly using a Poisson distribution, such that some electrode pairs may have more than one polymerase or polymerase complex bound in close proximity thereto. Software, firmware, analog comparators, or built in logic may be used to determine which electrode pairs may have more than one polymerase as a result of higher current, or a multilevel current distribution which does not fit an expected distribution associated with a set of provided tunneling labels. Some electrode pairs may have currents consistent with a lack of a polymerase or polymerase complex, as may be determined by a low signal, and or a distribution that may not match an expected distribution associated with a provided set of tunneling label compounds. Such an expected distribution of tunneling label compounds may include one, two, three, four, or more than four different types of tunneling compound labels.

In some cases a mixture of incorporable and unincorporable nucleotides may be used. Incorporable and unincorporable nucleotides may both be labeled, and may be utilized with a reagent mixture. A reagent mixture may or may not comprise catalytic cations such as catalytic divalent cations. In cases where catalytic divalent cations are not comprised in the mixture, incorporation of nucleotides may not be possible. In some cases, all or substantially all nucleotides may comprise labels, and may be unincorporable.

Chip Fluidics

In some cases, a chip may have a single common sample volume, so that a single input fluid, which may comprise input samples, may interact with all sensors of a chip. Alternatively, a chip may have multiple volumes associated with different sets of sensors, and may have a valving mechanism or multiple input ports, so that different input fluids, which may comprise different input samples, may interact with different sets of samples.

In some cases, a single input fluid may comprise multiple different samples. The different samples may be differentiated as a result of having different bar codes associated thereto, or may have different cleavable tunneling labels affixed thereto. In some cases, different samples may be introduced at different times. Different samples may occupy a portion of different chip area while leaving other sensors available for a sample which may be introduced at a later time. Different samples may be differentiated by measuring a label bound to or associated with a bound moiety, which may be an enzyme complexed with a nucleic acid polymer, thus indicating when a bound moiety was bound, and in which locations bound moieties were bound. After introduction of a subsequent sample, additional measurement(s) may be made to measure labels bound or associated with bound moieties. Additional sensors with bound moieties may be associated with the newly introduced samples and sensors which were previously associated with a previous sample may still be associated with a same sample to which a previous sensor was associated. In some cases, all sensors in association with a chip may undergo different steps at a same or at different times. In some cases, samples may be introduced at different times, but other fluids may be introduced to all sensors at a same time.

In some cases, a chip may have multiple input ports associated with different internal volumes, and a system may accommodate multiple chips simultaneously. Different fluids may be introduced to different volumes at different times. Different volumes may be different volumes of a single chip, different volumes may be on different chips. Different volumes may be different volumes associated with multiple chips, thereby allowing different steps in a process to occur at different times in the different volumes, which may for example, allow different volumes to have measurements done at different times, while other volumes may have other different steps occurring while measurements are occurring. By so doing, measurements may occur effectively continuously, thereby allowing analog to digital converters, integrators, digital communications channels, or any other portion of the electronics, which may otherwise be a limiting factor to the throughput of the system to be fully utilized, and not limited by waiting for a chemistry, biochemistry, wash or other step or steps to occur. In some cases, a coordinated set of measurements may be effectuated, whereby the measurements may not be effectively continuous, but may occur over an increased percentage or duty cycle in comparison to where all measurements of different areas were performed, prior to proceeding to a different step, which may be a chemistry step, a biochemistry step, a wash step, or any step other than a measurement step.

Figure 3Y:
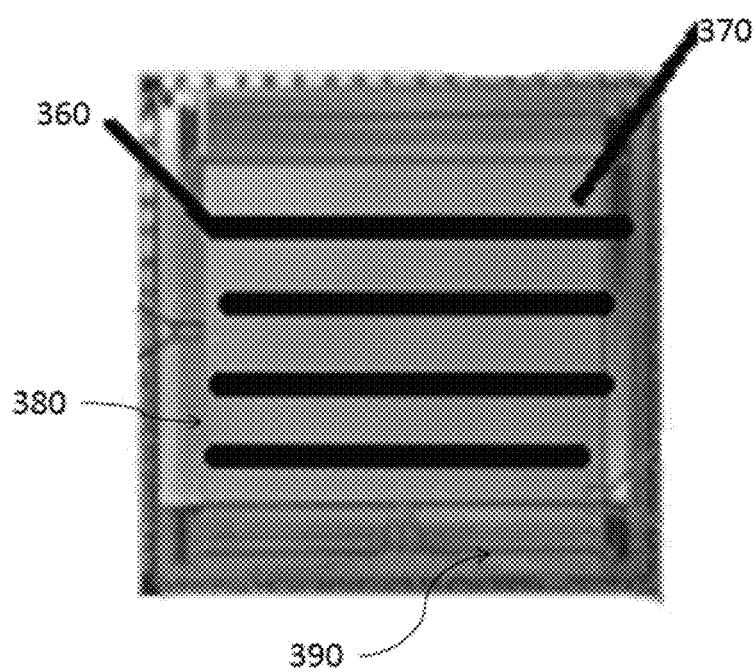
FIG. 3Y shows a chip with multiple fluidic pathways for sensor arrays and associated circuitry.

In some cases as shown in FIG. 3Y, a chip may have multiple fluidic channels 370, which may be interconnected such that a single sample may be utilized, or may have separate fluidic ports (not shown) so that different samples may be utilized in different sections of the chip. Sense circuitry 360, which may include integrating capacitors, current mirrors and analog to digital converters may be placed in sections between fluidic regions which may have two sets of 100 rows or some other appropriate number of rows, such that each region between fluidic channels may support a cover to the fluidic channel, and permit a much lower fluidic volume to be utilized. Row select circuitry 380 may be positioned to one side, while digital input output circuitry 390, which may comprise one or more LVDS (Low Voltage Differential Signals) interface may be utilized.

In some cases, single physical volume within a chip may be separated into individual fluidic volumes using electrowetting or optoelectrowetting, thereby allowing greater flexibility than might be achievable using fixed volumes. Electrowetting may be used to define different regions of sensors. Different regions of sensors may be associated with different samples, and or may be used to define fluidic flow regions, so as to allow flow of different reagents to different portions of the chip at different times, which may be associated with different samples, or may be associated with regions sized for optimal chip throughput, thus allowing for different sample sizes while optionally allowing maximal throughput.

In some cases, target, sample, or label molecules may be removed using electric fields applied between an electrode and a bulk solution. A field used may be lower than a field strength needed to remove a target binding moiety, for example, a thiol bound oligos may have their complement denatured at lower field strength than a thiol bound oligo, thus allowing denaturation without affecting a SAM.

Sensor Read Details

In some cases, to achieve a more accurate background level, a background level may be measured without binding of non-catalytic divalent cations. This background level may be used to find true signal values and separate signal from background. In some cases, quantitation of a signal, which may be from a label or labels, may result from measurement over a period of time wherein a label or labels may be effectively fixedly bound to SAMs associated with electrodes of an electrode pair, while there may be essentially no background molecules which might otherwise bind and influence a measurement of a label or labels which may be fixedly bound. Background molecules may be removed for example, by washing of the sensor chip area, from a volume containing the electrodes of an electrode pair, or may be prevented from interacting with an electrode pair as a result of fields associated with the electrodes of an electrode pair. In some cases, a signal level may indicate an identity of a label type, wherein several different label types with different tunneling and hopping conductances may be utilized, but only one type may be bound. A current level may indicate a number of labels which may be bound, wherein a single type of label which may have a single tunneling or hopping conductance may be utilized, and variations may result from a difference in a number of labels which may be bound. A current may result from a combination of different types of labels, which may have different tunneling or hopping conductances, and may result from different numbers of labels being bound, particularly if a number of labels is measured repeatedly, and with time a number of labels may increase to a fixed number as result of a fixed size of an electrode pair surface area.

In some cases, a noise level may be considered to comprise tunneling and or hopping noise, amplifier noise, analog to digital conversion noise, kinetics of polymerase binding of labeled nucleobases, and kinetics of sticky ends of nucleotide labels bound by polymerase binding to stuck ends of SAMs.

In some cases, a system which may utilize tunneling and or hopping labels for detection in a method for determining a sequence and or epigenetics for a nucleic acid sequence may utilize fixed time periods for the determination or sequence and or epigenetics. In other cases, different time periods may be used, which may be fixed for different sets of nucleotides, or may be settable by a user as desired for desired accuracy level. In some cases, different time periods may be used by a system for different volumes or areas of a single chip concurrently, or may be used by a system for different chips concurrently, or a combination of different regions of different chips in different chips concurrently.

In some cases, different sets of nucleotides may have consistent levels of salt concentrations, pH, temperature, and other conditions or other elements comprising a buffer containing a set of nucleotides may be the same for different sets of nucleotides. In other cases, different sets of nucleotides may have different levels of salt concentrations, pH, temperature, and other conditions or other elements comprising a buffer containing a set of nucleotides for different sets of nucleotides, which may be useful for increasing a difference in binding kinetics to better separate and better identify different types of nucleobases.

Sensor Read Configurability

In some cases, a single measurement may be utilized with a fixed time, wherein an electronic sensor circuit associated with an electrode pair may continuously integrate a current originating from an electrode pair. In some cases, a number of measurements may be made, where a time associated with each measurement may be the same, or different, for example, to enable a wider dynamic range associated with different labels and or different kinetics associated with binding of different nucleotides.

In some cases, a system and associated chemistry may be configured for comparatively slower but more accurate detection. Such a system may utilize a synchronous chemistry method, wherein various different reagents may be delivered in association with an incorporation of a single base or a single base type. A system of this case may be made to be massively parallel to improve throughput, such as utilizing a chip with 10 million (M), 20M, 30M, 40M, 50M, 60M, 70M, 80M, 90M, 100M, 200M, 300M, 400M, 500M, 600M, 700M, 800M, 900M, 1 billion (B), 2B, 3B, 4B, 5B, 6B, 7B, 8B, 9B, 10B, 15B, 20B or more sensors.

As provided herein, a system and associated chemistry may be configured for fast detection of long oligomers, for example using an asynchronous chemistry method. Some or all appropriate incorporable nucleotides may be provided to polymerase complexes, and detectors may sample data at a rate higher than an average incorporation rate, so that signals associated with non-binding times may be followed by signals associated with binding times of nucleobases, and an incorporation order may be determined by monitoring and analysis of these signals. In some cases, the rate of incorporation may be adjusted by using a mixture of divalent cations may include both catalytic and non-catalytic cations.

In some cases, one or more portions of a system may utilize a slower biochemistry with a massively parallel high throughput portion, and some other portions of a system may utilize a biochemistry which may be configured for fast detection of long oligomers, thereby providing a system which provides both large numbers of short reads and smaller numbers of long reads, so that a scaffold and data to fill in the scaffold may be produced simultaneously.

In some cases, one or more portions of a system may utilize a slower biochemistry with a massively parallel high throughput portion, and some other portions of a system may utilize a biochemistry which may be configured for multi segment detection or multiple skip read method sequencing, whereby a portion of an oligo may be read using a "slow" biochemistry, and then a set of appropriate nucleobases may be provided, such that hundreds or thousands of bases may be incorporated in a period of seconds or minutes, and may thence be followed with a period of "slow" biochemistry, thus providing reads which may be separated by hundreds or thousands of bases on the same oligo, thereby providing a system which provides both large numbers of short reads and smaller numbers of nucleic acids which may utilize a skip read method, so that a scaffold and data to fill in the scaffold may be produced simultaneously.

In some cases, a combination of sequencing and epigenetics detection may be utilized in different portions or at different times in a system, with optional feedback to determine epigenetics at specific locations using targeted sequencing, or using shotgun sequencing. In particular, some portions of a targeted sample may be separated from other portions of a targeted sample such as gene promoter regions, and other specifically targeted regions which may be introns or exons or other portions of a genome, and may be performed without epigenetic determination.

In some cases, different readout schemes may be employed for different regions of a device, or at different times in one or more regions of a device. In some cases, simultaneous single point readout and kinetics may be used in one or more regions or at one or more times, whereby a sequence and or one type of epigenetics may be determined. In some cases, multi-point detection using multiple nucleotides sets may be used in one or more regions or at one or more times. Multi-point detection may be used in conjunction with an asynchronous chemistry method readout which may be used in one or more regions or at one or more times in a device.

In some cases, a field-programmable gate array (FPGA) or other programmable logic within a chip may be used to permit changes in readout pattern and or timing.

In some cases, a storage device may be used to store positions of active sites, where memory may be used as part of readout process to determine which locations are active. A storage device may be selected as a flash memory or a ram. A storage device may be used by an onboard microprocessor, or may be used in conjunction with an FPGA or other programmable logic in order to determine a pattern of sensor location to read and or a pattern of locations to not read. In some embodiments, different patterns may be utilized in different regions, whereby, different timings may be utilized between reads, for example when one region is utilized for synchronous chemistry method reads, and another region is used for asynchronous chemistry method reads.

In some cases, data collection from tunneling sensors may be collected at a rate which may be too slow to determine nucleotide binding times, and may further average current levels from a number of nucleotide binding events and intervening time periods between binding events. Currents over this time may be averaged in hardware, using for example, an integrating amplifier. Multiple data acquisitions may occur in order to provide further averaging, and thus better signal to noise. A kinetic rate may be determined in part by knowing $k_{on}$ and $k_{off}$, and thus a type of nucleobase being bound and being bound to may be determined by an average current level, combined with a set of provided nucleobases and associated labels. Such a method may allow for a minimum generation of data while still enabling identification of bases and optionally epigenetic modifications to bases of a sample polynucleotide.

In cases where a data collection rate may be faster than nucleotide binding kinetics, a number of data acquisitions may occur for each binding event, and one or more binding events may be observed for each base position before an incorporation of a nucleobase occurs. This may directly allow better determination of kinetic information. In some cases, a system may be configured to continuously acquire data, which may comprise data acquisition during binding events, between binding events, and during incorporation events.

In some cases as an example, it may be desirable to have a sequencing chemistry cycle time of about three minutes. This cycle may include washes, adding nucleotides, adding Mg, and read times. In some cases, a faster cycle time may be desirable and attainable due to the lack of susceptibility of a system to dephasing.

In some cases, in order to achieve a desired cycle time, both a time between binding events or time to bind $t_b$, and a length of a binding event or disassociation time $t_d$ may be adjusted; $t_b$ primarily by adjusting nucleotide concentration, and $t_d$ by adjusting a ratio of Ca and other divalent cations. So in some cases wherein a time of about one second may be selected for an integration time, this time when combined with a multiplexing level of one hundred, corresponding to one hundred rows on a sensor, may give a total readout time of about one hundred seconds, leaving a similar amount of time for other parts of a chemistry cycle time, when utilizing a total chemistry cycle time of about three minutes.

In some cases, it may be desirable to have a specified accuracy for a read, whereby it may be desirable in some cases to average measurements from several nucleotide binding periods, wherein such a desired number may be ten with a 50 percent duty cycle, thus resulting in a 10 Hz binding rate. In other cases, if better accuracy is needed or desired, nucleotide binding kinetics may be increased by utilizing faster hybridization binding, by taking several readings, or by extending the integration time.

In some cases, nucleotide binding may not be directly measured; instead measurements may be made of a tunneling label hybridization binding. A length of a hybridization binding time may be influenced by temperature, salt concentration, pH, electrode potentials, sticky end length, and sticky end sequence (GC vs. 7-deazaadenine). In further cases, a time between hybridization events may also affected by all of the previous items, although to a lesser extent, and may also be affected by the SAM density, and linker length and stiffness. In some cases, hybridization binding time and time between hybridization binding events may be thereby adjusted.

In some cases a timing cycle may be utilized which may average multiple hybridizing binding events (per nucleotide binding event). For example, the number of hybridization binding events may be 10, with a 50% duty cycle, resulting in 10 events within each 50 ms time period associated with an average nucleotide binding event, resulting in hybridization event taking an average of 2.5 ms. Thus when used with a label with a tunneling conductance which may result in a continuous tunneling current of 1 nA, a signal during a one second integration time period may be 250 pC.

Sample Preparation

In some cases, prior to any sequencing preparation steps, a system which may include a tunneling and or hopping detector may isolate and separate one or more cells from a sample, using e.g., flow cytometry. One or more cells may comprise circulating tumor cells, live cells, specifically stained cells, or combinations thereof. Stained cells may comprise a stain which may be a fluorescent stain. A stain may comprise a tunneling and or hopping label. A stain may comprise an electrochemical label. In some cases, a pullout method which uses target specific pullout methods, such as antibody magnetic bead isolation, or aptamer isolation methods may be used to isolate target cells. Individual cells or sets of cells may then be sequenced, wherein DNA genome (s) and or RNA transcriptome(s) may be sequenced.

In some cases, enrichment may be performed for either specific sequences of RNA and or DNA, or for specific types of DNA or RNA, such as mRNA or tRNA. Specific targets may be isolated from the isolated cells. Enrichment of specific sequences of RNA and or DNA, or specific types of DNA or RNA such as mRNA or tRNA may be performed. Isolated nucleic acid strands may then be sequenced. Specific transcripts such as for AR-V7 may be isolated and quantified, allowing for confirmation of target transcript as well as quantitation and detection of any epigenetic modifications, mutations or splice variants, which may further allow determination of a source tissue type for a tumor cell. Such a quantification step may result from sequencing, digital PCR, qPCR, isothermal amplification, or any other appropriate target quantification process.

In some cases, after cell isolation, an enrichment or concentration step may be performed for all DNA, all nucleic acids strands, or all RNA. An enrichment or concentration step may be performed in place of a specific target isolation step. An enrichment or concentration step may be performed in addition to a specific isolation step. An enrichment or concentration step may allow, for example, a very high sensitivity for specific targets, while allowing for a complete genome and or transcriptome to be completed, which may be at lower coverage than sequencing of a specific target. In some cases, genome sequencing and or transcriptome may be combined with another quantitation technique, potentially in a same chip.

Similarly, a pullout of circulating free DNA may be used to capture subsequent sequencing targeting mutations such as BRAF mutations associated with melanoma, or other mutations targeted as a result of association with other genetic diseases.

In some cases, in order to better insure a one to one correspondence between enzymes and linkers during a process in which the enzymes and linkers are bound together, a linker may be bound to a first terminus of a protein which comprises at least a part of an enzyme, thus allowing a one to one correspondence between linkers and enzymes.

In some cases, linkers, magnetic or paramagnetic beads or linkers may be reversibly bound to a surface at an average spacing such that only one corresponding moiety may bind thereto as a result of the physical distance therebetween. This may provide a one to one binding ratio which may exceed a Poisson distribution, by providing an equal number of bound and unbound moieties, or by providing more unbound moieties and then removing unbound moieties. Binding may occur in solution, whereby one moiety may be present at a higher concentration, such that most of the moiety with a lower concentration may bind to a single moiety of moieties at a higher concentration. Lower concentration moieties may then be reversibly bound to a surface. A surface may be a surface of a magnetic bead, and may be separated from unbound higher concentration moieties.

In some cases, moieties, which may comprise enzymes, magnetic, paramagnetic particles or beads or linkers may formed into emulsions. Emulsions may be formed under conditions which do not allow enzymatic activity prior to formation of emulsions. For example, primed nucleic acid circles or double stranded nucleic acid circles with nick sites may be provided prebound to an enzyme, or magnetic or paramagnetic particle, wherein one to one binding is not required, but a Poisson distribution which favors single moieties with circular nucleic acid polymers may be utilized. The emulsion, which may be a water in oil emulsion, may further comprise in the aqueous emulsions, nucleotides, buffer appropriate to enzymatic activity, and enzymes useful for extension of a primer or nicked strand of a nucleic acid polymer strand. If an enzyme is to be bound to one of the one or more circular nucleic acid polymers, it may be provided at a concentration such that a Poisson distribution favors a single enzyme in each emulsion. Conditions, which may include temperature, may then be changed, so that extension may proceed. n enzyme may perform a rolling circle amplification until such time as nucleotides within the emulsions may be effectively fully utilized during the rolling circle amplification, thereby providing a physical blocker bound to an emulsion, regardless of the number of circular nucleic acid polymers provided to the emulsions. Size of physical blockers may vary depending upon variations in emulsion sizes and variations in nucleotide concentration in each emulsion.

In further cases, a library preparation method may include a process of producing a complementary cDNA, RNA or DNA strand, so as to minimize creation of secondary structure. A library preparation method may include a process which ligates a universal primer region, which may be a hairpin structure 420 such as that depicted in FIG. 4 which may have a nick site 450, whereby a nick may be created in the hairpin structure 420 by a nickase or similar enzyme, which may thereby allow binding of a RNA dependent RNA polymerase, a DNA dependent DNA polymerase, or a reverse transcriptase to bind at the nick site 450, and may either as a result of inherent strand displacement or as a result of action by a helicase, which may be bound or may operate separately, allow incorporation of bases and translocation along the un-nicked nucleic acid polymer, thus allowing resequencing of a sample strand 410 without circularization. In some cases, a hairpin structure 420 may comprise one or more inosines 460, so as to allow binding to different target sequences without requiring a set or larger set of universal primers. In some cases, wherein a polymerase or ligase may have a lower activity and or lower specificity when binding to an inosine, a portion of the hairpin structure may comprise a set of universal primers, such that a base immediately at an active site of an enzyme may be one of a set of natural bases 440A and 440B. In further cases, a hairpin universal primer may have a length of complementary bases which may be sufficiently long for a ligase to function without reduced activity due to steric hindrance from the curvature of the hairpin portion of a hairpin universal primer, and may be similarly sufficiently long for a polymerase to extend a universal primer without reduced activity due to the curvature of a hairpin universal primer.

Additional System Components

In some cases, a pump or other source of positive or negative pressure may be used to move a solution containing the polymerase into the electrode gaps. Once a polymerase is immobilized or trapped at the narrowing channel, DNA or other solutions may be added.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method for sequencing a sample nucleic acid, comprising:
   (a) using a polymerase adjacent to two opposed electrodes on a substrate to bind the sample nucleic acid, wherein the two opposed electrodes at least partially form a gap between the two opposed electrodes, the gap having a width, the width having variation about a nominal value defining a nominal width;
   (b) flowing four sets of nucleotides having tunneling labels, each set of nucleotides having a different tunneling label, wherein the tunneling label is larger than the nominal width of the gap between the two opposed electrodes;
   (c) applying a bias voltage to bias a first electrode of the two opposed electrodes relative to a second electrode of the two opposed electrodes;
   (d) determining a conductance between the two opposed electrodes caused by a localization of one of the tunneling labels from one nucleotide of the four sets of nucleotides within the gap of the two opposed electrodes when the polymerase incorporates the one nucleotide to a complementary base; and
   (e) using at least a tunneling current measured for the determining the conductance in (d) to identify the complementary base;
   wherein, after the tunneling label is bound to the first electrode, the tunneling label is bound to the second electrode in a region of the second electrode, the region having a shape of a cross section of a torus, wherein a first diameter of an inner ring of the cross section of the torus and a second diameter of an outer ring of the cross section of the torus result from at least a combination of flexibility of the tunneling label and angular flexibility of binding moieties.

2. The method of claim 1, wherein the tunneling label comprises a zwitterionic compound.

3. The method of claim 1, wherein the tunneling label comprises a nucleic acid strand.

4. The method of claim 3, wherein the nucleic acid strand is greater than 10 bases long.

5. The method of claim 3, wherein the nucleic acid strand has a double stranded portion and a single stranded portion.

6. The method of claim 1, further comprising binding the polymerase to a dielectric between the two opposed electrodes.

7. The method of claim 1, further comprising binding the polymerase to one of the two opposed electrodes.

8. The method of claim 1, wherein the gap between the two opposed electrodes has a first portion having a width that is greater than a size of the polymerase and a second portion having a width that is smaller than the size of the polymerase.

9. The method of claim 1, wherein a self-assembled monolayer is bound to each of the two opposed electrodes.

10. The method of claim 9, wherein each of the self-assembled monolayers is bound by a thiol to each of the two opposed electrodes.

11. The method of claim 9, wherein at least one of the self-assembled monolayers comprises at least in part a nucleic acid which binds to at least a part of a nucleic acid strand comprised in the tunneling label.

12. The method of claim 11, wherein the at least one of the self-assembled monolayers transiently binds to the at least the part of the nucleic acid strand.

13. The method of claim 1, wherein said one nucleotide further comprises a terminator.

14. The method of claim 13, wherein said terminator is bound to the 3' of a ribose of the one nucleotide.

15. A method comprising:
   (a) using a polymerase adjacent to two opposed electrodes on a substrate to bind a nucleobase having a tunneling label attached thereto, said nucleobase complementary to an interrogated base of a sample nucleic acid, wherein the two opposed electrodes at least partially form a gap between the two opposed electrodes, the gap having a width, the width having variation about a nominal value defining a nominal width, and wherein the tunneling label is larger than the nominal width of the gap between the two opposed electrodes;
   (b) applying a bias voltage to bias a first electrode of the two opposed electrodes relative to a second electrode of the two opposed electrodes;
   (c) measuring a current signal comprising a combination of at least one tunneling current and at least one hopping current between the two opposed electrodes caused by localization of the tunneling label to the two opposed electrodes; and
   (d) identifying a matching nucleobase on a single stranded portion of the sample nucleic acid based at least in part on the current signal measured in (c) wherein, after the tunneling label is bound to the first electrode, the tunneling label is bound to the second electrode in a region of the second electrode, the region having a shape of a cross section of a torus, wherein a first diameter of an inner ring of the cross section of the torus and a second diameter of an outer ring of the cross section of the torus result from at least a combination of flexibility of the tunneling label and angular flexibility of binding moieties.

16. The method of claim 15, wherein the tunneling label comprises a zwitterionic compound.

17. The method of claim 15, wherein the tunneling label comprises a nucleic acid strand.

18. The method of claim 17, wherein the nucleic acid strand is greater than 10 bases long.

19. The method of claim 17, wherein the nucleic acid strand has a double stranded portion and a single stranded portion.

20. The method of claim 15, further comprising binding the polymerase to a dielectric between the two opposed electrodes.

* * * * *